(12) United States Patent
Ceccarelli et al.

(10) Patent No.: US 7,189,850 B2
(45) Date of Patent: Mar. 13, 2007

(54) TRIAZA-SPIROPIPERIDINE DERIVATIVES

(75) Inventors: Simona Maria Ceccarelli, Basel (CH); Emmanuel Pinard, Linsdorf (FR); Henri Stalder, Basel (CH)

(73) Assignee: Hoffmann-La Roche Inc., Nutley, NJ (US)

( * ) Notice: Subject to any disclaimer, the term of this patent is extended or adjusted under 35 U.S.C. 154(b) by 323 days.

(21) Appl. No.: 10/967,534

(22) Filed: Oct. 18, 2004

(65) Prior Publication Data

US 2005/0107373 A1    May 19, 2005

(30) Foreign Application Priority Data

Oct. 23, 2003    (EP)    ............................ 03024415

(51) Int. Cl.
*C07D 471/10* (2006.01)
(52) U.S. Cl. ...................................... 546/20
(58) Field of Classification Search .................. 546/20
See application file for complete search history.

(56) References Cited

FOREIGN PATENT DOCUMENTS

EP          0 921 125         6/1999
WO    WO 2004/072034    *    8/2004

OTHER PUBLICATIONS

Lewis D.A. & Lieberman J.A., Neuron. vol. 28, pp. 325-334 (2000).
Vandenberg R. J. & Aubrey K. R., Exp. Opin. Ther. Targets vol. 5(4) pp. 507-518 (2001).
Nakazato A. & Okuyama S., Exp. Opin. Ther. Patents vol. 10(1) pp. 75-98 (2000).
Sharma T., Br. J. Psychiatry, vol. 174 (Suppl. 38) pp. 44-51 (1999).
Javitt D. C. et al., Biol. Psychiatry, vol. 45 pp. 668-679 (1999).
Mohn A. R. et al., Cell vol. 98 pp. 427-436 (1999).
Bliss, T. V. & Collingridge G. L., Nature, vol. 361 pp. 31-39 (1993).
Tang J. P. et al., Nature, vol. 401, pp. 63-69 (1999).
Gainetdinov R. R. et al., Trends in Pharm. Sci. vol. 23(8) pp. 367-373 (2002).
Lopez-Corcuera B, et al., Mol. Mem. Biol. vol. 18 pp. 13-20 (2001).
Bergeron R. et al., Proc. Natl. Acad. Sci. USA vol. 95, pp. 15730-15734 (1998).
Chen et al., J. Neurophysiol. vol. 89(2) pp. 691-703 (2003).
Armer R. E. & Miller D. J., Exp. Opin Ther. Patents vol. 11 (4) pp. 563-572 (2001).
Pralong E. et al., Prog. Neurobiol. vol. 67, pp. 173-202 (2002).
Carlsson M. L., J. Neural Trans. vol. 105, pp. 525-535 (1998).

* cited by examiner

*Primary Examiner*—D. Margaret Seaman
*Assistant Examiner*—Nizal S. Chandrakumar
(74) *Attorney, Agent, or Firm*—George W. Johnston; Patricia S. Rocha-Tramaloni; Kimberly J. Prior

(57) ABSTRACT

The invention relates to compounds of the general formula

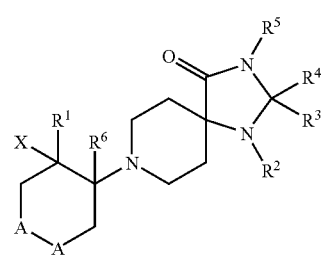

wherein
A-A is —$CH_2$—$CH_2$—, —$CH_2$—$CH_2$—$CH_2$—, —$CH_2$—O— or —O—$CH_2$—; and
X, $R^1$, $R^2$, $R^3$, $R^4$, $R^5$, $R^6$, n, and p are as defined herein, or a pharmaceutically acceptable salt thereof for the treatment of psychoses, pain, neurodegenerative dysfunction in memory and learning, schizophrenia, dementia and other diseases in which cognitive processes are impaired, such as attention deficit disorders or Alzheimer's disease.

25 Claims, No Drawings

TRIAZA-SPIROPIPERIDINE DERIVATIVES

BACKGROUND OF THE INVENTION

Schizophrenia is a progressive and devastating neurological disease characterized by episodic positive symptoms such as delusions, hallucinations, thought disorders and psychosis and persistent negative symptoms such as flattened affect, impaired attention and social withdrawal, and cognitive impairments (Lewis D A and Lieberman J A, *Neuron*, 28:325–33, 2000). For decades research has focused on the "dopaminergic hyperactivity" hypothesis which has led to therapeutic interventions involving blockade of the dopaminergic system (Vandenberg R J and Aubrey K R., *Exp. Opin. Ther. Targets*, 5(4): 507–518, 2001; Nakazato A and Okuyama S, et al., *Exp. Opin. Ther. Patents*, 10(1): 75–98, 2000). This pharmacological approach poorly address negative and cognitive symptoms which are the best predictors of functional outcome (Sharma T., *Br. J. Psychiatry*, 174(suppl. 28): 44–51, 1999).

A complementary model of schizophrenia was proposed in the mid-1960' based upon the psychotomimetic action caused by the blockade of the glutamate system by compounds like phencyclidine (PCP) and related agents (ketamine) which are non-competitive NMDA receptor antagonists. Interestingly in healthy volunteers, PCP-induced psychotomimetic action incorporates positive and negative symptoms as well as cognitive dysfunction, thus closely resembling schizophrenia in patients (Javitt D C et al., *Biol. Psychiatry*, 45: 668–679, 1999). Furthermore transgenic mice expressing reduced levels of the NMDAR1 subunit displays behavioral abnormalities similar to those observed in pharmacologically induced models of schizophrenia, supporting a model in which reduced NMDA receptor activity results in schizophrenia-like behavior (Mohn A R et al., *Cell*, 98: 427–236, 1999).

Glutamate neurotransmission, in particular NMDA receptor activity, plays a critical role in synaptic plasticity, learning and memory, such as the NMDA receptors appears to serve as a graded switch for gating the threshold of synaptic plasticity and memory formation (Wiley, NY; Bliss T V and Collingridge G L, *Nature*, 361: 31–39, 1993). Transgenic mice overexpressing the NMDA NR2B subunit exhibit enhanced synaptic plasticity and superior ability in learning and memory (Tang J P et al., *Natur*, 401–63–69, 1999).

Thus, if a glutamate deficit is implicate in the pathophysiology of schizophrenia, enhancing glutamate transmission, in particular via NMDA receptor activation, would be predicted to produce both anti-psychotic and cognitive enhancing effects.

The amino acid glycine is known to have at least two important functions in the CNS. It acts as an inhibitory amino acid, binding to strychnine sensitive glycine receptors, and it also influences excitatory activity, acting as an essential co-agonist with glutamate for N-methyl-D-aspartate (NMDA) receptor function. While glutamate is released in an activity-dependent manner from synaptic terminals, glycine is apparently present at a more constant level and seems to modulate/control the receptor for its response to glutamate.

One of the most effective ways to control synaptic concentrations of neurotransmitter is to influence their re-uptake at the synapses. Neurotransmitter transporters by removing neurotransmitters from the extracellular space, can control their extracellular lifetime and thereby modulate the magnitude of the synaptic transmission (Gainetdinov R R et al, *Trends in Pharm. Sci.*, 23(8): 367–373, 2002).

Glycine transporters, which form part of the sodium and chloride family of neurotransmitter transporters, play an important role in the termination of post-synaptic glycinergic actions and mnaintenance of low extracellular glycine concentration by re-uptake of glycine into presynaptic nerve terminals and surrounding fine glial processes.

Two distinct glycine transporter genes have been cloned (GlyT-1 and GlyT-2) from mammalian brain, which give rise to two transporters with ~50% amino acid sequence homology. GlyT-1 presents four isoforms arising from alternative splicing and alternative promoter usage (1a, 1b, 1c and 1d). Only two of these isoforms have been found in rodent brain (GlyT-1a and GlyT-1b). GlyT-2 also presents some degree of heterogeneity. Two GlyT-2 isoforms (2a and 2b) have been identified in rodent brains. GlyT-1 is known to be located in CNS and in peripheral tissues, whereas GlyT-2 is specific to the CNS. GlyT-1 has a predominantly glial distribution and is found not only in areas corresponding to strychnine sensitive glycine receptors but also outside these areas, where it has been postulated to be involved in modulation of NMDA receptor function (Lopez-Corcuera B et al., *Mol. Mem. Biol.*, 18: 13–20, 2001). Thus, one strategy to enhance NMDA receptor activity is to elevate the glycine concentration in the local microenvironment of synaptic NMDA receptors by inhibition of GlyT-1 transporter (Bergereon R. et al., *Proc. Nati. Acad. Sci. USA*, 95: 15730–15734, 1998; Chen L. et al., *J. Neurophysiol.*, 89(2): 691–703, 2003).

Glycine transporters inhibitors are suitable for the treatment of neurological and neuropsychiatric disorders. The majority of diseases states implicated are psychoses, schizophrenia (Armer R E and Miller D J, *Exp. Opin. Ther. Patents*, 11 (4): 563–572, 2001), psychotic mood disorders such as severe major depressive disorder, mood disorders associated with psychotic disorders such as acute mania or depression, associated with bipolar disorders and mood disorders, associated with schizophrenia, (Pralong E T et al., *Prog. Neurobiol.*, 67: 173–202, 2002), autistic disorders (Carlsson M L, *J. Neural Trans,.* 105: 525–535, 1998), cognitive disorders such as dementias, including age related dementia and senile dementia of the Alzheimer type, memory disorders in a mammal, including a human, attention deficit disorders and pain (Armer R E and Miller D J, *Exp. Opin. Ther. Patents*, 11 (4): 563–572, 2001).

Thus, increasing activation of NMDA receptors via GlyT-1 inhibition may lead to agents that treat psychosis, schizophrenia, dementia and other diseases in which cognitive processes are impaired, such as attention deficit disorders or Alzheimer's disease.

SUMMARY OF THE INVENTION

The present invention provides compounds of formula I per se and pharmaceutically acceptable salts of such compounds, as well as methods for their manufacture. The invention also provides pharmaceutical compositions containing compounds of formula I or a pharmaceutically acceptable salt thereof and methods for the manufacture of these compositions. The invention further provides methods for the treatment of diseases related to activation of NMDA receptors via Glyt-1 inhibition. For example, the invention provides methods for the control or prevention of illnesses such as psychoses, dysfunction in memory and learning, schizophrenia, dementia and other diseases in which cognitive processes are impaired, such as attention deficit disorders or Alzheimer's diseases. The preferred indications using the compounds of the present invention are schizophrenia, cognitive impairment and Alzheimer's disease.

In particular, the present invention relates to compounds of formula

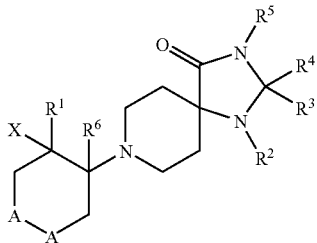

I wherein
A-A is —CH$_2$—CH$_2$—, —CH$_2$—CH$_2$—CH$_2$—, —CH$_2$—O— or —O—CH$_2$—;
X is hydrogen or hydroxy;
R$^1$ is aryl or heteroaryl, each of which is unsubstituted or substituted by one or more substituents selected from the group consisting of lower alkyl, lower alkoxy, halogen and trifluoromethyl;
R$^2$ is aryl or heteroaryl, each of which is unsubstituted or substituted by one or more substituents selected from the group consisting of lower alkyl, lower alkoxy, halogen and trifluoromethyl,
  or is lower alkyl, —(CH$_2$)$_n$-cycloalkyl, —(CH$_2$)$_n$—CF$_3$, —(CH$_2$)$_p$—O-lower alkyl, —(CH$_2$)$_y$-phenyl optionally substituted by halogen, lower alkyl, lower alkoxy or trifluoromethyl,
  or is —(CH$_2$)$_p$—NR'R" wherein R' and R" form together with the N-atom to which they are attached a heterocyclic ring selected from the group consisting of piperidine, morpholine, thiomorpholine and 1,1-dioxothiomorpholine;
R$^3$, R$^4$ are each independently hydrogen, lower alkyl phenyl or benzyl;
R$^5$ is hydrogen, lower alkly or benzyl;
R$^6$ is hydrogen or lower alkyl;
n is 0, 1 or 2;
p is 2 or 3; and
y is 1 or 2;

or a pharmaceutically acceptable acid addition salt thereof.
Furthermore, the invention includes all racemic mixtures, all their corresponding enantiomers and/or optical isomers.

The present invention relates to compounds of general formula I, to pharmaceutical composition containing them and their use in the treatment of neurological and neuropsychiatric disorders. It has surprisingly been found that the compounds of general formula I are good inhibitors of the glycine transporter 1 (GlyT-1), and that they have a good selectivity to glycine transporter 2 (GlyT-2) inhibitors.

DETAILED DESCRIPTION OF THE INVENTION

The following definitions of general terms used herein apply irrespective of whether the terms in question appear alone or in combination. It must be noted that, as used in the specification and the appended claims, the singular forms "a", "an," and "the" include plural forms unless the context clearly dictates otherwise.

As used herein, the term "alkyl" denotes a saturated straight- or branched-chain group containing from 1 to 7 carbon atoms, for example, methyl, ethyl, propyl, isopropyl, n-butyl, i-butyl, 2-butyl, t-butyl and the like. Preferred alkyl groups are groups with 1–6 carbon atoms.

The term "cycloalkyl" denotes a saturated or partially saturated ring containing from 3 to 7 carbon atoms, for example cyclopropyl, cyclopentyl, cyclopentenyl, cyclohexyl, cyclohexenyl, cycloheptyl or cycloheptenyl.

The term "halogen" denotes chlorine, iodine, fluorine and bromine.

The term "aryl" denotes a monovalent cyclic aromatic hydrocarbon radical consisting of one or more fused rings in which at least one ring is aromatic in nature, for example phenyl or naphthyl.

The term "heteroaryl" denotes a monovalent aromatic carbocyclic radical, for example pyridyl, pyrazinyl, pyrimidinyl, pyridazinyl, triazinyl, thiazolyl, thienyl, furyl, pyrrolyl, imidazolyl, pyrazolyl, oxazolyl, isothiazolyl or isoxazolyl.

"Pharmaceutically acceptable," such as pharmaceutically acceptable carrier, excipient, etc., means pharmacologically acceptable and substantially non-toxic to the subject to which the particular compound is administered.

The term "pharmaceutically acceptable acid addition salts" embraces salts with inorganic and organic acids, such as hydrochloric acid, nitric acid, sulfuric acid, phosphoric acid, citric acid, formic acid, fumaric acid, maleic acid, acetic acid, succinic acid, tartaric acid, methane-sulfonic acid, p-toluenesulfonic acid and the like.

The term "therapeutically effective amount" means an amount that is effective to prevent, alleviate or ameliorate symptoms of disease or prolong the survival of the subject being treated.

The present invention provides compounds of formula

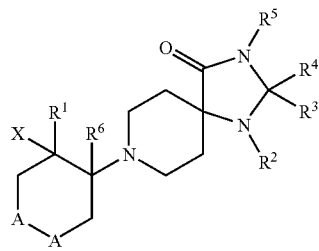

I wherein
A-A is —CH$_2$—CH$_2$—, —CH$_2$—CH$_2$—CH$_2$—, —CH$_2$—O— or —O—CH$_2$—;
X is hydrogen or hydroxy;
R$^1$ is aryl or heteroaryl, each of which is unsubstituted or substituted by one or more substituents selected from the group consisting of lower alkyl, lower alkoxy, halogen and trifluoromethyl;
R$^2$ is aryl or heteroaryl, each of which is unsubstituted or substituted by one or more substituents selected from the group consisting of lower alkyl, lower alkoxy, halogen and trifluoromethyl,
  or is lower alkyl, —(CH$_2$)$_n$-cycloalkyl, —(CH$_2$)$_n$—CF$_3$, —(CH$_2$)$_p$—O-lower alkyl, —(CH$_2$)$_y$-phenyl optionally substituted by halogen, lower alkyl, lower alkoxy or trifluoromethyl,
  or is —(CH$_2$)$_p$—NR'R" wherein R' and R" form together with the N-atom to which they are attached a heterocyclic ring selected from the group consisting of piperidine, morpholine, thiomorpholine and 1,1-dioxothiomorpholine;
R$^3$, R$^4$ are each independently hydrogen, lower alkly, phenyl or benzyl;
R$^5$ is hydrogen, lower alkyl or benzyl;
R$^6$ is hydrogen or lower alkyl;
n is 0, 1 or 2;
p is 2 or 3; and
y is 1 or 2;

or a pharmaceutically acceptable acid addition salt thereof.

Preferred compounds of formula I are those, wherein A-A is —CH$_2$—CH$_2$—. Especially preferred are compounds of formula

I'

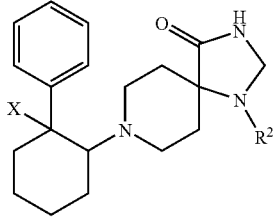

wherein

X is hydrogen or hydroxy;

R$^2$ is —(CH$_2$)$_n$-phenyl, unsubstituted or substituted by one or more substituents, selected from the group consisting of lower alkyl, lower alkoxy, halogen or trifluoromethyl, and pharmaceutically acceptable acid addition salts thereof, n is 0, 1, or 2.

Examples of such compounds include (rac,cis)-1-phenyl-8-(2-phenyl-cyclohexyl)-1,3,8-triaza-spiro[4.5]decan-4-one, (1R,2R)-1-phenyl-8-(2-phenyl-cyclohexyl)-1,3,8-triaza-spiro[4.5]decan-4-one, (rac,cis)-1-(4-chloro-phenyl)-8-(2-phenyl-cyclohexyl)-1,3,8-triaza-spiro[4.5]decan-4-one, (rac,cis)-1-phenethyl-8-(2-phenyl-cyclohexyl)-1,3,8-triaza-spiro[4.5]decan-4-one, (rac,cis)-1-(3,4-dichloro-phenyl)-8-(2-phenyl-cyclohexyl)-1,3,8-triaza-spiro[4.5]decan-4-one, (rac,cis)-8-(2-phenyl-cyclohexyl)-1-(4-trifluoromethyl-phenyl)-1,3,8-triaza-spiro[4.5]decan-4-one, (rac,trans)-1-phenyl-8-(2-phenyl-cyclohexyl)-1,3,8-triaza-spiro[4.5]decan-4-one, (rac,trans)-8-(2-hydroxy-2-phenyl-cyclohexyl)-1-phenyl-1,3,8-triaza-spiro[4.5]decan-4-one, (rac,cis)-1-(4-methoxy-phenyl)-8-(2-phenyl-cyclohexyl)-1,3,8-triaza-spiro[4.5]decan-4-one and (rac,cis)-8-(2-hydroxy-2-phenyl-cyclohexyl)-1-phenyl-1,3,8-triaza-spiro[4.5]decan-4-one.

Especially preferred are further compounds of formula I', wherein X is hydrogen or hydroxy and R$^2$ is lower alkyl or —(CH$_2$)$_n$-cycloalkyl, for example the following compounds:

(rac,cis)-1-isobutyl-8-(2-phenyl-cyclohexyl)-1,3,8-triaza-spiro[4.5]decan-4-one, (rac,cis)-1-pentyl-8-(2-phenyl-cyclohexyl)-1,3,8-triaza-spiro[4.5]decan-4-one, (rac,cis)-1-(3-methyl-butyl)-8-(2-phenyl-cyclohexyl)-1,3,8-triaza-spiro[4.5]decan-4-one, (rac,cis)-1-cyclohexylmethyl-8-(2-phenyl-cyclohexyl)-1,3,8-triaza-spiro[4.5]decan-4-one, (rac,cis)-1-(2-cyclohexyl-ethyl)-8-(2-phenyl-cyclohexyl)-1,3,8-triaza-spiro[4.5]decan-4-one, (rac,cis)-1-hexyl-8-(2-phenyl-cyclohexyl)-1,3,8-triaza-spiro[4.5]decan-4-one and (rac,cis)-1-cyclohexylmethyl-8-(2-hydroxy-2-phenyl-cyclohexyl)-1,3,8-triaza-spiro[4.5]decan-4-one.

Further especially preferred are compounds of formula

I''

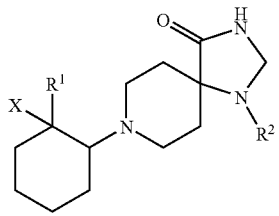

wherein

X is hydrogen or hydroxy;

R$^1$ is phenyl substituted by one or more substituents selected from the group consisting of lower alkyl, lower alkoxy, halogen and trifluoromethyl;

R$^2$ is phenyl, unsubstituted or substituted by one or more substituents selected from the group consisting of lower alkyl, lower alkoxy, halogen and trifluoromethyl.

Examples of this group are the following compounds:

(rac,cis)-1-phenyl-8-(2-p-tolyl-cyclohexyl)-1,3,8-triaza-spiro[4.5]decan-4-one, (rac,cis)-8-[2-(4-fluoro-phenyl)-cyclohexyl]-1-phenyl-1,3,8-triaza-spiro[4.5]decan-4-one, (rac,cis)-8-[2-(4-chloro-phenyl)-cyclohexyl]-1-phenyl-1,3,8-triaza-spiro[4.5]decan-4-one, (rac,cis)-8-[2-(3,4-dichloro-phenyl)-cyclohexyl]-1-phenyl-1,3,8-triaza-spiro[4.5]decan-4-one, (rac,cis)-8-[2-(4-chloro-phenyl)-cyclohexyl]-1-(4-fluoro-phenyl)-1,3,8-triaza-spiro[4.5]decan-4-one, (rac,cis)-1-(4-fluoro-phenyl)-8-(2-p-tolyl-cyclohexyl)-1,3,8-triaza-spiro[4.5]decan-4-one, (rac,cis)-1-(4-fluoro-phenyl)-8-[2-(4-fluoro-phenyl)-cyclohexyl]-1,3,8-triaza-spiro[4.5]decan-4-one, (rac,cis)-8-[2-(4-fluoro-phenyl)-2-hydroxy-cyclohexyl]-1-phenyl-1,3,8-triaza-spiro[4.5]decan-4-one, (rac,cis)-8-(2-hydroxy-2-o-tolyl-cyclohexyl)-1-phenyl-1,3,8-triaza-spiro[4.5]decan-4-one, (rac,cis)-8-[2-(4-chloro-phenyl)-2-hydroxy-cyclohexyl]-1-phenyl-1,3,8-triaza-spiro[4.5]decan-4-one, (rac,cis)-1-(4-fluoro-phenyl)-8-[2-(4-fluoro-phenyl)-2-hydroxy-cyclohexyl]-1,3,8-triaza-spiro[4.5]decan-4-one, (rac,cis)-8-[2-(4-chloro-phenyl)-2-hydroxy-cyclohexyl]-1-(4-fluoro-phenyl)-1,3,8-triaza-spiro[4.5]decan-4-one, (rac,cis)-1-(4-chloro-phenyl)-8-[2-(4-fluoro-phenyl)-2-hydroxy-cyclohexyl]-1,3,8-triaza-spiro[4.5]decan-4-one, (rac,cis)-1-(4-chloro-phenyl)-8-[2-(4-chloro-phenyl)-2-hydroxy-cyclohexyl]-1,3,8-triaza-spiro[4.5]decan-4-one, (rac,cis)-8-[2-(4-fluoro-phenyl)-2-hydroxy-cyclohexyl]-1-p-tolyl-1,3,8-triaza-spiro[4.5]decan-4-one and (rac,cis)-8-[2-(4-chloro-phenyl)-2-hydroxy-cyclohexyl]-1-(4-methoxy-phenyl)-1,3,8-triaza-spiro[4.5]decan-4-one.

Further especially preferred are compounds of formula I'', wherein X is hydrogen or hydroxy, R$^1$ is pyridin-4-yl and R$^2$ is as described above. An example of such group is (rac,cis) 8-(2-hydroxy-2-pyridin-4-yl-cyclohexyl)-1-phenyl-1,3,8-triaza-spiro[4.5]decan-4-one.

Preferred are compounds of formula I, wherein A-A is —O—CH$_2$— and the other substituents are as described for formula I above. A compound of this group is (rac,cis)-8-(3-hydroxy-3-phenyl-tetrahydro-pyran-4-yl)-1-phenyl-1,3,8-triaza-spiro[4.5]decan-4-one.

Preferred are further compounds of formula I, wherein A-A is —CH$_2$—O— and the other substituents are as described for formula I above. Compounds of these groups are (rac,cis)-8-(4-hydroxy-4-phenyl-tetrahydro-pyran-3-yl)-1-(3,3,3-trifluoro-propyl)-1,3,8-triaza-spiro[4.5]decan-4-one and (rac,cis)-8-(4-hydroxy-4-phenyl-tetrahydro-pyran-3-yl)-1-phenyl-1,3,8-triaza-spiro[4.5]decan-4-one.

Encompassed by the present invention are also compounds, wherein A-A is —(CH$_2$)$_3$—.

The present compounds of formula I and their pharmaceutically acceptable salts can be prepared by methods known in the art, for example, by processes described below, which process comprises a) reacting a compound of formula

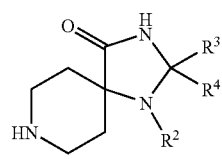

2 with a compound of formula

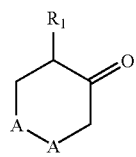

3 to produce a compound of formula

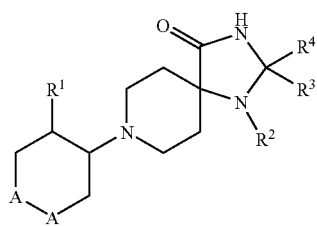

Ia wherein the substituents are as defined above, or b) reacting a compound of formula

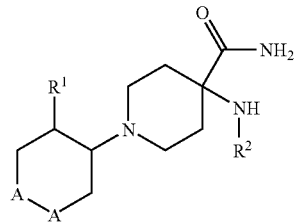

13 with corresponding acetals or ketals to produce a compound of formula

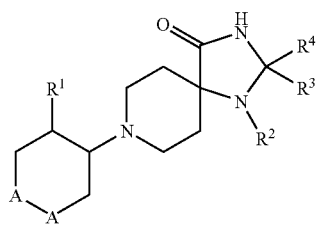

Ia wherein the substituents are as defined above, or c) reacting a compound of formula

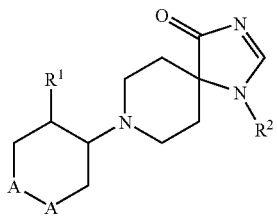

14 with a Grignard reagent R$^3$MgX to produce a compound of formula

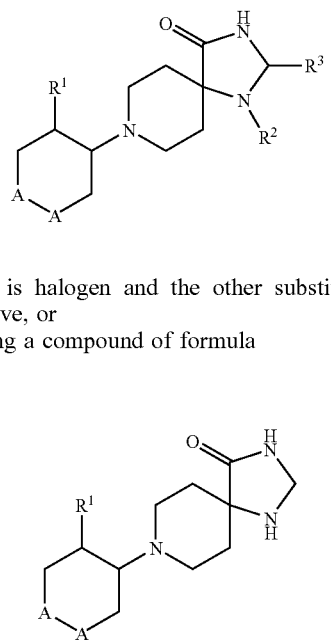

Ic wherein X is halogen and the other substituents are as defined above, or d) reacting a compound of formula

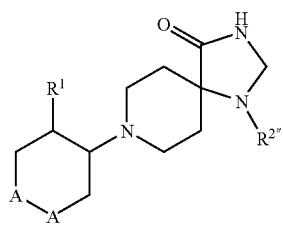

Id with a compound of formula R$^{2'}$CHO to produce a compound of formula

Ib' wherein R$^{2'}$ is lower alkyl, —(CH$_2$)$_x$-cycloalkyl, —(CH$_2$)$_x$—CF$_3$,
—(CH$_2$)$_y$—O-lower alkyl, —(CH$_2$)$_x$-phenyl optionally substituted by halogen, lower alkyl, lower alkoxy or trifluoromethyl,
or is —(CH$_2$)$_y$—NR'R" wherein R' and R" form together with the N-atom to which they are attached a heterocyclic ring selected from the group consisting of piperidine, morpholine, thiomorpholine or 1,1-dioxo-thiomorpholine, $R^{2'''}$ is lower alkyl, —$(CH_2)_y$-cycloalkyl, —$(CH_2)_y$—$CF_3$, —$(CH_2)_p$—O-lower alkyl, —$(CH_2)_y$-phenyl optionally substituted by halogen, lower alkyl, lower alkoxy or trifluoromethyl, where x is 0 or 1, y is 1 or 2, and p is 2 or 3;

or is —$(CH_2)_p$—NR'R" wherein R' and R" form together with the N-atom to which they are attached a heterocyclic ring selected from the group consisting of piperidine, morpholine, thiomorpholine and 1,1-dioxo-thiomorpholine; x is 0 or 1; y is 1 or 2, and the other substituents are as defined above, or e) reducing a compound of formula

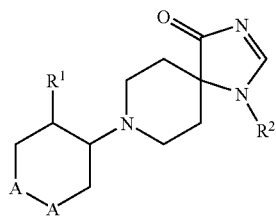

14 to a compound of formula

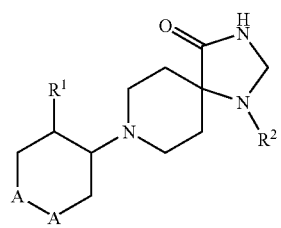

Ib wherein the substituents are as defined above, or f) reacting a compound of formula

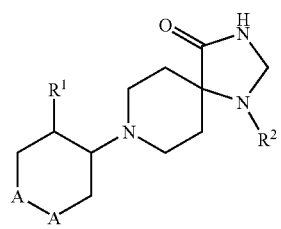

Ib with a compound of formula $R^5X$
to produce a compound of formula

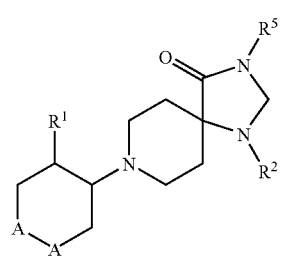

Ie wherein X is halogen and the other substituents are as defined above, or g) reacting a compound of formula

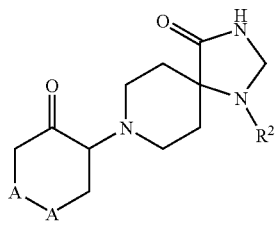

21 with a compound of formula $LiR^1$
to produce a compound of formula

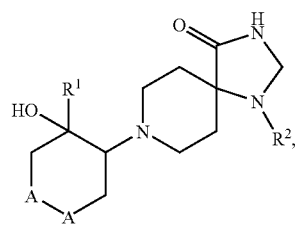

If wherein the substituents are as described above, or h) reacting a compound of formula

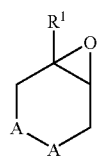

23 with a compound of formula

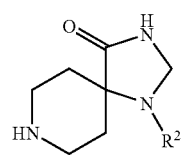

10 to produce a compound of formula

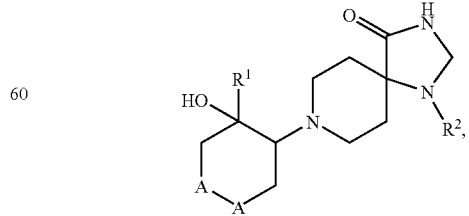

If wherein the substituents are as described above, or i) reacting a compound of formula

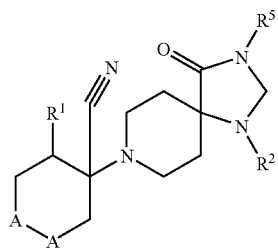

with $R^6MgX$ to produce a compound of formula

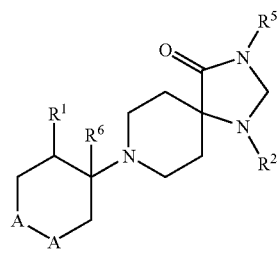

Ih wherein X is halogen and $R^6$ is lower alkyl and the other substituents are as described above, and if desired, converting the compounds obtained into pharmaceutically acceptable acid addition salts.

The compounds of formula I may be prepared in accordance with process variants a) to i), with the following schemes 1 to 11 and in accordance with the described examples 1 to 103.

The starting material is commercially available or may be prepared in accordance with known methods.

The compounds of the invention can be prepared by processes analogous to those established in the art.

1. Preparation of Compounds of Formula I Following Procedure A

Compounds of formula I with $R^1$–$R^4$ as defined above and A-A is —$(CH_2)_p$— are prepared by reductive amination of 2-aryl or 2-heteroaryl-cyclohexanone or 2-aryl or 2-heteroaryl-cycloheptanone (3) and an accordingly substituted 1,3,8-triazaspiro[4.5]decan-4-one (2) using procedures established in the art, such as reacting the two components in presence of titanium(IV) tetraisopropoxide in an organic solvent, e.g. EtOH or THF, at ambient temperature to reflux temperature for 1–48 h, preferred 20 h, followed by reduction of the intermediate with a reductive agent, preferred a borohydride like $NaBH_3CN$, $NaBH(OAc)_3$ or $NaBH_4$, at ambient temperature to reflux temperature, preferred 20° C. to 50° C.

Procedure A

Scheme 1

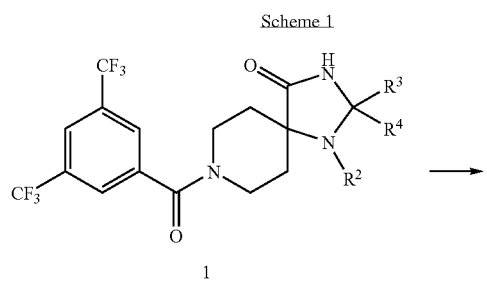

1

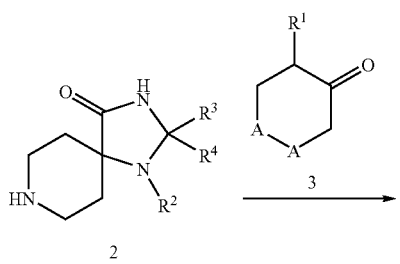

2

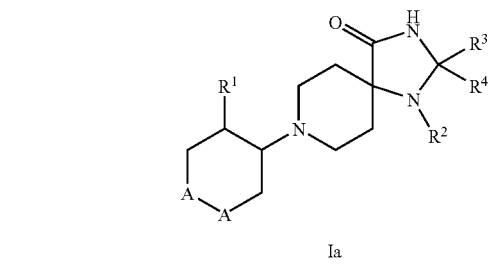

Ia

The substituted 1,3,8-triazaspiro[4.5]decan-4-ones (2) with $R^2$, $R^3$ and $R^4$ as defined above are prepared from accordingly substituted 8-(3,5-bis-trifluoromethyl-benzoyl)-1,3,8-triaza-spiro[4.5]decan-4-ones (1) (described in WO0194346) by hydrolysis of the starting material with an inorganic base, e.g. NaOH or LiOH.

Procedure A1

Scheme 2

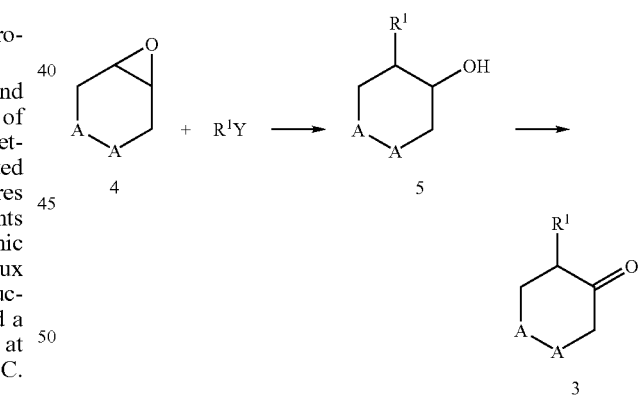

Building Block A

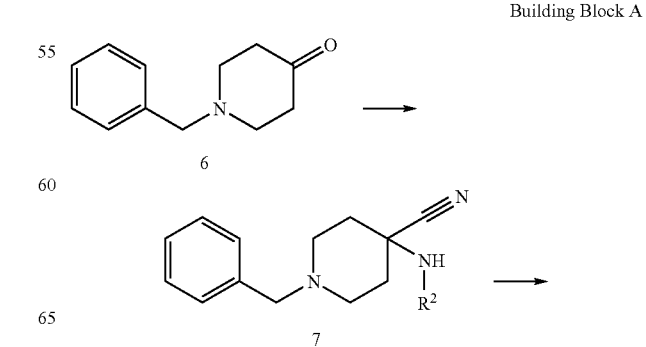

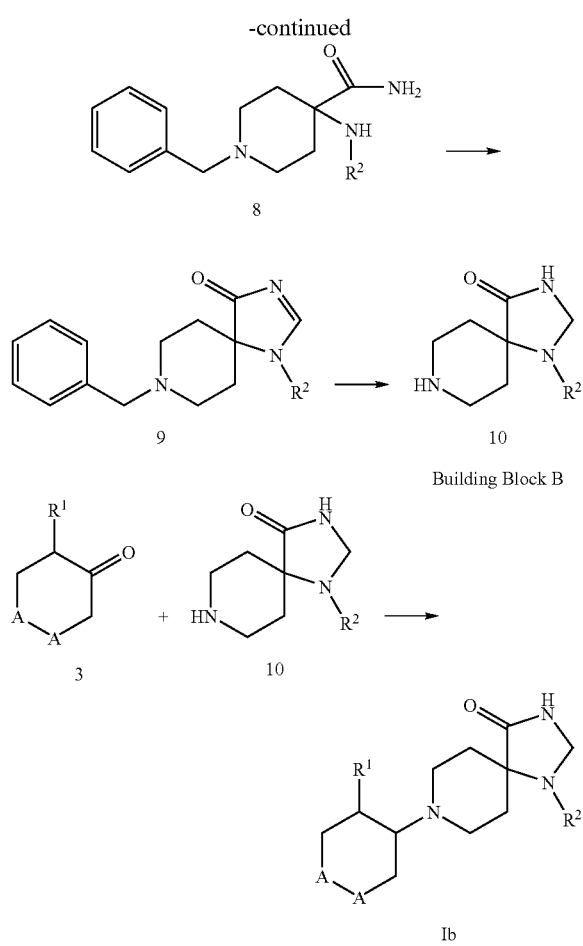

Building Block B

The new 2-aryl or 2-heteroaryl cyclohexanones or 2-aryl or 2-heteroaryl cycloheptanones (3) (Building Block A) are prepared in analogy to congeners already described in the literature. The first step, reaction of the cyclohexene oxide or cycloheptene oxide with chloro-, bromo- or iodo-magnesium or lithium aryl derivatives ($R^1Y$) provides the corresponding 2aryl-cyclohexanols (5) (*Tetrahedron:Asymmetry* 5, 223, 1994 and *J. Am. Chem. Soc.*, 106, 3693, 1984), which are oxidised with periodinane (Dess-Martin reagent) following a known procedure (*J. Org. Cem.*, 59, 7549, 1994).

The new 1,3,8-triaza-spiro[4.5]decan-4-ones (10) (Building Block B) are prepared in analogy to procedures described in the literature for the synthesis of such compounds starting from N-protected piperidin-4-ones (6). The 1-benzyl-4-piperidone is first submitted to a Strecker type synthesis providing the 4-cyano-4-amino derivative (7), which is treated with 90% sulfuric acid for 1 h to 40 h, preferred 2 h to 4 h at ambient temperature to provide the 4-amido-4-amino compound (8). This compound is then heated together with triethyl orthoformate in presence of acetic acid to reflux temperature for 20 h to 72 h, preferred for 24 h to 48 h, or under microwave irradiation to 120° C. to 200° C., preferred 150° C. to 200° C. for 10 min. to 30 min., preferred 15 min. to 20 min. The resulting 1-benzyl-spiro-imine (9) is then hydrogenated in presence of Pd on charcoal in a suitable solvent providing the de-protected and saturated 1,3,8-triaza-spiro[4.5]decan-4-ones (10).

Building blocks A and B are submitted to a reductive amination as described above for Procedure A.

2. Preparation of Compounds of Formula I Following Procedure B

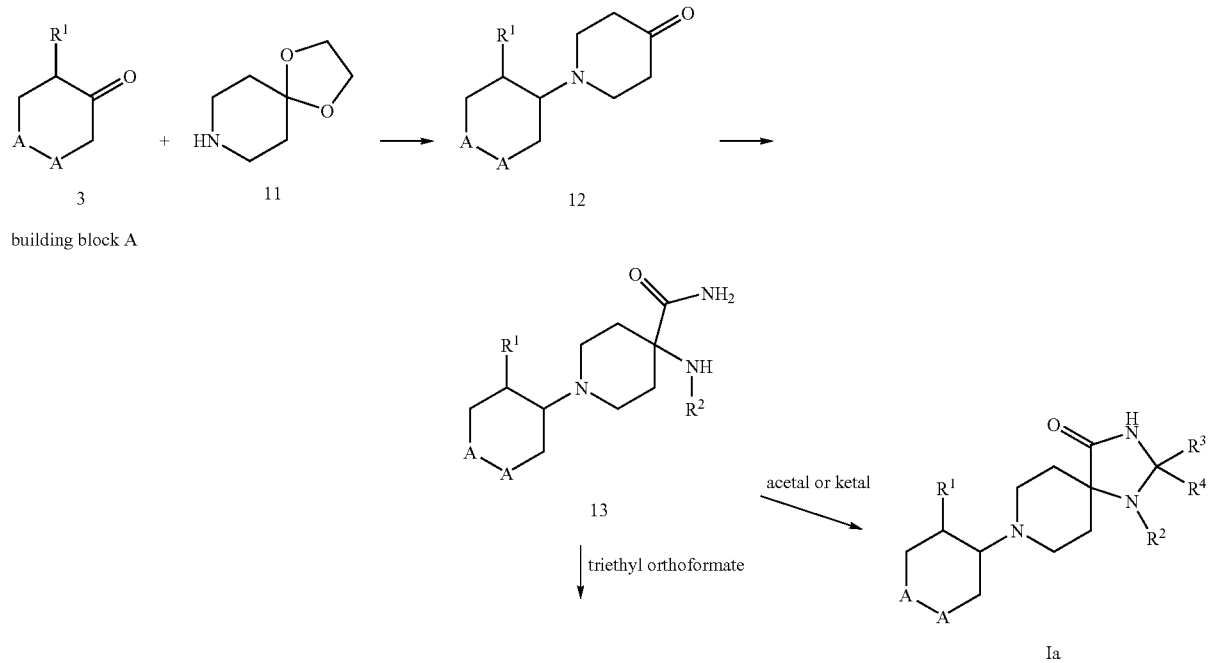

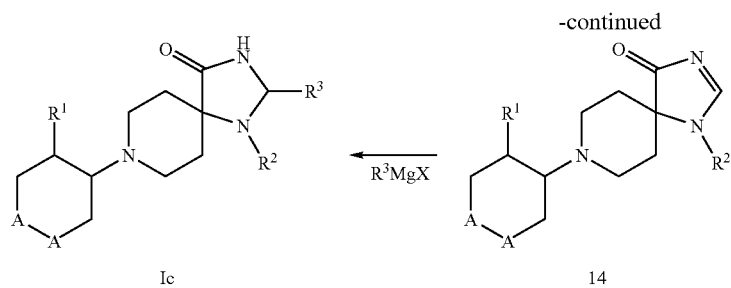

Piperidones (12) are synthesised in two steps from 2-aryl or 2-heteroaryl cyclohexanone or from 2-aryl or 2-heteroaryl cycloheptanone (3) and 1,4-dioxa-8-aza-spiro[4,5]decane (11). The reductive amination can be performed following the procedures already mentioned in Procedure A or via the corresponding enamines which are obtained by condensation of the starting materials under acidic conditions, e.g. with p-toluenesulfonic acid, in an azeotrope forming solvent like toluene at reflux temperature for 16 to 48 hours, preferably 24 hours, in an apparatus equipped with a Dean-Stark trap. The enamines are reduced following the procedures described in Procedure A. Hydrolysis of the ketal under acidic conditions, preferably aqueous 6N HCl in methanol, at reflux temperature for 1 to 16 hours, preferably 2 to 4 hours, following textbook procedures provides piperidones (12). Following Procedure A1 for intermediate (8) in the synthesis of building block B provides intermediate (13) in Procedure B. Reaction of (13) with triethyl orthoformate provides 1,3,8-triaza-spiro[4.5]dec-2-en-4-one (14) which after reaction with a Grignard reagent $R^3MgX$ yields final product Ic.

Compounds Ia are synthesized by acid promoted condensation of intermediate (13) with acetals or ketals. The reaction is usually conducted in toluene in which the starting materials are dissolved. To control the exothermic reaction the acid, usually p-toluenesulfonic acid, is added portionwise.

Procedure B1

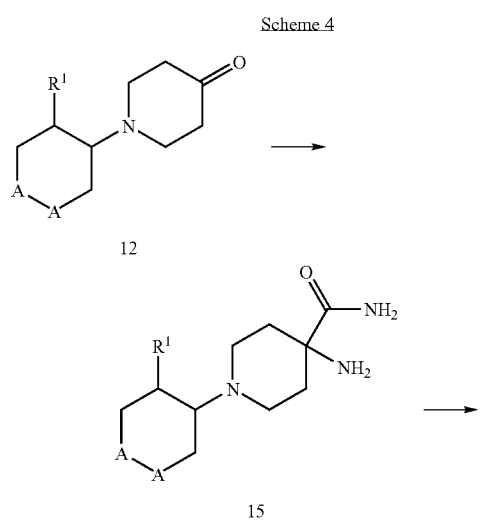

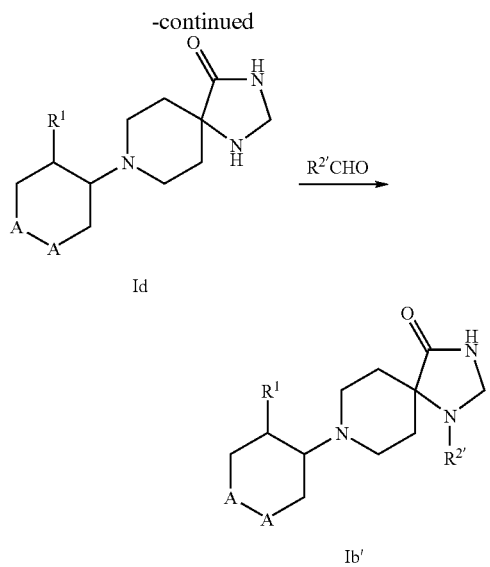

Scheme 4 describes the synthesis of compounds of formulas Id and Ib', wherein $R^{2'}$ is lower alkyl, —$(CH_2)_x$-cycloalkyl, —$(CH_2)_x$—$CF_3$, —$(CH_2)_y$—O-lower alkyl, —$(CH_2)_x$-phenyl, optionally substituted by halogen, lower alkyl, lower alkoxy or trifluoromethyl, or is —$(CH_2)_y$—NR'R", wherein R' and R" form together with the N-atom a heterocyclic ring, selected from the group consisting of piperidine, morpholine, thiomorpholine or 1,1-dioxo-thiomorpholine and $R^{2''}$ is lower alkyl, —$(CH_2)_y$-cycloalkyl, —$(CH_2)_y$—$CF_3$, —$(CH_2)_p$—O-lower alkyl, —$(CH_2)_y$-phenyl, optionally substituted by halogen, lower alkyl, lower alkoxy or trifluoromethyl, or is —$(CH_2)_p$—NR'R", wherein R' and R" form together with the N-atom a heterocyclic ring, selected from the group consisting of piperidine, morpholine, thiomorpholine and 1,1-dioxo-thiomorpholine, and the other substituents are as defined above.

The N(1)-unsubstituted 1,3,8-triaza-spiro[4.5]decan-4-ones Id are prepared following the reaction sequence described for Procedure B utilizing an ammonia equivalent like ammonium chloride. Reductive amination of Id following known procedures provides N-alkylated spiropiperidine Ib'. The reductive amination is done in presence of a borohydride, preferred $NaBH(OAc)_3$ or $NaBH_3CN$, or for less reactive aldehydes is run in two steps: firstly addition of the aldehyde to the amine in presence of titanium(IV) tetraisopropoxide followed by reduction of the intermediate product with a borohydride.

1. Preparation of Compounds of Formula I Following Procedure C

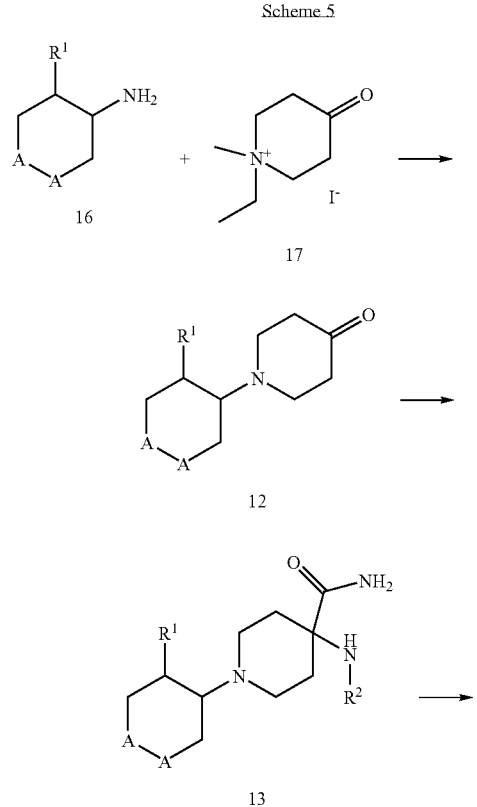

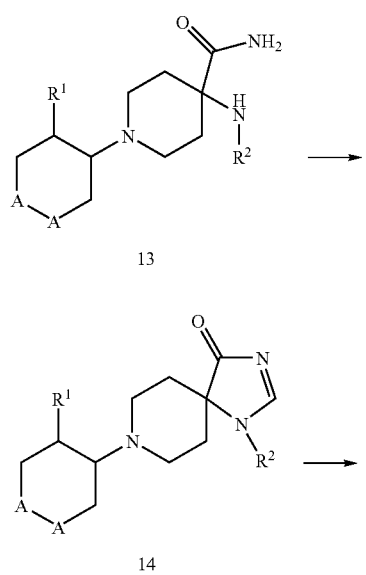

2-Aryl-cyclohexylamine (16) or 2-aryl-cycloheptylamine or 3-amino-4-aryl-tetrahydro-pyran or 4-amino-3-aryl-tetrahydro-pyran is reacted with 1-ethyl-1-methypiperidinium-4-one iodide (17) following a literature procedure (*J. Org. Chem.*, 60, 4324, 1995) to give racemic 1-(2-aryl-cyclohexyl)-piperidin-4-ones (12). These are then submitted to the reaction sequence already described in Procedure B to provide compounds of formula Ib.

3. Preparation of Compounds of Formula I Following Procedure D

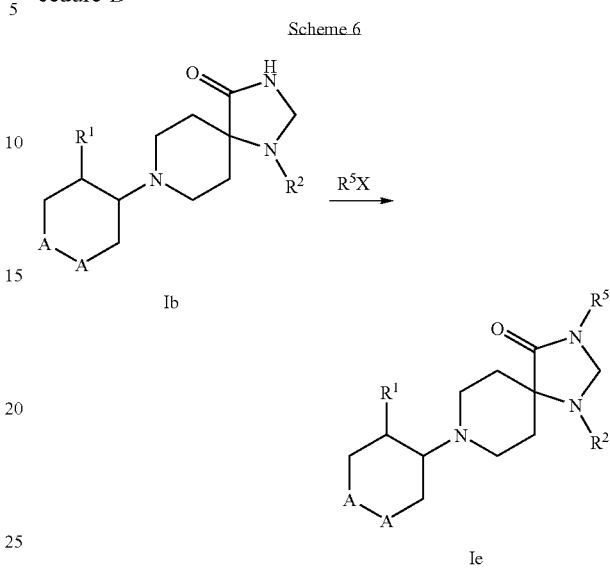

N(1)-substituted 8-(2-aryl-cyclohexyl)-1,3,8-triaza-spiro[4.5]decan-4-one (Ib) are deprotonated with a strong base, i.e. sodium hydride or potassium bis(trimethylsilyl)amide, and then reacted with the corresponding alkyl halide $R^5X$. The reactions are conducted in a polar, aprotic solvent, preferred is DMF, at ambient temperature.

4. Preparation of Compounds of Formula I Following Procedure E

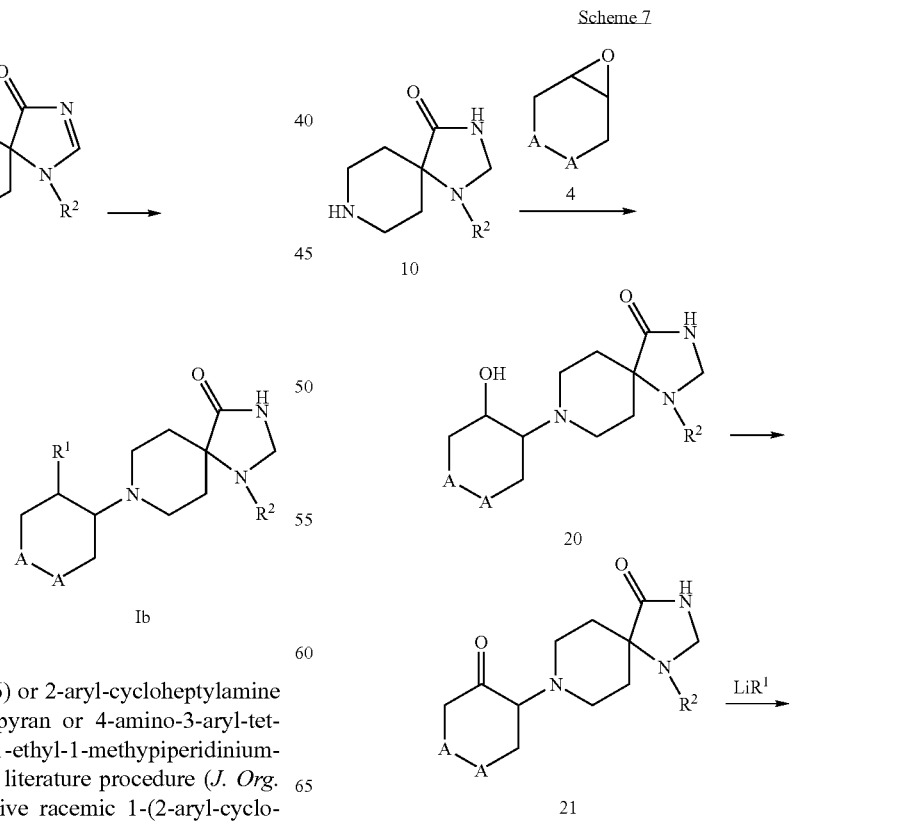

-continued

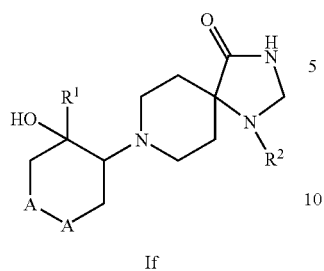

If

Reaction of 1,3,8-triaza-spiro[4,5]decan-4-one (10) with cyclohexene oxide (4) or 3,7-dioxa-bicyclo[4.1.0]heptane (4) in a polar solvent, e.g. ethanol, at reflux temperature for 16 to 35 hours, preferred 24 hours, or under microwave irradiation at 150° C. for 30 minutes provides 8-(2-hydroxy-cyclohexyl)-1,3,8-triaza-spiro[4,5]decan-4-ones (20). The reaction with 3,7-dioxa-bicyclo[4.1.0]heptane gives a mixture of regioisomers. Oxidation of (20) with e.g. sulfur trioxide-pyridine complex provides aminoketone (21) which on reaction with a lithium-aryl reagent $LiR^1$ leads to the final product If.

5. Preparation of Compounds of Formula I Following Procedure F

Scheme 8

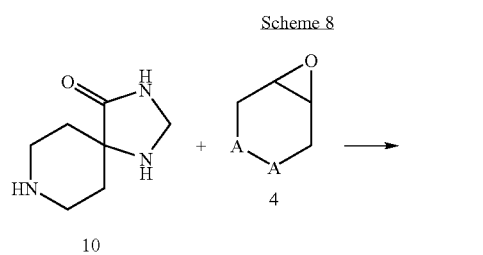

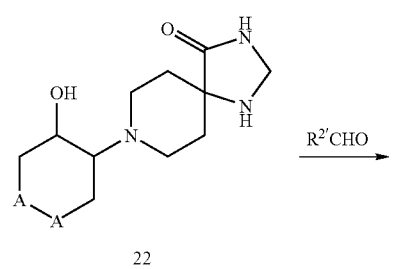

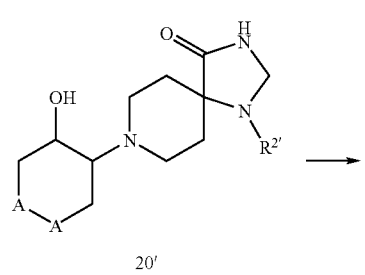

-continued

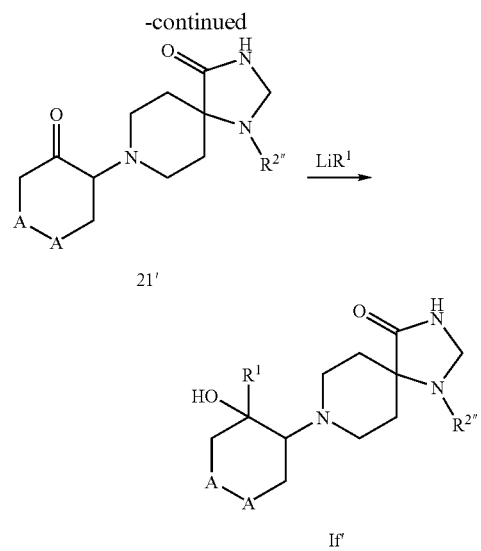

If' wherein $R^{2'}$ is lower alkyl, —$(CH_2)_x$-cycloalkyl, —$(CH_2)_x$—$CF_3$, —$(CH_2)_y$—O-lower alkyl, —$(CH_2)_x$-phenyl, optionally substituted by halogen, lower alkyl, lower alkoxy or trifluoromethyl, or is —$(CH_2)_y$—NR'R", wherein R' and R" form together with the N-atom a heterocyclic ring, selected from the group consisting of piperidine, morpholine, thiomorpholine and 1,1-dioxo-thiomorpholine and $R^{2''}$ is lower alkyl, —$(CH_2)_y$-cycloalkyl, —$(CH_2)_y$—$CF_3$, —$(CH_2)_p$—O-lower alkyl, —$(CH_2)_y$-phenyl, optionally substituted by halogen, lower alkyl, lower alkoxy or trifluoromethyl, or is —$(CH_2)_p$—NR'R", wherein R' and R" form together with the N-atom to which they are attached a heterocyclic ring, selected from the group consisting of piperidine, morpholine, thiomorpholine and 1,1-dioxo-thiomorpholine, and the other substituents are as defined above.

Reaction of 1,3,8-triaza-spiro[4,5]decan-4-one (10) with cyclohexene oxide (4) or 3,7-dioxa-bicyclo[4.1.0]heptane (4) in a polar solvent, e.g. ethanol, at reflux temperature for 16 to 35 hours, preferably 16 to 24 hours, or under microwave irradiation at 150° C. for 30 minutes provides 8-(2-hydroxyl-cyclohexyl)-1,3,8-triaza-spiro[4.5]decan-4-ones (22). The reaction with 3,7-dioxa-bicyclo[4.1.0]heptane gives a mixture of regioisomers. Reaction of (22) with an aldehyde $R^{2'}$CHO in presence of a reducing agent (reductive amination) provides N(1)-alkylated derivatives (20'). Oxidation of (20') with sulfur trioxide-pyridine complex gave aminoketone (21') which on reaction with a lithium-aryl reagent $LiR^1$ leads to the final product If'.

6. Preparation of Compounds of Formula I Following Procedure G

Scheme 9

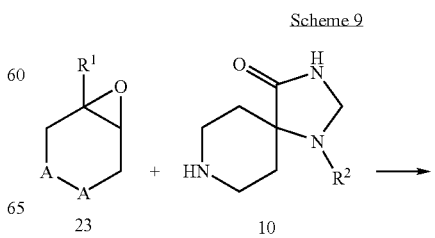

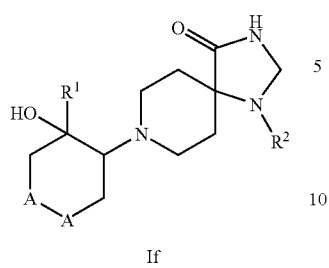

If

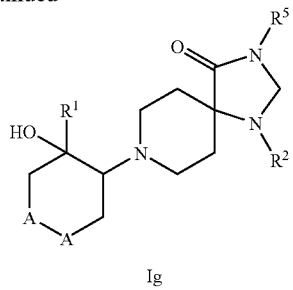

Ig

Reaction of 1-aryl-7-oxa-bicyclo[4.1.0]heptane (A-A=CH$_2$—CH$_2$) or its tetrahydropyran analogue (A-A=CH$_2$—O) (23) with 1,3,8-triaza-spiro[4,5]decan-4-one (10) provides the final product (If) in one step.

7. Preparation of Compounds of Formula I Following Procedure H

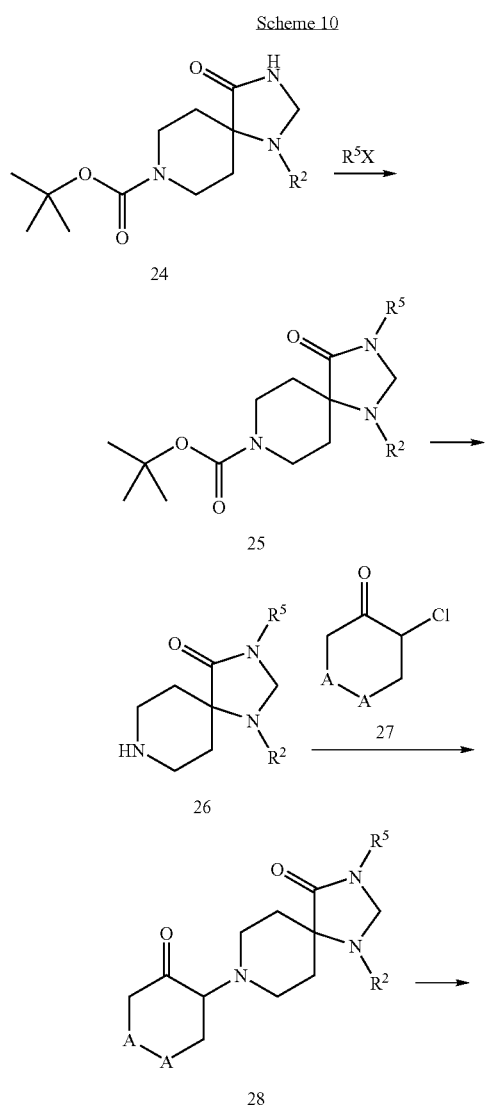

Alkylation of (24) utilizing the procedure already described in Procedure D gives compound (25). Deprotection of (25) under acidic conditions provides 1,3 disubstituted 1,3,8-triaza-spiro[4,5]decan-4-one (26) which on reaction with 2-chloro-cyclohexanone (27) or 3-chloro-tetrahydro-pyran-4-one (27) or 4-chloro-tetrahydro-pyran-3-one (27) provides ketone (28). Treatment of this ketone with a lithium-aryl reagent LiR$^1$ following the steps mentioned in Procedure E and Procedure F leads to the final product Ig.

8. Preparation of Compounds of Formula I Following Procedure I

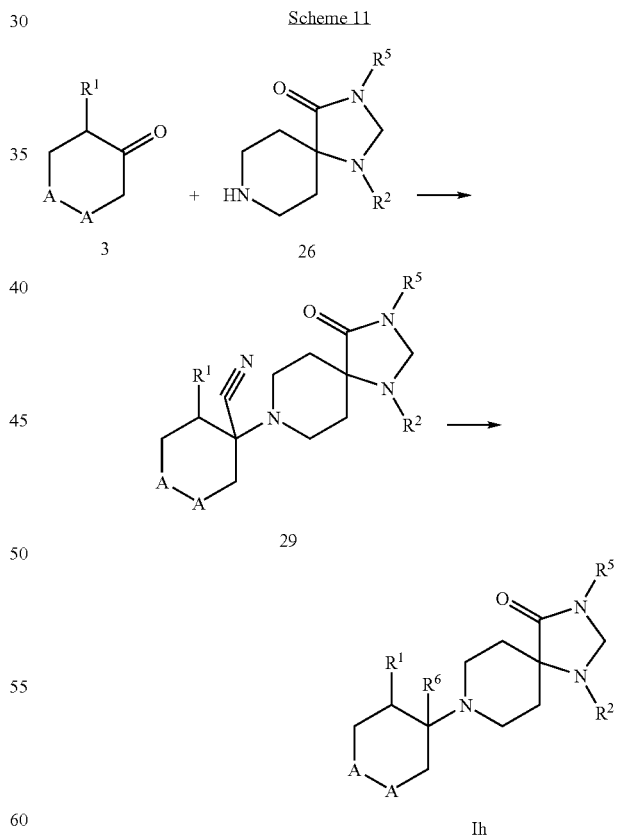

Reaction of compounds of formula (3) with 1,3 disubstituted 1,3,8-triaza-spiro[4,5]decan-4-one (26) in presence of trimethylsilyl cyanide in acetic acid at 80° C. for 16 to 20 hours provides 1-(4-oxo-1,3,8-triaza-spiro[4.5]dec-8-yl)-2-aryl-cyclohexane-carbonitrile (29). Treatment of the latter with an alkyl-magnesium halide of formula $R^6MgX$ for $R^6$=lower alkyl in an ether as solvent, preferably is THF, at 0° C. to reflux temperature leads to the final product Ih.

The acid addition salts of the basic compounds of formula I may be converted to the corresponding free bases by treatment with at least a stoichiometric equivalent of a suitable base such as sodium or potassium hydroxide, potassium carbonate, sodium bicarbonate, ammonia, and the like.

The compounds of formula I and their pharmaceutically usable addition salts possess valuable pharmacological properties. Specifically, it has been found that the compounds of the present invention are good inhibitors of the glycine transporter 1 (GlyT-1). The compounds were investigated in accordance with the test given hereinafter.

Solutions and Materials

DMEM complete medium: Nutrient mixture F-12 (Gibco Life-technologies), fetal bovine serum (FBS) 5%, (Gibco life technologies), Penicillin/Streptomycin 1% (Gibco life technologies), Hygromycin 0.6 mg/ml (Gibco life technologies), Glutamine 1 mM Gibco life technologies)

Uptake buffer (UB): 150 mM NaCl, 10 mM Hepes-Tris, pH 7.4, 1 mM $CaCl_2$, 2.5 mM KCl, 2.5 mM $MgSO_4$, 10 mM (+) D-glucose. Flp-in™-CHO (Invitrogen Cat n° R758-07)cells stably transfected with mGlyT-1b cDNA.

Glycine uptake inhibition assay (mGlyT-1b)

On day 1 mammalian cells, (Flp-in™-CHO), transfected with mGlyT-1b cDNA, were plated at the density of 40,000 cells/well in complete F-12 medium, without hygromycin in 96-well culture plates. On day 2, the medium was aspirated, and the cells were washed twice with uptake buffer (UB). The cells were then incubated for 20 min at 22° C. with either (i) no potential competitor, (ii) 10 mM non-radioactive glycine, (iii) a concentration of a potential inhibitor. A range of concentrations of the potential inhibitor was used to generate data for calculating the concentration of inhibitor resulting in 50% of the effect (e.g. $IC_{50}$, the concentration of the competitor inhibiting glycine uptake of 50%). A solution was then immediately added containing [$^3$H]-glycine 60 nM (11–16 Ci/mmol) and 25 µM non-radioactive glycine. The plates were incubated with gentle shaking and the reaction was stopped by aspiration of the mixture and washing (three times) with ice-cold UB. The cells were lysed with scintillation liquid, shaken 3 hours and the radioactivity in the cells was counted using a scintillation counter.

As shown in the table below, preferred compounds have an $IC_{50}$<0.10 µM at GlyT-1.

| Example No. | $IC_{50}$ < 0.10 µM | Example No. | $IC_{50}$ < 0.10 µM |
| --- | --- | --- | --- |
| 1 | 0.026 | 60 | 0.049 |
| 3 | 0.004 | 61 | 0.065 |
| 8 | 0.085 | 68 | 0.073 |
| 10 | 0.023 | 75 | 0.041 |
| 11 | 0.04 | 76 | 0.05 |
| 13 | 0.067 | 77 | 0.062 |
| 17 | 0.074 | 78 | 0.086 |
| 19 | 0.027 | 87 | 0.024 |
| 22 | 0.029 | 88 | 0.06 |
| 24 | 0.067 | 89 | 0.015 |
| 51 | 0.096 | 90 | 0.043 |
| 53 | 0.034 | 91 | 0.039 |
| 54 | 0.052 | 92 | 0.099 |
| 56 | 0.065 | 94 | 0.05 |
| 57 | 0.024 | 99 | 0.058 |
| 58 | 0.025 | 100 | 0.09 |
| 59 | 0.032 | 101 | 0.056 |
| 21 | 0.066 | 74 | 0.044 |

The present invention also provides pharmaceutical compositions containing compounds of the invention or pharmaceutically acceptable salts thereof and a pharmaceutically acceptable carrier. Such pharmaceutical compositions can be in the form of tablets, coated tablets, dragées, hard and soft gelatine capsules, solutions, emulsions or suspensions. The pharmaceutical compositions also can be in the form of suppositories or injectable solutions.

pharmaceutical compositions of the invention, in addition to one or more compounds of the invention, contain a pharmaceutically acceptable carrier. Suitable pharmaceutically acceptable carriers include pharmaceutically inert, inorganic or organic carriers. Lactose, corn starch or derivatives thereof, talc, stearic acid or its salts and the like can be used, for example, as such carriers for tablets, coated tablets, dragées and hard gelatine capsules. Suitable carriers for soft gelatine capsules are, for example, vegetable oils, waxes, fats, semi-solid and liquid polyols and the like; depending on the nature of the active substance no carriers are, however, usually required in the case of soft gelatine capsules. Suitable carriers for the production of solutions and syrups are, for example, water, polyols, sucrose, invert sugar, glucose and the like. Adjuvants, such as alcohols, polyols, glycerol, vegetable oils and the like, can be used for aqueous injection solutions of water-soluble salts of compounds of the invention, but as a rule are not necessary. Suitable carriers for suppositories are, for example, natural or hardened oils, waxes, fats, semi-liquid or liquid polyols and the like.

In addition, the pharmaceutical compositions can contain preservatives, solubilizers, stabilizers, wetting agents, emulsifiers, sweeteners, colorants, flavorants, salts for varying the osmotic pressure, buffers, masking agents or antioxidants. They may also contain other therapeutically valuable substances.

The present invention also provides a method for the manufacture of pharmaceutical compositions. Such process comprises bringing one or more compounds of formula I and/or pharmaceutically acceptable acid addition salts thereof and, if desired, one or more other therapeutically valuable substances into a galenical administration form together with one or more therapeutically inert carriers.

The compounds and compositions of the present invention can be administered in a conventional manner, for example, orally, rectally, or parenterally. The pharmaceutical compositions of the invention can be administered orally, for example, in the form of tablets, coated tablets, dragées, hard and soft gelatine capsules, solutions, emulsions, or suspensions. The pharmaceutical compositions also can be administered rectally, for example, in the form of suppositories, or parenterally, for example, in the form of injection solutions.

Compounds of the present invention are selective MAO-B inhibitors. Therefore, the present invention also provides methods of treating diseases that are mediated by monoamine oxidase B. Such methods include administering a therapeutically effective amount of a compound of the invention, for example, a compound of formula I, or a pharmaceutically acceptable salt thereof, to a patient in need of such treatment. In a preferred embodiment, the invention provides a method for the treatment of Alzheimer's disease. In another preferred embodiment, the present invention provides a method for the treatment of senile dementia. In yet another embodiment, the invention provides a method for the treatment of schizophrenia. In a further embodiment, the invention provides a method for the treatment of cognitive impairment.

The compounds and compositions of the present invention can be administered in a conventional manner, for example, orally, rectally, or parenterally. The pharmaceutical compositions of the invention can be administered orally, for example, in the form of tablets, coated tablets, dragées, hard and soft gelatine capsules, solutions, emulsions or suspensions. The pharmaceutical compositions also can be administered rectally, for example, in the form of suppositories or parenterally, for example, in the form of injection solutions. The dosage can vary within wide limits and will, of course, have to be adjusted to the individual requirements in each particular case. In the case of oral administration the dosage for adults can vary from about 0.01 mg to about 1000 mg per day of a compound of general formula I or of the corresponding amount of a pharmaceutically acceptable salt thereof. The daily dosage may be administered as single dose or in divided doses and, in addition, the upper limit can also be exceeded when this is found to be indicated.

The following examples illustrate the present invention without limiting it. All temperatures are given in degree Celsius.

Procedure A

Example 1

(rac,cis)-1-Phenyl-8-(2-phenyl-cyclohexyl)-1,3,8-triaza-spiro[4.5]decan-4-one

To a solution of 10.0 g (57.4 mmol) rac-2-phenylcyclohexanone in 200 ml THF were added 13.27 g (57.4 mmol) 1-phenyl-1,3,8-triazaspiro[4.5]decan-4-one and 16.3 g (17.0 ml, 57.4 mmol) titanium(IV) tetraisopropoxide. The mixture was stirred under Argon at ambient temperature for 20 h. Then at 40–50° C./15 mbar the volatiles were distilled off and the residue dissolved in 100 ml EtOH and 20 ml THF. To this stirred solution were added under Argon 2.41 g (38.5 mmol) NaBH$_3$CN and the mixture stirred at ambient temperature for 20 h. To the reaction mixture were added 25 ml water and the resulting slurry stirred for 30 min. The slurry was filtered through a Dicalite pad which was carefully washed with EtOH. The combined filtrates were evaporated and the residue dissolved in EtOH and a small volume of CHCl$_3$ and a sat. HCl/EtOH solution added. After stirring at ambient temperature for 2 h, the precipitate was collected and the crystals washed with methanol. This solid, (rac,cis)-1-phenyl-8-(2-phenyl-cyclohexyl)-1,3,8-triaza-spiro[4.5]decan-4-one hydrochloride, was distributed between 0.1N NaOH and ethyl acetate, the organic phase washed with water to neutral pH, dried over Na$_2$SO$_4$ and evaporated. The resulting slightly yellow residue was re-crystallised from Et$_2$O: 5.97 g (rac,cis)-1-phenyl-8-(2-phenyl-cyclohexyl)-1,3,8-triaza-spiro[4.5]decan-4-one as colorless crystals: m.p. 205–208° C., MS (ISP): 390.4 MH$^+$.

Example 2

(1S,2S)-1-Phenyl-8-(2-phenyl-cyclohexyl)-1,3,8-triaza-spiro[4.5]decan-4-one

The two diasteromers of (rac,cis)-1-phenyl-8-(2-phenyl-cyclohexyl)-1,3,8-triaza-spiro[4.5]decan-4-one (Example 1) were separated by preparative HPLC on a ChiralPak AD column with iPrOH/heptane 3:97: The first peak isolated was (1S,2S)-1-phenyl-8-(2-phenyl-cyclohexyl)-1,3,8-triaza-spiro[4.5]decan-4-one (>98% purity; for elucidation of absolute stereochemistry vide infra) as colorless powder: NMR (CDCl$_3$): 2.86 m (1H, CHN$_{piperidine}$), 3.18 m (1H, CH-phenyl), 4.66 d and 4.68 d (2H, AB-system N—CH$_2$—N), 6.42 s (1H, NH), 6.79–6.86 m (3H, phenyl) and 7.17 t (1H, phenyl) and 7.25–7.30 m (4H, phenyl) and 7.51 d (2H, phenyl); MIR: 1706 cm$^{-1}$ (C=O); MS (ISP): 390.4 MH$^+$.

Elucidation of absolute stereochemistry: To a solution of 24 mg (cis)-1-phenyl-8-(2-phenyl-cyclohexyl)-1,3,8-triaza-spiro[4.5]decan-4-one (Example 2) in methanol were added 14 mg 1R-(−)-camphorsulfonic acid and the solution stirred for 10 min. at ambient temperature. The resulting salt slurry was evaporated and the residue crystallized from ethyl acetate. With the single crystal X-ray structural analysis of the 1R-(−)-camphorsulfonic acid salt the absolute configuration at the cyclohexane ring was established as 1S and 2S.

Example 3

(1R,2R)-1-Phenyl-8-(2-phenyl-cyclohexyl)-1,3,8-triaza-spiro[4.5]decan-4-one

The second peak isolated (cf. Example 2) was (1R,2R)-1-Phenyl-8-(2-phenyl-cyclohexyl)-1,3,8-triaza-spiro[4.5]decan-4-one (>95% purity) which showed identical NMR, MIR and MS as Example 2.

Example 4

(rac,cis)-1-Phenyl-8-(2-phenyl-cycloheptyl)-1,3,8-triaza-spiro[4.5]decan-4-one

A mixture of 300 mg (1.6 mmol) rac-2-phenylcycloheptanone, 387 mg (1.7 mmol) 1-phenyl-1,3,8-triazaspiro[4.5]decan-4-one and 544 mg (1.9 mmol) titanium(IV) tetraisopropoxide was heated under microwave irradiation to 200° C. for 20 min. The reaction mixture was poured onto 1N NaOH and dichloromethane. This slurry was filtered through a silica gel plug (5 g) which was washed carefully with dichloromethane. The combined organic phases were dried over Na$_2$SO$_4$, filtered and evaporated. The residue was dissolved in 2 ml EtOH, 38 mg (3.7 mmol) NaBH4 were added and the mixture was stirred at ambient temperature for 20 h. Then the reaction mixture was quenched with sat. NaHCO$_3$ solution, extracted with dichloromethane, the organic phase dried with Na$_2$SO$_4$, filtered and evaporated. The crude product (124 mg) was purified by flash-chromatography over silica gel with a hexane/AcOEt gradient. Re-crystallisation of the pure fractions provided 17 mg (rac,cis)-1-phenyl-8-(2-phenyl-cycloheptyl)-1,3,8-triaza-spiro[4.5]decan-4-one as colorless crystals: MS (ISP): 404.5 MH$^+$.

Example 5

(rac,cis)-2-Isopropyl-1-phenyl-8-(2-phenyl-cyclohexyl)-1,3,8-triaza-spiro[4.5]decan-4-one A solution of 200 mg (0.389 mmol) rac-8-(3,5-bis-trifluoromethyl-benzoyl)-2-isopropyl-1-phenyl-1,3,8-triaza-spiro[4.5]decan-4-one in 2 ml THF/MeOH 1:1 was treated with 1 ml water and 196 mg (4.67 mmol) LiOH.H$_2$O. The mixture was warmed to 50° C. and stirred for 5 hours. The mixture is diluted with dichloromethane and 1N NaOH, the organic phase separated, dried over Na$_2$SO$_4$, filtered and evaporated. The residue was crude rac-2-isopropyl-1-phenyl-1,3,8-triaza-spiro[4.5]decan-4-one, which was processed in the following step.

A solution of 100 mg (0.366 mmol) crude rac-2-isopropyl-1-phenyl-1,3,8-triaza-spiro[4.5]decan-4-one in 1 ml ethanol was treated with 81 mg (0.466 mmol) 2-phenyl-cyclohexanone and 133 mg (0.468 mmol) titanium tetraisopropoxide. The reaction mixture was stirred at 60° C. for 3 h, then cooled to 40° C. and stirred for 14 h. After cooling to ambient temperature, 37 mg (0.589 mmol) sodium cyanoborohydride was added and the mixture warmed to 50° C. for 1 h, then stirred at ambient temperature for 2 h. Silica gel (1g) was added to the reaction mixture and the solvent evaporated to dryness. The resulting pale orange powder was charged on a chromatographic column and eluted with a gradient of 5–30% methanol in dichloromethane. The collected fractions were evaporated and the residue was dissolved in dichloromethane and washed twice with 1N NaOH. The organic phase was dried over $Na_2SO_4$, filtered and evaporated: 58 mg (rac,cis)-2-isopropyl-1-phenyl-8-(2-phenyl-cyclohexyl)-1,3,8-triaza-spiro[4.5]decan-4-one as an off-white solid: MS (ISP): 432.4 $MH^+$.

Example 6

(rac,cis)-2-Benzyl-1-phenyl-8-(2-phenyl-cyclohexyl)-1,3,8-triaza-spiro[4.5]decan-4-one The title compound was prepared analogously to Example 5, starting from 2-benzyl-8-(3,5-bis-trifluoromethyl-benzoyl)-1-phenyl-1,3,8-triaza-spiro[4.5]decan-4-one. (rac,cis)-2-benzyl-1-phenyl-8-(2-phenyl-cyclohexyl)-1,3,8-triaza-spiro[4.5]decan-4-one is obtained as an off-white solid: MS (ISP): 480.5 $MH^+$.

Example 7

(rac,cis)-1,2-Diphenyl-8-(2-phenyl-cyclohexyl)-1,3,8-triaza-spiro[4.5]decan-4-one The title compound was prepared analogously to Example 5, starting from 8-(3,5-bis-trifluoromethyl-benzoyl)-1,2-diphenyl-1,3,8-triaza-spiro[4.5]decan-4-one. (rac,cis)-1,2-diphenyl-8-(2-phenyl-cyclohexyl)-1,3,8-triaza-spiro[4.5]decan-4-one is obtained as an off-white solid: MS (ISP): 466.6 $MH^+$.

Procedure A1 Modification of Procedure A

Example 8

(rac,cis)-1-Phenyl-8-(2-p-tolyl-cyclohexyl)-1,3,8-triaza-spiro[4.5]decan-4-one

The 2-aryl-cyclohexanones needed for the synthesis of the compounds described in the following examples were prepared from cyclohexene oxide and either an aryl-magnesium halide or an aryl-lithium reagent which provides a 2-aryl-cyclohexanol. The latter was oxidised with Dess-Martin reagent to the required 2-aryl-cyclohexanone.

rac-2-p-Tolyl-cyclohexanol

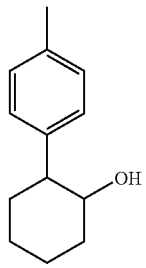

A solution of p-tolyl-magnesium bromide, prepared from 17.1 g (100 mmol) p-tolyl bromide and 2.43 g (100 mmol) magnesium, in 100 ml abs. tetrahydrofuran was cooled to −20° C. and 1 g CuBr-dimethylsulfid complex was added and the mixture stirred at −20° C. for 10 min. To this a solution of 10 ml (9.80 g, 100 mmol) cyclohexene oxide in 10 ml abs. tetrahydrofuran was added drop-wise and the reaction warmed to 0° C. at which an exothermic reaction starts. With cooling the temperature was maintained below 25° C. The reaction mixture was stirred at 0 to 5° C. for additional 2h, then quenched with saturated aqueous ammonium chloride solution and extracted with tert.-butyl methyl ether. The organic extract was washed with water, dried over $Na_2SO_4$, filtered and evaporated. The residue, 18.25 g slightly yellow crystals was re-crystallizes from n-hexane: 9.91 g rac-2-p-tolyl-cyclohexanol as colorless crystals: m.p. 72.5–73° C., MS (EI): 190.1 $M^+$.

rac-2-p-Tolyl-cyclohexanone

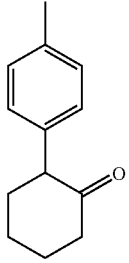

To a solution of 3.00 g (15.8 mmol) rac-2-p-tolyl-cyclohexanol in 60 ml dichloromethane were added drop-wise 51.84 g (18.3 mmol) of a 15% solution of Dess-Martin periodinane [1,1,1-tris(acetyloxy)-1,1-dihydro-1,2-benziodoxol-3-(1H)-one] in dichloromethane, and then drop-wise a solution of 300 µl water in 300 ml dichloromethane within 30 min. The resulting solution was stirred for further 30 min. at ambient temperature. Then the reaction mixture was diluted with 350 ml tert.-butyl methyl ether and evaporated to a quarter of the initial volume. The residue was diluted with 800 ml tert.-butyl methyl ether, washed with a total of 600 ml of a 1:1 mixture of saturated $NaHCO_3$ solution and a 10% $Na_2S_2O_3$ solution and with brine. The combined aqueous extracts were re-extracted with tert.-butyl methyl ether. The combined organic extracts were washed with brine, died over $Na_2SO_4$, filtered and evaporated. The residue was purified by flash-chromatography on silica gel with dichloromethane as eluent: 2.39 g rac-2-p-tolyl-cydohexanone as colorless powder: MS (ISP): 189.3 $MH^+$.

(rac,cis)-1-Phenyl-8-(2-p-tolyl-cyclohexyl)-1,3,8-triaza-spiro[4.5]decan-4-one

To a solution of 350 mg (18.6 mmol) rac-2-p-tolyl-cyclohexanone and 452 mg (19.5 mmol) 1-phenyl-1,2,8-triazaspiro[4.5]decan-4-one in 10 ml EtOH were added dropwise 634 mg (0.66 ml, 22.3 mmol) titanium(IV) tetraisopropoxide and the mixture heated to reflux for 7 h. Then the reaction mixture was cooled to ambient temperature, 165 mg $NaBH_4$ added portion wise and stirred for 16 h at ambient temperature. The slurry was filtered over a Dicalite pad, which was carefully washed with EtOH, the filtrate evaporated and the residue taken up in dichloromethane and 1N NaOH and stirred for 20 min. The organic phase was separated, washed with brine, dried with $Na_2SO_4$ and evaporated. The resulting crude product was purified by flash-chromatography on silica gel with dichloromethane/methanol/conc. ammonia 140:10:1 as eluent. Re-crystallisation of the pure fractions from ethyl acetate provided 110 mg (rac,cis)-1-phenyl-8-(2-p-tolyl-cyclohexyl)-1,3,8-triaza-spiro[4.5]decan-4-one as colorless solid: m.p. 174–176° C., MS (ISP): 404.5 $MH^+$.

In analogy to Example 8 the following spiropiperidines of Example 9–39 were prepared from the given starting material that was commercially available, described in the literature or prepared in analogy to the procedure provided for the synthesis of rac-2-p-tolyl-cyclohexanone.

Example 9

(rac,cis)-8-[2-(4-Methoxy-phenyl)-cyclohexyl]-1-phenyl-1,3,8-triaza-spiro[4.5]decan-4-one 2-(4-Methoxy-phenyl)-cyclohexanol

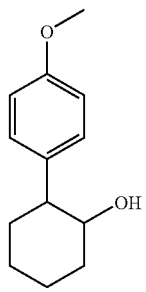

Colorless crystalls: MS (EI): 206.1 M⁺.

rac-2-(4-Methoxy-phenyl)-cyclohexanone

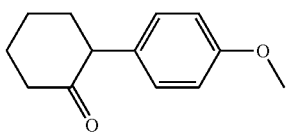

Colorless powder: MS (EI): 204.1 M⁺.

(rac,cis)-8-[2-(4-Methoxy-phenyl)-cyclohexyl]-1-phenyl-1,3,8-triaza-spiro[4.5]decan-4-one (rac,cis)-8-[2-(4-Methoxy-phenyl)-cyclohexyl]-1-phenyl-1,3,8-triaza-spiro[4.5]decan-4-one was prepared from rac-2-(4-methoxy-phenyl)-cyclohexanone: yellow oil, MS (ISP): 420.3 MH⁺.

Example 10

(rac,cis)-8-[2-(4-Fluoro-phenyl)-cyclohexyl]-1-phenyl-1,3,8-triaza-spiro[4.5]decan-4-one rac-2-(4-Fluoro-phenyl)-cyclohexanol

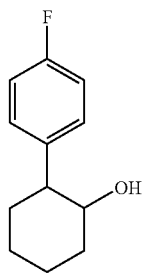

Colorless crystalls: MS (EI): 194.2 M⁺.

rac-2-(4-Fluoro-phenyl)-cyclohexanone

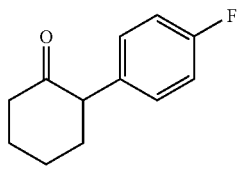

Colorless powder: MS (EI): 192.2 M⁺.

(rac,cis)-8-[2-(4-Fluoro-phenyl)-cyclohexyl]-1-phenyl-1,3,8-triaza-spiro[4.5]decan-4-one (rac,cis)-8-[2-(4-Fluoro-phenyl)-cyclohexyl]-1-phenyl-1,3,8-triaza-spiro[4.5]decan-4-one was prepared from rac-2-(4-fluoro-phenyl)-cyclohexanone: colorless crystals, m.p. 198–200° C., MS (ISP): 408.4 MH⁺.

Example 11

(rac,cis)-8-[2-(4-Chloro-phenyl)-cyclohexyl]-1-phenyl-1,3,8-triaza-spiro[4.5]decan-4-one rac-2-(4-Chloro-phenyl)-cyclohexanol

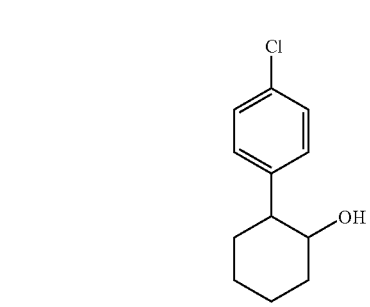

Colorless solid: m.p. 84–86° C., MS (EI): 210.2 M⁺.

rac-2-(4-Chloro-phenyl)-cyclohexanone

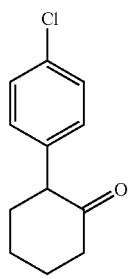

Colorless solid: m.p. 78–79° C., MS (EI): 208.0 M⁺.

(rac,cis)-8-[2-(4-Chloro-phenyl)-cyclohexyl]-1-phenyl-1,3,8-triaza-spiro[4.5]decan-4-one (rac,cis)-8-[2-(4-Chloro-phenyl)-cyclohexyl]-1-phenyl-1,3,8-triaza-spiro[4.5]decan-4-one was prepared from rac-2-(4-chloro-phenyl)-cyclohexanone: colorless crystals, m.p. 204–206° C., MS (ISP): 424.4 MH⁺.

Example 12

(rac,cis)-8-[2-(3-Chloro-phenyl)-cyclohexyl]-1-phenyl-1,3,8-triaza-spiro[4.5]decan-4-one rac-2-(3-Chloro-phenyl)-cyclohexanol

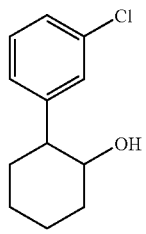

Colorless solid: m.p. 47–49° C., MS (EI): 210.1 M⁺.

rac-2-(3-Chloro-phenyl)-cyclohexanone

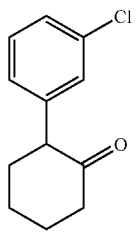

Colorless oil: MS (EI): 208.0 M⁺.

(rac,cis)-8-[2-(3-Chloro-phenyl)-cyclohexyl]-1-phenyl-1,3,8-triaza-spiro[4.5]decan-4-one (rac,cis)-8-[2-(3-Chloro-phenyl)-cyclohexyl]-1-phenyl-1,3,8-triaza-spiro[4.5]decan-4-one was prepared from rac-2-(3-chloro-phenyl)-cyclohexanone: colorless crystals, m.p. 210–212° C., MS (ISP): 424.4 MH⁺.

Example 13

(rac,cis)-8-[2-(3,4-Dichloro-phenyl)-cyclohexyl]-1-phenyl-1,3,8-triaza-spiro[4.5]decan-4-one rac-2-(3,4-Dichloro-phenyl)-cyclohexanol

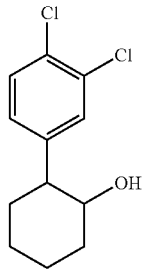

Colorless crystals: m.p. 81–82.5° C., MS (EI): 244.0 M⁺.

rac-2-(3,4-Dichloro-phenyl)-cyclohexanone

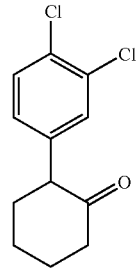

Colorless crystals: m.p. 47–49° C., MS (EI): 242.0 M⁺.

(rac,cis)-8-[2-(3,4-Dichloro-phenyl)-cyclohexyl]-1-phenyl-1,3,8-triaza-spiro[4.5]decan-4-one (rac,cis)-8-[2-(3,4-Dichloro-phenyl)-cyclohexyl]-1-phenyl-1,3,8-triaza-spiro[4.5]decan-4-one was prepared from rac-2-(3,4-dichloro-phenyl)-cyclohexanone: colorless crystals, m.p. 198–200° C., MS (ISP): 458.4 MH⁺.

Example 14

(rac,cis)-8-[2-(4-Chloro-3-trifluoromethyl-phenyl)-cyclohexyl]-1-phenyl-1,3,8-triaza-spiro[4.5]decan-4-one rac-2-(4-Chloro-3-trifluoromethyl-phenyl)-cyclohexanol

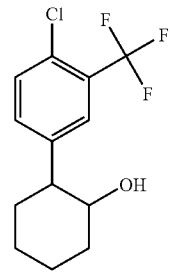

Colorless solid: m.p. 73–74° C., MS (EI): 278.0 M⁺.

rac-2-(4-Chloro-3-trifluoromethyl-phenyl)-cyclohexanone

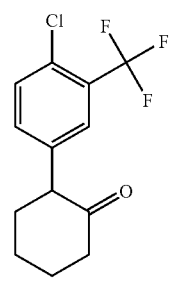

Light yellow oil: MS (EI): 276.0 M⁺.

(rac,cis)-8-[2-(4-Chloro-3-trifluoromethyl-phenyl)-cyclohexyl]-1-phenyl-1,3,8-triaza-spiro[4.5]decan-4-one (rac,cis)-8-[2-(4-Chloro-3-trifluoromethyl-phenyl)-cyclohexyl]-1-phenyl-1,3,8-triaza-spiro[4.5]decan-4-one was prepared from rac-2-(4-chloro-3-trifluoromethyl-phenyl)-cyclohexanone: colorless crystals, MS (ISP): 492.2 MH⁺.

Example 15

(rac,cis)-1-Phenyl-8-(2-o-tolyl-cyclohexyl)-1,3,8-triaza-spiro[4.5]decan-4-one rac-2-o-tolyl-cyclohexanone

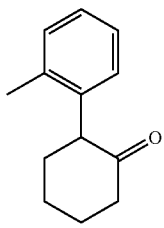

(rac,cis)-1-Phenyl-8-(2-o-tolyl-cyclohexyl)-1,3,8-triaza-spiro[4.5]decan-4-one
(rac,cis)-1-Phenyl-8-(2-o-tolyl-cyclohexyl)-1,3,8-triaza-spiro[4.5]decan-4-one was prepared from rac-2-o-tolyl-cyclohexanone: slightly yellow crystals, MS (ISP): 404.4 MH⁺.

Example 16

(rac,cis)-1-Phenyl-8-(2-pyridin-2-yl-cyclohexyl)-1,3,8-triaza-spiro[4.5]decan-4-one 2-Pyridin-2-yl-cyclohexanone

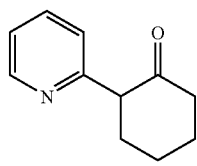

(rac,cis)-1-Phenyl-8-(2-pyridin-2-yl-cyclohexyl)-1,3,8-triaza-spiro[4.5]decan-4-one
(rac,cis)-1-Phenyl-8-(2-pyridin-2-yl-cyclohexyl)-1,3,8-triaza-spiro[4.5]decan-4-one was prepared from 2-pyridin-2-yl-cyclohexanone: off-white solid, MS(ISP): 391.2 MH⁺.

Example 17

(rac,cis)-8-[2-(4-Chloro-phenyl)-cyclohexyl]-1-(4-fluoro-phenyl)-1,3,8-triaza-spiro[4.5]decan-4-one 1-(4-fluoro-phenyl)-1,3,8-triaza-spiro[4.5]decan-4-one

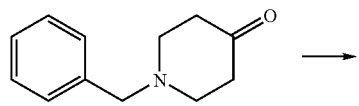

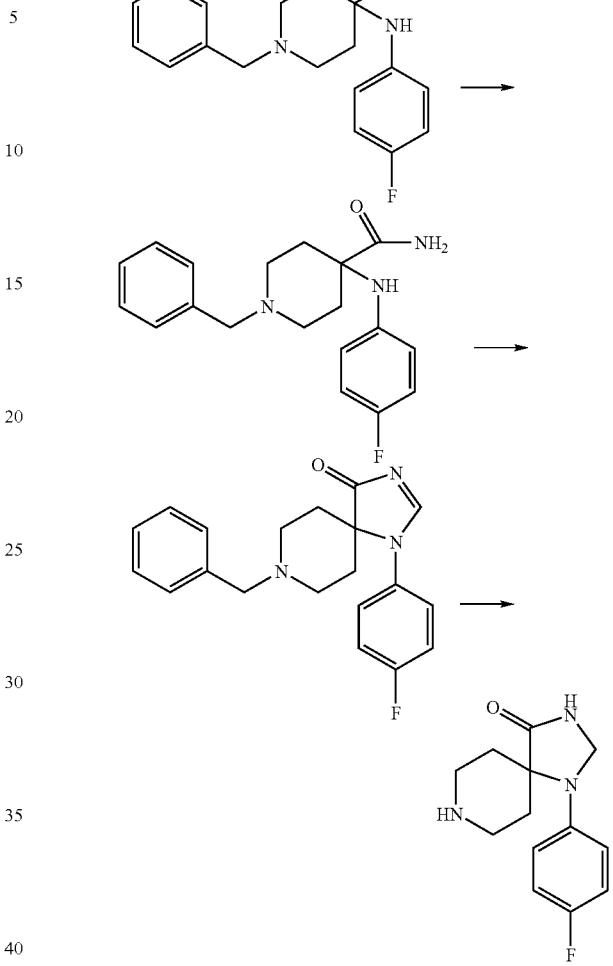

a) 1-Benzyl-4-(4-fluoro-phenylamino)-piperidine-4-carbonitrile

A mixture of 120 g (634 mmol) 1-benzyl-4-piperidone, 77.5 g (697 mmol) 4-fluoroaniline and 62.9 g (634 mmol) trimethylsilyl cyanide in 400 ml acetic acid was stirred at ambient temperature for 18 h. The reaction mixture was poured onto 500 g ice, pH is adjusted to 9 by addition of 5N NaOH and the aqueous mixture extracted with dichloromethane. The combined organic extracts were washed with brine, dried over Na₂SO₄, filtered and evaporated. The crystalline residue was re-crystallised from Et₂O: 152 g 1-benzyl-4-(4-fluoro-phenylamino)-piperidine-4-carbonitrile as colorless crystals: MS (ISP): 310.1 MH⁺.

b) 1-Benzyl-4-(4-fluoro-phenylamino)-piperidine-4-carboxylic acid amide

To 500 ml 90% sulfuric acid were slowly added at 0° C. 152 g (493 mmol) 1-benzyl-4-(4-fluoro-phenylamino)-piperidine-4-carbonitrile. The mixture was stirred at ambient temperature for 16 h, then cooled to 0° C., diluted with 200 ml water, pH was adjusted to 9 by addition of 5N NaOH and the aqueous mixture extracted with dichloromethane. The combined organic extracts were washed with brine, dried over Na₂SO₄, filtered and evaporated: 155 g 1-benzyl-4-(4-fluoro-phenylamino)-piperidine-4-carboxylic acid amide as light brown crystals: MS (ISP): 328.3 MH⁺.

c) 8-Benzyl-1-(4-fluoro-phenyl)-1,3,8-triaza-spiro[4.5]dec-2-en-4-one

A solution of 155 g (473 mmol) 1-benzyl-4-(4-fluoro-phenylamino)-piperidine-4-carboxylic acid amide in 200 ml triethyl orthoformate and 100 ml acetic acid was irradiated by microwaves in a sealed reactor to 150° C. for 10 min. and then to 200° C. for further 10 min. The reaction mixture was diluted with water, made alkaline with conc. ammonia, and extracted with dichloromethane. The combined organic extracts were washed with brine, dried over $Na_2SO_4$, filtered and evaporated. The residue was crystallised from $Et_2O$: 85 g 8-benzyl-1-(4-fluoro-phenyl)-1,3,8-triaza-spiro[4.5]dec-2-en-4-one: light brown crystals.

d) 1-(4-fluoro-phenyl)-1,3,8-triaza-spiro[4.5]decan-4-one

To a solution of 81 g 8-benzyl-1-(4-fluoro-phenyl)-1,3,8-triaza-spiro[4.5]dec-2-en-4-one in 960 ml methanol and 24 ml acetic acid were added 21.2 g 10% Pd on charcoal and stirred for 16 h under a hydrogen atmosphere at ambient temperature. The reaction mixture was filtered, concentrated, diluted with 100 ml water, made alkaline with sat $NaHCO_3$ solution and extracted with dichloromethane. The combined organic extracts were washed with brine, dried over $Na_2SO_4$, filtered and evaporated. The residue, 23 g crude product, was crystallised from AcOEt: 6.6 g 1-(4-fluoro-phenyl)-1,3,8-triaza-spiro[4.5]decan-4-one as colorless crystals: MS (ISP): 250.2 $MH^+$.

(rac,cis)-8-[2-(4-Chloro-phenyl)-cyclohexyl]-1-(4-fluoro-phenyl)-1,3,8-triaza-spiro[4.5]decan-4-one (rac,cis)-8-[2-(4-Chloro-phenyl)-cyclohexyl]-1-(4-fluoro-phenyl)-1,3,8-triaza-spiro[4.5]decan-4-one was prepared from 1-(4-fluoro-phenyl)-1,3,8-triaza-spiro[4.5]decan-4-one and rac-2-(4-chloro-phenyl)-cyclohexanone: colorless gum, MS (ISP): 442.4 $MH^+$.

Example 18

(rac,cis)-1-(4-Fluoro-phenyl)-8-(2-phenyl-cyclohexyl)-1,3,8-triaza-spiro[4.5]decan-4-one (rac,cis)-1-(4-Fluoro-phenyl)-8-(2-phenyl-cyclohexyl)-1,3,8-triaza-spiro[4.5]decan-4-one was prepared from 1-(4-fluoro-phenyl)-1,3,8-triaza-spiro[4.5]decan-4-one (Example 17d) and rac-2-(phenyl)-cyclohexanone: colorless solid, MS (ISP): 406.3 $[M-H]^+$.

Example 19

(rac,cis)-1-(4-Chloro-phenyl)-8-(2-phenyl-cyclohexyl)-1,3,8-triaza-spiro[4.5]decan-4-one a) 1-(4-Chloro-phenyl)-1,3,8-triaza-spiro[4.5]decan-4-one

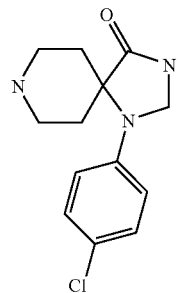

To a mixture of 1.5 g (2.97 mmol) 8-(3,5-bis-trifluoromethyl-benzoyl)-1-(4-chloro-phenyl)-1,3,8-triaza-spiro[4.5]decan-4-one in 4.5 ml THF, 4.5 ml water and 4.5 ml methanol were added 0.85 g (35.6 mmol) powdered LiOH. The reaction mixture was stirred at ambient temperature for 48 hours. The solvent was removed in vacuo. The residue was stirred in water. The resulting solid was filtered, washed with water and dried to provide the title compound (0.55 g) as a colorless solid; MS (ISP): 266.1 $MH^+$.

b) (rac,cis)-1-(4-Chloro-phenyl)-8-(2-phenyl-cyclohexyl)-1,3,8-triaza-spiro[4.5]decan-4-one (rac,cis)-1-(4-Chloro-phenyl)-8-(2-phenyl-cyclohexyl)-1,3,8-triaza-spiro[4.5]decan-4-one was prepared from (4-chloro-phenyl)-1,3,8-triaza-spiro[4.5]decan-4-one and rac-2-(phenyl)-cyclohexanone: colorless solid, MS (ISP): 424.4 $MH^+$.

Example 20

(rac,cis)-8-(2-Phenyl-cyclohexyl)-1-p-tolyl-1,3,8-triaza-spiro[4.5]decan-4-one (rac,cis)-8-(2-Phenyl-cyclohexyl)-1-p-tolyl-1,3,8-triaza-spiro[4.5]decan-4-one was prepared from 1-p-tolyl-1,3,8-triaza-spiro[4.5]decan-4-one (EP921125) and rac-2-(phenyl)-cyclohexanone: colorless solid, MS (ISP): 404.5 $MH^+$.

Example 21

(rac,cis)-1-(4-Methoxy-phenyl)-8-(2-phenyl-cyclohexyl)-1,3,8-triaza-spiro[4.5]decan-4-one a) 1-(4-Methoxy-phenyl)-1,3,8-triaza-spiro[4.5]decan-4-one

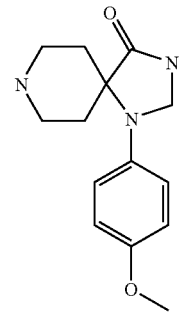

This compound was prepared from 1-benzyl-4-piperidone and 4-methoxy-phenyl amine in analogy of the procedure described for the synthesis of 1-(4-fluoro-phenyl)-1,3,8-triaza-spiro[4.5]decan-4-one. 1-(4-Methoxy-phenyl)-1,3,8-triaza-spiro[4.5]decan-4-one was obtained as colorless solid: MS (ISP): 262.1 $MH^+$.

b) (rac,cis)-1-(4-Methoxy-phenyl)-8-(2-phenyl-cyclohexyl)-1,3,8-triaza-spiro[4.5]decan-4-one (rac,cis)-1-(4-Methoxy-phenyl)-8-(2-phenyl-cyclohexyl)-1,3,8-triaza-spiro[4.5]decan-4-one was prepared from 1-(4-methoxy-phenyl)-1,3,8-triaza-spiro[4.5]decan-4-one and rac-2-(phenyl)-cyclohexanone: colorless solid, MS (ISP): 420.4 $MH^+$.

Example 22

(rac,cis)-1-(4-Fluoro-phenyl)-8-(2-p-tolyl-cyclohexyl)-1,3,8-triaza-spiro[4.5]decan-4-one (rac,cis)-1-(4-Fluoro-phenyl)-8-(2-p-tolyl-cyclohexyl)-1,3,8-triaza-spiro[4.5]decan-4-one was prepared from 1-(4- fluoro-phenyl)-1,3,8-triaza-spiro[4.5]decan-4-one and rac-2-p-tolyl-cyclohexanone: colorless crystals, MS (ISP): 422.5 MH+.

Example 23

(rac,cis)-1-(4-Fluoro-phenyl)-8-[2-(4-methoxy-phenyl)-cyclohexyl]-1,3,8-triaza-spiro[4.5]decan-4-one (rac,cis)-1-(4-Fluoro-phenyl)-8-[2-(4-methoxy-phenyl)-cyclohexyl]-1,3,8-triaza-spiro[4.5]decan-4-one was prepared from 1-(4-fluoro-phenyl)-1,3,8-triaza-spiro[4.5]decan-4-one and rac-2-(4-methoxy-phenyl)-cyclohexanone: colorless gum, MS (ISP): 438.5 MH+, 455.6 (M+NH$_4$)+.

Example 24

(rac,cis)-1-(4-Fluoro-phenyl)-8-[2-(4-fluoro-phenyl)-cyclohexyl]-1,3,8-triaza-spiro[4.5]decan-4-one (rac,cis)-1-(4-Fluoro-phenyl)-8-[2-(4-fluoro-phenyl)-cyclohexyl]-1,3,8-triaza-spiro[4.5]decan-4-one was prepared from 1-(4-fluoro-phenyl)-1,3,8-triaza-spiro[4.5]decan-4-one and rac-2-(4-fluoro-phenyl)-cyclohexanone: colorless powder, MS (ISP): 426.3 MH+.

Example 25

(rac,cis)-8-[2-(3,5-Dimethyl-phenyl)-cyclohexyl]-1-(4-fluoro-phenyl)-1,3,8-triaza-spiro[4.5]decan-4-one rac-2-(3,5-Dimethyl-phenyl)-cyclohexanol

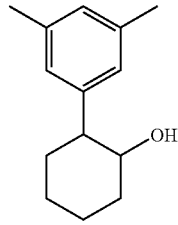

Colorless crystals: m.p. 51–51.5° C., MS (EI): 204.2 M+.

rac-2-(3,5-Dimethyl-phenyl)-cylohexanone

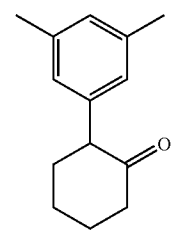

Off-white crystals: m.p. 55–56.5° C., GC/LC-MS (EI): 202 M+.

(rac,cis)-8-[2-(3,5-Dimethyl-phenyl)-cyclohexyl]-1-(4-fluoro-phenyl)-1,3,8-triaza-spiro[4.5]decan-4-one (rac,cis)-8-[2-(3,5-Dimethyl-phenyl)-cyclohexyl]-1-(4-fluoro-phenyl)-1,3,8-triaza-spiro[4.5]decan-4-one was prepared from 1-(4-fluoro-phenyl)-1,3,8-triaza-spiro[4.5]decan-4-one and rac-2-(3,5-dimethyl-phenyl)-cyclohexanone: colorless powder, MS (ISP): 436.5 MH+.

Example 26

(rac,cis)-8-[2-(3,5-Difluoro-phenyl)-cyclohexyl]-1-(4-fluoro-phenyl)-1,3,8-triaza-spiro[4.5]decan-4-one rac-2-(3,5-Difluoro-phenyl)-cyclohexanol

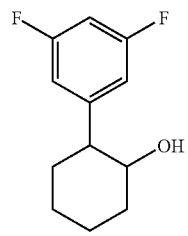

Colorless crystals: m.p. 80–82° C., MS (EI): 212.1 M+.

rac-2-(3,5-Difluoro-phenyl)-cyclohexanone

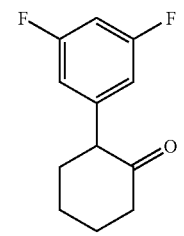

Colorless crystals: m.p. 61.5–62.5° C., MS (EI): 210.1 M+.

(rac,cis)-8-[2-(3,5-Difluoro-phenyl)-cyclohexyl]-1-(4-fluoro-phenyl)-1,3,8-triaza-spiro[4.5]decan-4-one (rac,cis)-8-[2-(3,5-Difluoro-phenyl)-cyclohexyl]-1-(4-fluoro-phenyl)-1,3,8-triaza-spiro[4.5]decan-4-one was prepared from 1-(4-fluoro-phenyl)-1,3,8-triaza-spiro[4.5]decan-4-one and rac-2-(3,5-difluoro-phenyl)-cyclohexanone: colorless crystals, MS (ISP): 444.9 MH+.

Example 27

(rac,cis)-8-[2-(2,4-Dichloro-phenyl)-cyclohexyl]-1-(4-fluoro-phenyl)-1,3,8-triaza-spiro[4.5]decan-4-one rac-2-(2,4-Dichloro-phenyl)-cylohexanol

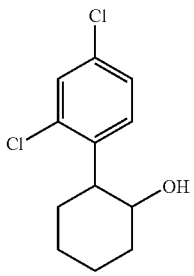

Colorless crystals: m.p. 72–72.5° C., MS (EI): 244.1 M⁺.

rac-2-(2,4-Dichloro-phenyl)-cyclohexanone

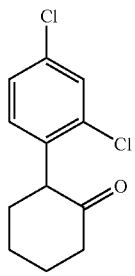

Colorless powder: m.p. 94.7–95.5° C., MS (EI): 242.1 M⁺.

(rac,cis)-8-[2-(2,4-Dichloro-phenyl)-cyclohexyl]-1-(4-fluoro-phenyl)-1,3,8-triaza-spiro[4.5]decan-4-one (rac,cis)-8-[2-(2,4-Dichloro-phenyl)-cyclohexyl]-1-(4-fluoro-phenyl)-1,3,8-triaza-spiro[4.5]decan-4-one was prepared from 1-(4-fluoro-phenyl)-1,3,8-triaza-spiro[4.5]decan-4-one and rac-2-(2,4-dichloro-phenyl)-cyclohexanone: colorless powder, MS (ISP): 476.2 MH⁺.

Example 28

(rac,cis)-8-[2-(3,4-Dichloro-phenyl)-cyclohexyl]-1-(4-fluoro-phenyl)-1,3,8-triaza-spiro[4.5]decan-4-one rac-2-(3,4-Dichloro-phenyl)-cyclohexanol

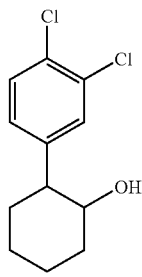

Colorless crystals: m.p. 81–82.5° C., MS (EI): 244.0 M⁺.

rac-2-(3,4-Dichloro-phenyl)-cyclohexanone

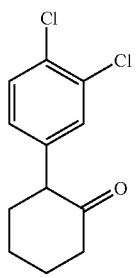

Colorless crystals: m.p. 47–49° C., MS (EI): 242.0 M⁺.

(rac,cis)-8-[2-(3,4-Dichloro-phenyl)-cylohexyl]-1-(4-fluoro-phenyl)-1,3,8-triaza-spiro[4.5]decan-4-one (rac,cis)-8-[2-(3,4-Dichloro-phenyl)-cyclohexyl]-1-(4-fluoro-phenyl)-1,3,8-triaza-spiro[4.5]decan-4-one was prepared from 1-(4-fluoro-phenyl)-1,3,8-triaza-spiro[4.5]decan-4-one and rac-2-(3,4-dichloro-phenyl)-cyclohexanone: colorless powder, MS (ISP): 476.2 MH⁺.

Example 29

(rac,cis)-8-[2-(3,5-Dichloro-phenyl)-cyclohexyl]-1-(4-fluoro-phenyl)-1,3,8-triaza-spiro[4.5]decan-4-one rac-2-(3,5-Dichloro-phenyl)-cyclohexanol

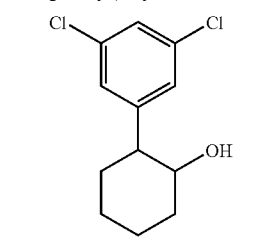

Colorless crystals: m.p. 90–90.3° C., MS (EI): 244.1 M⁺.

rac-2-(3,5-Dichloro-phenyl)-cyclohexanone

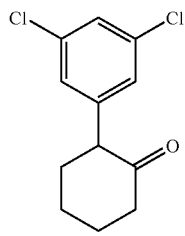

Colorless crystals: m.p. 76–77° C., MS (EI): 242.1 M⁺.

rac,cis)-8-[2-(3,5-Dichloro-phenyl)-cyclohexyl]-1-(4-fluoro-phenyl)-1,3,8-triaza-spiro[4.5]decan-4-one (rac,cis)-8-[2-(3,5-Dichloro-phenyl)-cyclohexyl]-1-(4-fluoro-phenyl)-1,3,8-triaza-spiro[4.5]decan-4-one was prepared from 1-(4-fluoro-phenyl)-1,3,8-triaza-spiro[4.5]decan-4-one and rac-2-(3,5-Dichloro-phenyl)-cyclohexanone: colorless powder, MS (ISP): 476.2 MH⁺.

Example 30

(rac,cis)-1-(4-Fluoro-phenyl)-8-[2-(3-fluoro-5-trifluoromethyl-phenyl)-cyclohexyl]-1,3,8-triaza-spiro[4.5]decan-4-one rac-2-(3-Fluoro-5-trifluoromethyl-phenyl)-cyclohexanol

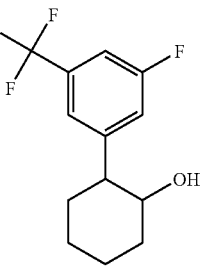

A stirred solution of 8.00 g (32.9 mmol) 3-fluoro-5-trifluoromethyl-bromo-benzene in 40 ml Et₂O under nitrogen was cooled to −78° C. and drop-wise 20.56 ml (32.9 mmol) of a 1.6 M butyl lithium solution in hexane were added. The reaction was strongly exothermic and the temperature was kept below −70° C. Then after 30 min. at −78° C. 2.66 ml (2.58 g, 26.3 mmol) cyclohexene oxide were added followed by 3.75 ml (4.2 g, 29.6 mmol) boron trifluoride diethyl etherate. The latter has to be added drop-wise to keep the temperature below −70° C. The reaction mixture was stirred for 2 h at −78° C. and then quenched with 40 ml saturated aqueous $KHSO_4$ solution, warmed up to ambient temperature and extracted with tert.-butyl methyl ether. The combined organic extracts were washed with brine, dried over $Na_2SO_4$, filtered and evaporated. The crude product, 7.53 g light yellow crystals, was purified by re-crystallisation from n-heptane: 4.90 g rac-2-(3-fluoro-5-trifluoromethyl-phenyl)-cyclohexanol as colorless crystals: m.p. 76.5–77.4° C., MS (EI): 262.1 $M^+$.

rac-2-(3-Fluoro-5-trifluoromethyl-phenyl)-cyclohexanone

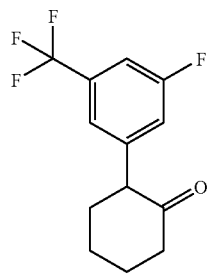

Oxidation with Dess-Martin periodinane as described for rac-2-p-tolyl-cyclohexanone provided rac-2-(3-fluoro-5-trifluoromethyl-phenyl)-cyclohexanone as light yellow crystals: m.p. 56.5–58.5° C., MS (EI): 260.1 $M^+$.

(rac,cis)-1-(4-Fluoro-phenyl)-8-[2-(3-fluoro-5-trifluoromethyl-phenyl)-cyclohexyl]-1,3,8-triaza-spiro[4.5]decan-4-one (rac,cis)-1-(4-Fluoro-phenyl)-8-[2-(3-fluoro-5-trifluoromethyl-phenyl)-cyclohexyl]-1,3,8-triaza-spiro[4.5]decan-4-one was prepared from 1-(4-fluoro-phenyl)-1.3.8-triaza-spiro[4.5]decan-4-one and rac-2-(3-fluoro-5-trifluoromethyl-phenyl)-cyclohexanone: colorless powder, MS (ISP): 495.0 $MH^+$.

Example 31

(rac,cis)-8-[2-(4-Chloro-phenyl)-cyclohexyl]-1-propyl-1,3,8-triaza-spiro[4.5]decan-4-one 1-Propyl-1,3,8-triaza-spiro[4.5]decan-4-one

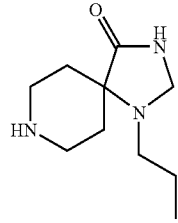

This compound was prepared from 1-benzyl-4-piperidone and propylamine in analogy of the procedure described for the synthesis of 1-(4-fluoro-phenyl)-1,3,8-triaza-spiro[4.5]decan-4-one. 1-Propyl-1,3,8-triaza-spiro[4.5]decan-4-one was obtained as colorless powder: MS (ISP): 198.1 $MH^+$.

(rac,cis)-8-[2-(4-Chloro-phenyl)-cyclohexyl]-1-propyl-1,3,8-triaza-spiro[4.5]decan-4-one (rac,cis)-8-[2-(4-Chloro-phenyl)-cyclohexyl]-1-propyl-1,3,8-triaza-spiro[4.5]decan-4-one was prepared from 1-propyl-1,3,8-triaza-spiro[4.5]decan-4-one and rac-2-(4-chloro-phenyl)-cyclohexanone: colorless powder, MS (ISP): 390.3 $MH^+$.

Example 32

(rac,cis)-8-[2-(3-Chloro-phenyl)-cyclohexyl]-1-propyl-1,3,8-triaza-spiro[4.5]decan-4-one (rac,cis)-8-[2-(3-Chloro-phenyl)-cyclohexyl]-1-propyl-1,3,8-triaza-spiro[4.5]decan-4-one was prepared from 1-propyl-1,3,8-triaza-spiro[4.5]decan-4-one and rac-2-(3-chloro-phenyl)-cyclohexanone: colorless powder, MS (ISP): 390.3 $MH^+$.

Example 33

(rac,cis)-1-Propyl-8-(2-p-tolyl-cyclohexyl)-1,3,8-triaza-spiro[4.5]decan-4-one (rac,cis)-1-Propyl-8-(2-p-tolyl-cyclohexyl)-1,3,8-triaza-spiro[4.5]decan-4-one was prepared from 1-propyl-1,3,8-triaza-spiro[4.5]decan-4-one and rac-2-p-tolyl-cyclohexanone: colorless powder, MS (ISP): 370.3 $MH^+$.

Example 34

(rac,cis)-8-[2-(4-Fluoro-phenyl)-cyclohexyl]-1-propyl-1,3,8-triaza-spiro[4.5]decan-4-one (rac,cis)-8-[2-(4-Fluoro-phenyl)-cyclohexyl]-1-propyl-1,3,8-triaza-spiro[4.5]decan-4-one was prepared from 1-propyl-1,3,8-triaza-spiro[4.5]decan-4-one and rac-2-(4-fluoro-phenyl)-cyclohexanone: colorless powder, MS (ISP): 374.4 $MH^+$.

Example 35

(rac,cis)-8-[$^2$-(3,5-Dimethyl-phenyl)-cyclohexyl]-1-propyl-1,3,8-triaza-spiro[4.5]decan-4-one (rac,cis)-8-[2-(3,5-Dimethyl-phenyl)-cyclohexyl]-1-propyl-1,3,8-triaza-spiro[4.5]decan-4-one was prepared from 1-propyl-1,3,8-triaza-spiro[4.5]decan-4-one and rac-2-(3,5-dimethyl-phenyl)-cyclohexanone: colorless powder, MS (ISP): 384.5 $MH^+$.

Example 36

(rac,cis)-8-[2-(3,5-Difluoro-phenyl)-cyclohexyl]-1-propyl-1,3,8-triaza-spiro[4.5]decan-4-one (rac,cis)-8-[2-(3,5-Difluoro-phenyl)-cyclohexyl]-1-propyl-1,3,8-triaza-spiro[4.5]decan-4-one was prepared from 1-propyl-1,3,8-triaza-spiro[4.5]decan-4-one and rac-2-(3,5-difluoro-phenyl)-cyclohexanone: colorless gum, MS (ISP): 393.0 $MH^+$.

Example 37

(rac,cis)-8-[2-(3,4-Dichloro-phenyl)-cyclohexyl]-1-propyl-1,3,8-triaza-spiro[4.5]decan-4-one (rac,cis)-8-[2-(3,4-Dichloro-phenyl)-cyclohexyl]-1-propyl-1,3,8-triaza-spiro[4.5]decan-4-one was prepared from 1-propyl-1,3,8-triaza-spiro[4.5]decan-4-one and rac-2-(3,4-dichloro-phenyl)-cyclohexanone: colorless powder, MS (ISP): 424.5 $MH^+$.

Example 38

(rac,cis)-8-[2-(3,5-Dichloro-phenyl)-cyclohexyl]-1-propyl-1,3,8-triaza-spiro[4.5]decan-4-one (rac,cis)-8-[2-(3,5-Dichloro-phenyl)-cyclohexyl]-1-propyl-1,3,8-triaza-spiro[4.5]decan-4-one was prepared from 1-propyl-1,3,8-triaza-spiro[4.5]decan-4-one and rac-2-(3,5-dichloro-phenyl)-cyclohexanone: colorless powder, MS (ISP): 424.3 MH$^+$.

Example 39

(rac,cis)-8-[2-(3,5-Bis-trifluoromethyl-phenyl)-cyclohexyl]-1-propyl-1,3,8-triaza-spiro[4.5]decan-4-one rac-2-(3,5-Bis-trifluoromethyl-phenyl)-cyclohexanol

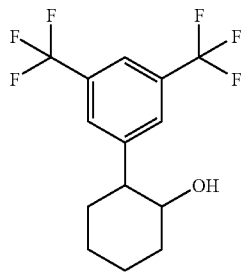

Light yellow viscous oil: MS (EI): 312.1 M$^+$.

rac-2-(3,5-Bis-trifluoromethyl-phenyl)-cyclohexanone

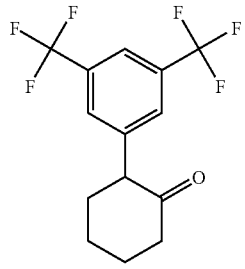

Colorless crystals: m.p. 48–50° C., MS (EI): 310.1 M$^+$.

(rac,cis)-8-[2-(3,5-Bis-trifluoromethyl-phenyl)-cyclohexyl]-1-propyl-1,3,8-triaza-spiro[4.5]decan-4-one (rac,cis)-8-[2-(3,5-Bis-trifluoromethyl-phenyl)-cyclohexyl]-1-propyl-1,3,8-triaza-spiro[4.5]decan-4-one was prepared from 1-propyl-1,3,8-triaza-spiro[4.5]decan-4-one and rac-2-(3,5-bis-trifluoromethyl-phenyl)-cyclohexanone: colorless powder, MS (ISN): 490.4 (M-H)$^-$; MS (ISP): 493.1 MH$^+$.

Procedure B

Example 40

Preparation of (rac,cis)-1-Ethyl-8-(2-phenyl-cyclohexyl)-1,3,8-triaza-spiro[4.5]decan-4-one a) (rac,cis)-8-(2-Phenyl-cyclohexyl)-1,4-dioxa-8-aza-spiro[4,5]decane To a solution of 46.0 g 2-phenyl-cyclohexanone (264 mmol) and 31.5 g (220 mmol) 1,4-dioxa-8-aza-spiro[4,5]decane in 380 ml toluene were added 4.18 g (22 mmol) pTsOH.H$_2$O and the mixture heated to reflux in an apparatus equipped with a Dean-Stark trap for 24 h. Then the reaction mixture was evaporated and the resulting crude enamine dissolved in 900 ml 1,2-dichloroethane and 8 ml acetic acid. To this solution were added in portion 69.0 g (308 mmol) sodium triacetoxyborohydride. After a total reaction time of 2.5 h the reaction mixture was treated with 250 ml 2N NaOH and extracted with dichloromethane. The combined organic extracts were washed with brine, dried over MgSO$_4$, filtered and evaporated. Purification of the crude product over a silica gel plug (10:1) with n-heptane/AcOEt 10:1 then n-heptane/AcOEt 9:1 and finally AcOEt as eluent provided 44.85 g (68%) (rac,cis)-8-(2-phenyl-cyclohexyl)-1,4-dioxa-8-aza-spiro[4,5]decane as a yellow oil. MS (ISP): 302.4 MH$^+$.

b) (rac,cis)-1-(2-Phenyl-cyclohexyl)-piperidin-4-one

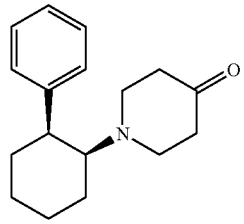

A solution of 44.85 g (rac,cis)-8-(2-phenyl-cyclohexyl)-1,4-dioxa-8-aza-spiro[4,5]decane in 100 ml methanol and 445 ml 6N HCl was heated to reflux for 16 h. Then the reaction mixture was made basic with solid Na$_2$CO$_3$, extracted with dichloromethane, dried over Na$_2$SO$_4$, filtered and evaporated. The crude product was purified by flash chromatography over silica gel with n-heptane as eluent: 28.85 g (rac,cis)-1-(2-phenyl-cyclohexyl)-piperidin-4-one as sticky yellow oil: MS (ISP): 258.3 MH$^+$.

c) (rac,cis)-4-Ethylamino-1-(2-phenyl-cyclohexyl)-piperidine-4-carboxylic acid amide

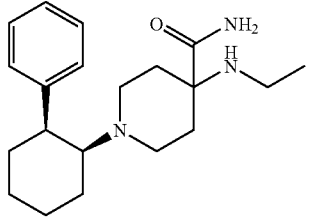

To a solution of 300 mg (1.17 mmol) (rac,cis)-1-(2-phenyl-cyclohexyl)-piperidin-4-one in 2 ml EtOH and 106 mg (1.29 mmol) ethylamine hydrochloride dissolved in 0.126 ml (1.58 mmol) 70% aqueous triethylamine solution were added portion-wise 84 mg (1.29 mmol) KCN and the suspension stirred at ambient temperature for 2.75 days. The reaction mixture was diluted with 25% aqueous ammonia and extracted with dichloromethane. The organic extracts were washed with brine, dried over Na$_2$SO$_4$, filtered and evaporated. The resulting 0.38 g (rac,cis)-4-ethylamino-1-(2-phenyl-cyclohexyl)-piperidine-4-carbonitrile, a yellow oil, were dissolved in 2.6 ml 90% H$_2$SO$_4$ and stirred at ambient temperature for 16 h. Then the mixture was poured onto iced 25% ammonia and extracted with dichloromethane. The organic phase was washed with brine, dried over Na$_2$SO$_4$, filtered and evaporated. The crude product was purified by flash-chromatography on silica gel with 2:1 AcOEt/MeOH: 0.16 (rac,cis)-4-ethylamino-1-(2-phenyl-cyclohexyl)-piperidine-4-carboxylic acid amide as light yellow oil: MS (ISP): 330.4 MH$^+$.

d) (rac,cis)-1-Ethyl-8-(2-phenyl-cyclohexyl)-1,3,8-triaza-spiro[4.5]dec-2-en-4-one

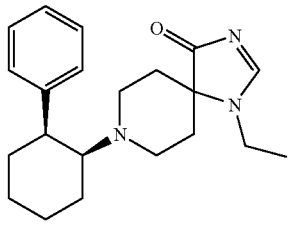

A solution of 0.16 g (4.9 mmol) 4-ethylamino-1-(2-phenyl-cyclohexyl)-piperidine-4-carboxylic acid amide, 5.5 ml (15 mmol) triethyl orthoformate and 0.5 ml acetic acid in 8.5 ml toluene were heated to reflux for 20 h. At ambient temperature the mixture was diluted with 20 ml water, made alkaline with 25% ammonia and extracted with dichloromethane. The organic extract was washed with brine, dried over $Na_2SO_4$, filtered and evaporated. The crude product was purified by preparative HPLC over a reverse phase column with a $H_2O$/MeCN gradient: 90 mg (rac,cis)-1-ethyl-8-(2-phenyl-cyclohexyl)-1,3,8-triaza-spiro[4.5]dec-2-en-4-one as light yellow oil, which was crystallised from $Et_2O$: (ISP): 340.4 $MH^+$.

This cyclization step d) could also be performed under microwave irradiation as described for examples 58–63.

e) (rac,cis)-1-Ethyl-8-(2-phenyl-cyclohexyl)-1,3,8-triaza-spiro[4.5]decan-4-one

To a solution of 90 mg (0.265 mmol) (rac,cis)-1-ethyl-8-(2-phenyl-cyclohexyl)-1,3,8-triaza-spiro[4.5]dec-2-en-4-one in 10 ml methanol were added portion-wise 16 mg (0.398 mmol) $NaBH_4$ and the mixture stirred at ambient temperature for 1 h and at 60° C. for another hour. The mixture was evaporated and the residue taken up in 20 ml dichloromethane and 20 ml 12% ammonia. The slurry was stirred at ambient temperature for 2 h, the organic phase separated and the aqueous phase extracted carefully with dichloromethane. The combined extracts were washed with brine, dried over $Na_2SO_4$, filtered and evaporated: 81.3 mg (rac,cis)-1-ethyl-8-(2-phenyl-cyclohexyl)-1,3,8-triaza-spiro[4.5]decan-4-one as colorless crystals: (ISP): 342.4 $MH^+$.

Example 41

(rac,cis)-1-Isopropyl-8-(2-phenyl-cyclohexyl)-1,3,8-triaza-spiro[4.5]decan-4-one (rac,cis)-4-Isopropylamino-1-(2-phenyl-cyclohexyl)-piperidine-4-carboxylic acid amide

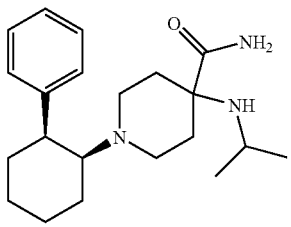

To a solution of 230 mg (0.89 mmol) (rac,cis)-1-(2-phenyl-cyclohexyl)-piperidin-4-one in 2 ml EtOH were added 94 mg (0.98 mmol) isopropyl amine hydrochloride and the mixture stirred at ambient temperature until a solution was obtained (5 min.). Then 1 ml water and 64 mg (0.98 mmol) KCN were added and the suspension stirred at ambient temperature for 24 h. The reaction mixture was poured onto iced water and extracted with dichloromethane. The organic extracts were washed with brine, dried over $Na_2SO_4$, filtered and evaporated. The resulting 245 mg (rac,cis)-4-isoproylamino-1-(2-phenyl-cyclohexyl)-piperidine-4-carbonitrile, a yellow oil, were dissolved in 1.5 ml 90% $H_2SO_4$ and stirred at ambient temperature for 20 h. Then the mixture was poured onto iced 25% ammonia and extracted with dichloromethane. The organic phase was washed with brine, dried over $Na_2SO_4$, filtered and evaporated. The crude product was purified by flash-chromatography on silica gel with 3:1 AcOEt/MeOH as eluent: 142 mg (rac,cis)-4-isopropylamino-1-(2-phenyl-cyclohexyl)-piperidine-4-carboxylic acid amide as light yellow oil: MS (ISP): 344.6 $MH^+$.

(rac,cis)-1-Isopropyl-8-(2-phenyl-cyclohexyl)-1,3,8-triaza-spiro[4.5]decan-4-one The last two steps (ring closure and reduction of imine) of the synthesis were carried out in analogy to Example 40d) and 40e) and provided (rac,cis)-1-isopropyl-8-(2-phenyl-cyclohexyl)-1,3,8-triaza-spiro[4.5]decan-4-one as colorless solid: m.p. 132–134° C., MS (ISP): 356.4 $MH^+$.

In analogy to Example 41 the following spiropiperidines of Example 42–46 were prepared from the given starting material that is either commercially available or described in the literature.

Example 42

(rac,cis)-1-Cyclohexyl-8-(2-phenyl-cyclohexyl)-1,3,8-triaza-spiro[4.5]decan-4-one

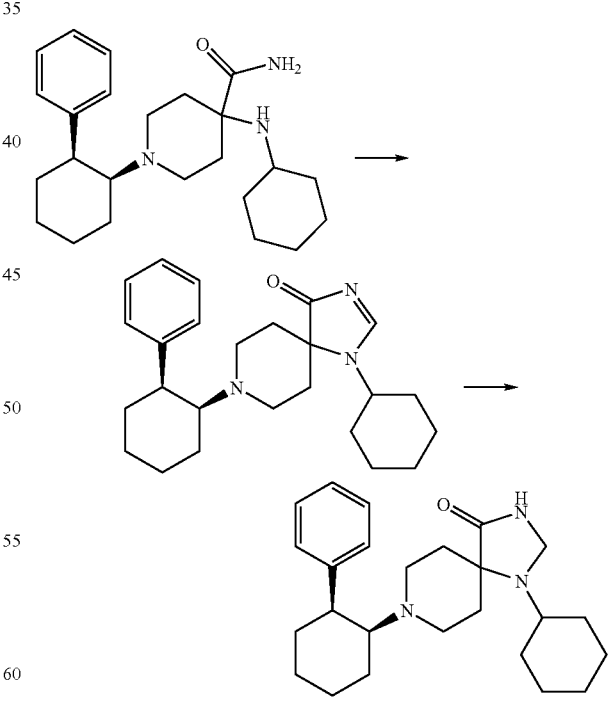

(rac,cis)-1-Cyclohexyl-8-(2-phenyl-cyclohexyl)-1,3,8-triaza-spiro[4.5]decan-4-one was prepared from (rac,cis)-1-(2-phenyl-cyclohexyl)-piperidin-4-one and cyclohexylamine hydrochloride: colorless solid, m.p. 183–185° C., MS (ISP): 396.5 $MH^+$.

Example 43

(rac,cis)-8-(2-Phenyl-cyclohexyl)-1-(3,3,3-trifluoro-propyl)-1,3,8-triaza-spiro[4.5]decan-4-one

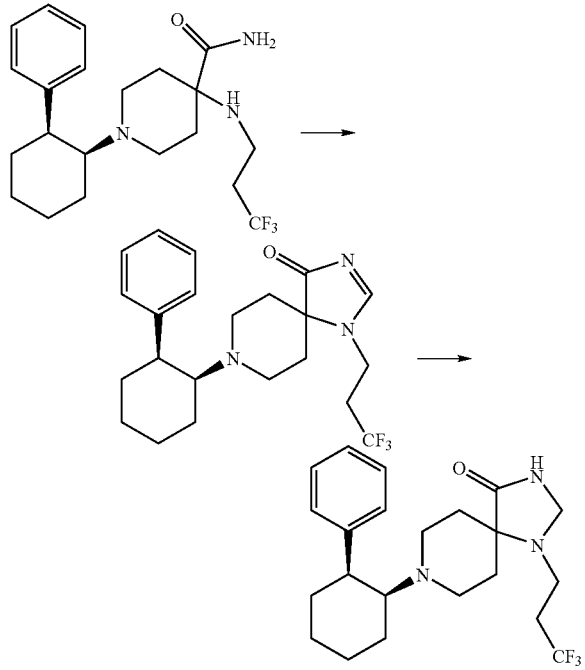

(rac,cis)-8-(2-Phenyl-cyclohexyl)-1-(3,3,3-trifluoro-propyl)-1,3,8-triaza-spiro[4.5]decan-4-one was prepared from (rac,cis)-1-(2-phenyl-cyclohexyl)-piperidin-4-one and 2,2,2-trifluoropropyl-amine hydrochloride: colorless solid, m.p. 154–156° C., MS (ISP): 410.3 MH⁺.

Example 44

(rac,cis)-1-(2-Methoxy-ethyl)-8-(2-phenyl-cyclohexyl)-1,3,8-triaza-spiro[4.5]decan-4-one (rac,cis)-1-(2-Methoxy-ethyl)-8-(2-phenyl-cyclohexyl)-1,3,8-triaza-spiro[4.5]decan-4-one was prepared from (rac,cis)-1-(2-phenyl-cyclohexyl)-piperidin-4-one and 2-methoxyethylamine hydrochloride: colorless gum, MS (ISP): 372.4 MH⁺.

Example 45

(rac,cis)-8-(2-Phenyl-cyclohexyl)-1-(2-piperidin-1-yl-ethyl)-1,3,8-triaza-spiro[4.5]decan-4-one (rac,cis)-8-(2-Phenyl-cyclohexyl)-1-(2-piperidin-1-yl-ethyl)-1,3,8-triaza-spiro[4.5]decan-4-one was prepared from (rac,cis)-1-(2-phenyl-cyclohexyl)-piperidin-4-one and 1-(2-aminoethyl)-piperidine hydrochloride: colorless gum, MS (ISP): 425.5 MH⁺, 442.5 (M+NH₄)⁺.

Example 46

(rac,cis)-1-(2-Morpholin-4-yl-ethyl)-8-(2-phenyl-cyclohexyl)-1,3,8-triaza-spiro[4.5]decan-4-one (rac,cis)-1-(2-Morpholin-4-yl-ethyl)-8-(2-phenyl-cyclohexyl)-1,3,8-triaza-spiro[4.5]decan-4-one was prepared from (rac,cis)-1-(2-phenyl-cyclohexyl)-piperidin-4-one and 1-(2-aminoethyl)-morpholine hydrochloride: colorless crystals, MS (ISP): 427.6 MH⁺.

Example 47

(rac,cis)-1-Benzyl-8-(2-phenyl-cyclohexyl)-1,3,8-triaza-spiro[4.5]decan-4-one a) (rac,cis)-4-Benzylamino-1-(2-phenyl-cyclohexyl)-piperidine-4-carbonitrile

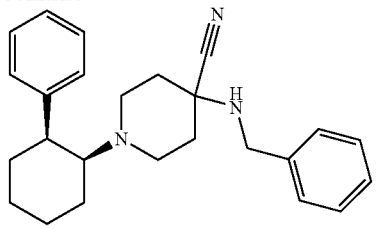

To a stirred solution of 232 mg (0.90 mmol) (rac,cis)-1-(2-phenyl-cyclohexyl)-piperidin-4-one in 4 ml acetic acid were added at ambient temperature 0.270 mg (276 ml, 2.52 mmol) benzylamine. The mixture was cooled to 0° C., then a solution of 168 mg (2.58 mmol) KCN in 0.7 ml water was added and the solution stirred at ambient temperature for 18 h. The reaction mixture was poured onto iced water, made alkaline by addition of conc. ammonia and extracted with AcOEt. The organic extracts were washed with brine, dried over Na₂SO₄, filtered and evaporated. The residue was purified by flash-chromatography on silica gel with n-hexane/AcOEt 5:1 as eluent: 270 mg (rac,cis)-4-benzylamino-1-(2-phenyl-cyclohexyl)-piperidine-4-carbonitrile as a yellow oil, MS (ISP): 374.5 MH⁺.

b) (rac,cis)-4-Benzylamino-1-(2-phenyl-cyclohexyl)-piperidine-4-carboxylic acid amide

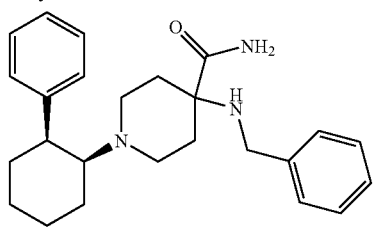

A solution of 255 mg (6083 mmol) (rac,cis)-4-benzylamino-1-(2-phenyl-cyclohexyl)-piperidine-4-carbonitrile in 1.7 ml 90% H₂SO₄ was stirred at ambient temperature for 20 h. Then the mixture was poured onto iced 12% ammonia and extracted with dichloromethane. The organic phase was washed with brine, dried over Na₂SO₄, filtered and evaporated. The crude product was purified by flash-chromatography on silica gel with AcOEt/MeOH 2:1 as eluent: 176 mg (rac,cis)-4-benzylamino-1-(2-phenyl-cyclohexyl)-piperidine-4-carboxylic acid amide as off-white amorphous solid: MS (ISP): 392.4 MH⁺.

c) (rac,cis)-1-Benzyl-8-(2-phenyl-cyclohexyl)-1,3,8-triaza-spiro[4.5]decan-4-one

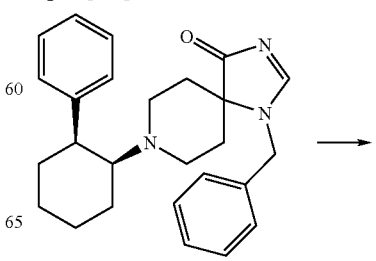

-continued

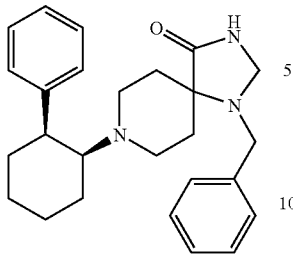

The last two steps (ring closure and reduction of imine) of the synthesis were carried out in analogy to Example 40d) and 40e) and provided (rac,cis)-1-benzyl-8-(2-phenyl-cyclohexyl)-1,3,8-triaza-spiro[4.5]decan-4-one as colorless solid: m.p. 185° C., MS (ISP): 404.6 MH+.

In analogy to Example 47 the following spiropiperidines of Example 48–57 were prepared from the given starting material that was either commercially available or described in the literature.

Example 48

(rac,cis)-8-(2-Phenyl-cyclohexyl)-1-propyl-1,3,8-triaza-spiro[4.5]decan-4-one (rac,cis)-8-(2-Phenyl-cyclohexyl)-1-propyl-1,3,8-triaza-spiro[4.5]decan-4-one was prepared from (rac,cis)-1-(2-phenyl-cyclohexyl)-piperidin-4-one and propylamine: colorless solid, MS (ISP): 356.3 MH+.

Example 49

(rac,cis)-1-Cyclopropyl-8-(2-phenyl-cyclohexyl)-1,3,8-triaza-spiro[4.5]decan-4-one (rac,cis)-1-Cyclopropyl-8-(2-phenyl-cyclohexyl)-1,3,8-triaza-spiro[4.5]decan-4-one was prepared from (rac,cis)-1-(2-phenyl-cyclohexyl)-piperidin-4-one and cyclopropylamine: colorless oil, MS (ISP): 354.3 MH+.

Example 50

(rac,cis)-1-Butyl-8-(2-phenyl-cyclohexyl)-1,3,8-triaza-spiro[4.5]decan-4-one (rac,cis)-1-Butyl-8-(2-phenyl-cyclohexyl)-1,3,8-triaza-spiro[4.5]decan-4-one was prepared from (rac,cis)-1-(2-phenyl-cyclohexyl)-piperidin-4-one and butylamine: colorless solid, MS (ISP): 370.3 MH+.

Example 51

(rac,cis)-1-Isobutyl-8-(2-phenyl-cyclohexyl)-1,3,8-triaza-spiro[4.5]decan-4-one (rac,cis)-1-Isobutyl-8-(2-phenyl-cyclohexyl)-1,3,8-triaza-spiro[4.5]decan-4-one was prepared from (rac,cis)-1-(2-phenyl-cyclohexyl)-piperidin-4-one and isobutylamine: colorless gum, MS (ISP): 370.3 MH+.

Example 52

(rac,cis)-1-Cyclobutyl-8-(2-phenyl-cyclohexyl)-1,3,8-triaza-spiro[4.5]decan-4-one (rac,cis)-1-Cyclobutyl-8-(2-phenyl-cyclohexyl)-1,3,8-triaza-spiro[4.5]decan-4-one was prepared from (rac,cis)-1-(2-phenyl-cyclohexyl)-piperidin-4-one and cyclobutylamine: colorless gum, MS (ISP): 368.2 MH+.

Example 53

(rac,cis)-1-Pentyl-8-(2-phenyl-cyclohexyl)-1,3,8-triaza-spiro[4.5]decan-4-one (rac,cis)-1-Pentyl-8-(2-phenyl-cyclohexyl)-1,3,8-triaza-spiro[4.5]decan-4-one was prepared from (rac,cis)-1-(2-phenyl-cyclohexyl)-piperidin-4-one and pentylamine: colorless gum, MS (ISP): 384.3 MH+.

Example 54

(rac,cis)-1-(3-Methyl-butyl)-8-(2-phenyl-cyclohexyl)-1,3,8-triaza-spiro[4.5]decan-4-one (rac,cis)-1-(3-Methyl-butyl)-8-(2-phenyl-cyclohexyl)-1,3,8-triaza-spiro[4.5]decan-4-one was prepared from (rac,cis)-1-(2-phenyl-cyclohexyl)-piperidin-4-one and isopentylamine: colorless gum, MS (ISP): 384.3 MH+.

Example 55

(rac,cis)-1-Cyclopentyl-8-(2-phenyl-cyclohexyl)-1,3,8-triaza-spiro[4.5]decan-4-one (rac,cis)-1-Cyclopentyl-8-(2-phenyl-cyclohexyl)-1,3,8-triaza-spiro[4.5]decan-4-one was prepared from (rac,cis)-1-(2-phenyl-cyclohexyl)-piperidin-4-one and cyclopentylamine: colorless foam, MS (ISP): 382.3 MH+.

Example 56

(rac,cis)-1-Cyclohexylmethyl-8-(2-phenyl-cyclohexyl)-1,3,8-triaza-spiro[4.5]decan-4-one (rac,cis)-1-Cyclohexylmethyl-8-(2-phenyl-cyclohexyl)-1,3,8-triaza-spiro[4.5]decan-4-one was prepared from (rac,cis)-1-(2-phenyl-cyclohexyl)-piperidin-4-one and cyclohexanemethylamine: colorless solid, MS (ISP): 410.4 MH+.

Example 57

(rac,cis)-1-Phenethyl-8-(2-phenyl-cyclohexyl)-1,3,8-triaza-spiro[4.5]decan-4-one (rac,cis)-1-Phenethyl-8-(2-phenyl-cyclohexyl)-1,3,8-triaza-spiro[4.5]decan-4-one was prepared from (rac,cis)-1-(2-phenyl-cyclohexyl)-piperidin-4-one and phenethylamine: colorless solid, MS (ISP): 418.4 MH+.

Example 58

(rac,cis)-1-(2-Cyclohexyl-ethyl)-8-(2-phenyl-cyclohexyl)-1,3,8-triaza-spiro[4.5]decan-4-one In the penultimate step of the synthesis of this example microwave irradiation was utilized as heating source: A solution of (rac,cis)-4-cyclohexyl-ethylamino-1-(2-phenyl-cyclohexyl)-piperidine-4-carboxylic acid amide, prepared analogously to Example 40c) from (rac,cis)-1-(2-phenyl-cyclohexyl)-piperidin-4-one and cyclohexylethylamine, in a mixture of triethyl orthoformate/acetic acid 95:5 was irradiated by microwaves in a sealed tube to 120° C. for 20 minutes. The reaction mixture was then made alkaline with conc. ammonia, extracted with dichloromethane, the combined organic phases were washed with brine, dried over Na₂SO₄, filtered and evaporated. The crude (rac,cis)-1-(2-cyclohexyl-ethyl)-8-(2-phenyl-cyclohexyl)-1,3,8-triaza-spiro[4.5]dec-2-en-4-one was directly used for the last step, the reduction with NaBH₄ as described for Example 40e).

(rac,cis)-1-(2-Cyclohexyl-ethyl)-8-(2-phenyl-cyclohexyl)-1,3,8-triaza-spiro[4.5]decan-4-one was prepared from (rac,cis)-1-(2-phenyl-cyclohexyl)-piperidin-4-one and cyclohexylethylamine hydrochloride: colorless solid, MS (ISP): 424.5 MH⁺.

In analogy to Example 58 the following spiropiperidines of Example 59–64 were prepared from the given starting material that is either commercially available or described in the literature.

Example 59

(rac,cis)-1-(3,4-Dichloro-phenyl)-8-(2-phenyl-cyclohexyl)-1,3,8-triaza-spiro[4.5]decan-4-one (rac,cis)-1-(3,4-Dichloro-phenyl)-8-(2-phenyl-cyclohexyl)-1,3,8-triaza-spiro[4.5]decan-4-one was prepared from (rac,cis)-1-(2-phenyl-cyclohexyl)-piperidin-4-one and 3,4-dichloroaniline: colorless powder, MS (ISP): 458.4 MH⁺.

Example 60

(rac,cis)-1-Hexyl-8-(2-phenyl-cyclohexyl)-1,3,8-triaza-spiro[4.5]decan-4-one (rac,cis)-1-Hexyl-8-(2-phenyl-cyclohexyl)-1,3,8-triaza-spiro[4.5]decan-4-one was prepared from (rac,cis)-1-(2-phenyl-cyclohexyl)-piperidin-4-one and 1-hexylamine hydrochloride: colorless powder, MS (ISP): 398.5 MH⁺.

Example 61

(rac,cis)-8-(2-Phenyl-cyclohexyl)-1-(4-trifluoromethyl-phenyl)-1,3,8-triaza-spiro[4.5]decan-4-one (rac,cis)-8-(2-Phenyl-cyclohexyl)-1-(4-trifluoromethyl-phenyl)-1,3,8-triaza-spiro[4.5]decan-4-one was prepared from (rac,cis)-1-(2-phenyl-cyclohexyl)-piperidin-4-one and 4-aminobenzo-trifluoride: colorless powder, MS (ISP): 458.5 MH⁺.

Example 62

(rac,cis)-8-(2-Phenyl-cyclohexyl)-1-(2,2,2-trifluoro-ethyl)-1,3,8-triaza-spiro[4.5]decan-4-one (rac,cis)-8-(2-Phenyl-cyclohexyl)-1-(2,2,2-trifluoro-ethyl)-1,3,8-triaza-spiro[4.5]decan-4-one was prepared from (rac,cis)-1-(2-phenyl-cyclohexyl)-piperidin-4-one and 3,3,3-trifluoroethylamine hydrochloride: colorless oil, MS (ISP): 396.3 MH⁺.

Example 63

(rac,cis)-8-(2-Phenyl-cyclohexyl)-1-(2-thiomorpholin-4-yl-ethyl)-1,3,8-triaza-spiro[4.5]decan-4-one (rac,cis)-8-(2-Phenyl-cyclohexyl)-1-(2-thiomorpholin-4-yl-ethyl)-1,3,8-triaza-spiro[4.5]decan-4-one was prepared from (rac,cis)-1-(2-phenyl-cyclohexyl)-piperidin-4-one and 1-(2-aminoethyl)thiomorpholine hydrochloride: colorless solid, MS (ISP): 443.4 MH⁺.

Example 64

(rac,cis)-2-Methyl-1-phenyl-8-(2-phenyl-cyclohexyl)-1,3,8-triaza-spiro[4.5]decan-4-one a) (rac,cis)-4-Phenylamino-1-(2-phenyl-cyclohexyl)-piperidine-4-carboxylic acid amide

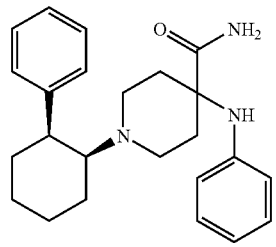

To a solution of 2.00 g (7.78 mmol) (rac,cis)-1-(2-phenyl-cyclohexyl)-piperidin-4-one (Example 40b) in 30 ml acetic acid were added 2.03 g (21.8 mmol) aniline and at 0° C. slowly a solution of 1.42 g (21.8 mmol) potassium cyanide in 5 ml water. The mixture was stirred at ambient temperature for 60 h. The reaction mixture was poured onto 75 ml water and extracted with dichloromethane. The pooled extracts were washed with aqueous half saturated NaHCO₃ solution and brine, dried over Na₂SO₄, filtered and evaporated: 2.90 g (rac,cis)-4-phenylamino-1-(2-phenyl-cyclohexyl)-piperidine-4-carbonitrile as yellow oil. The latter was dissolved in 20 ml 90% H₂SO₄ and stirred at ambient temperature for 16 h. The reaction mixture was poured onto 50 ml iced water, the solution made alkaline with conc. NaOH and extracted with dichloromethane. The pooled extracts were washed with water and brine, dried over Na₂SO₄, filtered and evaporated. The crude product was purified by flash-chromatography over silica gel with an AcOEt/MeOH gradient: 0.862 g (rac,cis)-4-phenylamino-1-(2-phenyl-cyclohexyl)-piperidine-4-carboxylic acid amide as a colorless solid: MS (ISP): 378.3 MH⁺.

b) (rac,cis)-1-Phenyl-8-(2-phenyl-cylohexyl)-1,3,8-triaza-spiro[4.5]dec-2-en-4-one

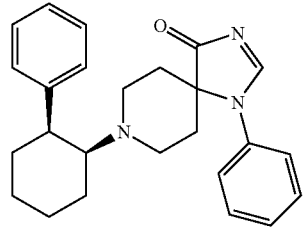

A solution of 85 mg (2.25 mmol) of (rac,cis)-4-amino-1-(2-phenyl-cyclohexyl)-piperidine-4-carboxylic acid amide, 1.2 ml triethyl orthoformate and 0.24 ml AcOH in 4 ml toluene were heated to reflux for 24 h. The reaction mixture was poured onto iced water, made alkaline by addition of conc. ammonia and extracted with dichloromethane. The organic extracts were washed with brine, dried over Na₂SO₄, filtered and evaporated. The crude product was purified by flash-chromatography on silica gel with AcOEt as eluent: 119 mg (rac,cis)-1-phenyl-8-(2-phenyl-cyclohexyl)-1,3,8-triaza-spiro[4.5]dec-2-en-4-one as light yellow oil, which on crystallisation from pentane provided an off-white powder: MS (ISP): 388.3 MH+.

c) (rac,cis)-2-Methyl-1-phenyl-8-(2-phenyl-cyclohexyl)-1,3,8-triaza-spiro[4.5]decan-4-one A solution of 100 mg (0.258 mmol) (rac,cis)-1-phenyl-8-(2-phenyl-cyclohexyl)-1,3,8-triaza-spiro[4.5]dec-2-en-4-one in 10 ml THF was cooled to −78° C. and 0.300 ml of a 3M methyl magnesium chloride solution in THF was added drop-wise. The mixture was stirred at −78° C. for 30 min. and then allowed to warm to 0° C. The reaction was quenched by addition of NH4OH (25%) at 0° C. and the mixture then extracted three times with dichloromethane. The combined organic layers were dried on Na2SO4, filtered and evaporated. The residue was purified by flash-chromatography with an AcOEt/MeOH gradient as eluent: 67 mg 2-methyl-1-phenyl-8-(2-phenyl-cyclohexyl)-1,3,8-triaza-spiro[4.5]decan-4-one were obtained as a colorless foamy solid: MS (ISP): 404.6 MH+.

Example 65

(rac,cis)-2-Ethyl-1-phenyl-8-(2-phenyl-cyclohexyl)-1,3,8-triaza-spiro[4.5]decan-4-one A solution of 100 mg (0.258 mmol) (rac,cis)-1-phenyl-8-(2-phenyl-cyclohexyl)-1,3,8-triaza-spiro[4.5]dec-2-en-4-one (Example 64a)) in 10 ml THF was cooled to −78° C. and 0.800 ml of a 1M solution of ethyl magnesium bromide was added dropwise. The mixture was stirred at −78° C. for 30 min and then allowed to warm to 0° C. The reaction was quenched by addition of NH4OH (25%) at 0° C. and the mixture was extracted three times with dichloromethane. The combined organic layers were dried on Na2SO4, filtered and evaporated. The residue was purified by-flash chromatography with an AcOEt/MeOH gradient as eluent: 52 mg (rac,cis)-2-ethyl-1-phenyl-8-(2-phenyl-cyclohexyl)-1,3,8-triaza-spiro[4.5]decan-4-one were obtained as an off-white foamy solid: MS (ISP): 418.6 MH+.

Example 66

(rac,cis)-2,2-Dimethyl-1-phenyl-8-(2-phenyl-cyclohexyl)-1,3,8-triaza-spiro[4.5]decan-4-one A suspension of 90 mg (0.238 mmol) (rac,cis)-4-phenylamino-1-(2-phenyl-cyclohexyl)-piperidine-4-carboxylic acid amide (Example 64a) in 1 ml toluene were treated with 1.7 g (23.6 mmol) 2-methoxypropene. 220 mg (1.16 mmol) pTsOH.H2O were added in portions of about 50 mg at ambient temperature. An exothermic reaction took place. After completion of the last addition, the reaction mixture was treated with 1N NaOH and extracted several times with dichloromethane. The combined organic phases were dried on Na2SO4, filtered and evaporated to a yellow oil, which was purified by flash-chromatography with a dichloromethane/methanol gradient as eluent. The collected fractions were re-columned with toluene/diisopropylamine 9:1, yielding 28 mg (rac,cis)-2,2-dimethyl-1-phenyl-8-(2-phenyl-cyclohexyl)-1,3,8-triaza-spiro[4.5]decan-4-one as a colorless foamy solid: MS (ISP): 418.4 MH+.

Procedure B1

Example 67

Preparation of (rac,cis)-1-Cyclopropylmethyl-8-(2-phenyl-cyclohexyl)-1,3,8-triaza-spiro[4.5]decan-4-one a) (rac,cis)4-Amino-1-(2-phenyl-cyclohexyl)-piperidine-4-carboxylic acid amide

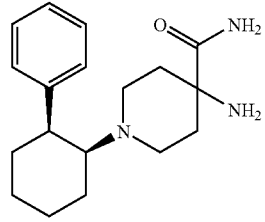

To a solution of 1.29 g (5.0 mmol) (rac,cis)-1-(2-phenyl-cyclohexyl)-piperidin-4-one in 11 ml EtOH was added 0.295 g (5.5 mmol) ammonium chloride, the reaction mixture stirred for 5 min. and then 0.359 g KCN (5.5 mmol) was added and the mixture stirred at ambient temperature for 20 h. Then the reaction mixture was diluted with 10 ml water, extracted with dichloromethane, the combined organic phases washed with brine, dried over Na2SO4 and evaporated. The residue, 1.45 g (rac,cis)-4-amino-1-(2-phenyl-cyclohexyl)-piperidine-4-carbonitrile, was dissolved in 15 ml 90% H2SO4 and stirred at ambient temperature for 2 h. Then the mixture was poured onto iced water, made alkaline by addition of 45 ml conc. ammonia and extracted with AcOEt. The organic phase was washed with brine, dried over Na2SO4, filtered and evaporated. The crude product was purified by flash-chromatography on silica gel with a dichloromethane/methanol gradient. The purified product crystallized at ambient temperature and was triturated in Et2O, filtered and dried: 1.04 g (rac,cis)-4-amino-1-(2-phenyl-cyclohexyl)-piperidine-4-carboxylic acid amide as off-white crystals: MS (ISP): 302.3 MH+.

b) (rac,cis)-8-(2-Phenyl-cyclohexyl)-1,3,8-triaza-spiro[4.5]decan-4-one

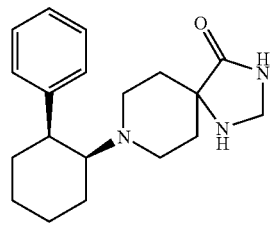

A suspension of 220 mg (0.73 mmol) of (rac,cis)-4-amino-1-(2-phenyl-cyclohexyl)-piperidine-4-carboxylic acid amide in 1.2 ml triethyl orthoformate and 0.05 ml AcOH was heated by microwave irradiation to 120° C. for 10 min. The reaction mixture was poured onto water and extracted with dichloromethane, the organic phase washed with brine, dried over Na2SO4, filtered and evaporated. The residue ((rac,cis)-1-phenyl-8-(2-phenyl-cyclohexyl)-1,3,8-triaza-spiro[4.5]dec-2-en-4-one as a light brown oil) was dissolved in 5 ml methanol. To this solution were added portion-wise 206 mg (5.44 mmol) NaBH$_4$ and stirred at ambient temperature for 1.5 h. Then the solvent was evaporated, the residue distributed between dichloromethane and diluted ammonia (1:1 H$_2$O/conc. ammonia), the organic phase was washed with brine, dried over Na$_2$SO$_4$, filtered and evaporated. The crude product was purified by flash-chromatography on silica gel with an AcOEt/MeOH gradient: 170 mg (rac,cis)-8-(2-phenyl-cyclohexyl)-1,3,8-triaza-spiro[4.5]decan-4-one as colorless crystals: m.p. 126–128° C. (from pentane/Et$_2$O 5:1), MS (ISP): 314.1 MH$^+$.

c) (rac,cis)-1-Cyclopropylmethyl-8-(2-phenyl-cyclohexyl)-1,3,8-triaza-spiro[4.5]decan-4-one To a solution of 37 mg (0.12 mmol) (rac,cis)-8-(2-phenyl-cyclohexyl)-1,3,8-triaza-spiro[4.5]decan-4-one in 2 ml EtOH were added 0.013 ml (12.4 mg, 0.18 mmol) cyclopropane-carboxaldehyde and 0.059 ml (57 mg, 0.23 mmol) titanium(IV) tetraisopropoxide. The stirred mixture was heated to 60° C. for 5 h. Then the reaction mixture was cooled to 40° C., 15 mg (0.24 mmol) NaCNBH$_3$ added and the mixture kept at this temperature for an additional hour. After keeping the reaction mixture over night at ambient temperature, it was evaporated, the residue took up in 10 ml dichloromethane and 5 ml 1N NaOH and stirred at ambient temperature for 10 min. The slurry was filtered through a Dicalite pad, extracted with dichloromethane, the organic phase washed with brine, dried over Na$_2$SO$_4$, filtered and evaporated. The resulting yellow oil (47 mg) were purified by flash-chromatography over silica gel with AcOEt/MeOH 9:1 as eluent: 19.1 mg starting material were recovered and 4.7 mg (rac,cis)-1-cyclopropylmethyl-8-(2-phenyl-cyclohexyl)-1,3,8-triaza-spiro[4.5]decan-4-one as colorless oil: MS (ISP): 368.4 MH$^+$.

Procedure C

Example 68

Preparation of (rac,trans)-1-Phenyl-8-(2-phenyl-cyclohexyl)-1,3,8-triaza-spiro[4.5]decan-4-one (rac,trans)-1-(2-Phenyl-cyclohexyl)-piperidin-4-one

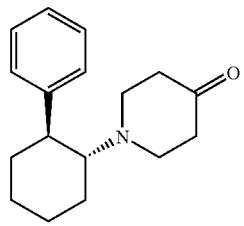

To a solution of 500 mg (2.85 mmol) (rac,trans)-2-phenyl-cyclohexylamine and 40 mg (0.29 mmol) potassium carbonate in 5 ml EtOH was added drop-wise a solution of 1.15 g (4.27 mmol) 1-ethyl-1-methyl-4-oxo-piperidinium iodide in 2 ml water and the mixture heated to reflux for 45 min. Then water was added, cooled to ambient temperature and extracted with AcOEt. The combined organic extracts were washed with brine, dried over Na$_2$SO$_4$, filtered and evaporated. The resulting crude product was purified by flash-chromatography on silica gel with hexane/AcOEt 5:1: 540 mg (rac,trans)-1-(2-phenyl-cyclohexyl)-piperidin-4-one as yellow oil: MS (ISP): 258.3 MH$^+$.

(rac,trans)-1-Phenyl-8-(2-phenyl-cyclohexyl)-1,3,8-triaza-spiro[4.5]decan-4-one

Starting with (rac,trans)-1-(2-phenyl-cyclohexyl)-piperidin-4-one and aniline following in analogy the reaction sequence given for (rac,cis)-1-ethyl-8-(2-phenyl-cyclohexyl)-1,3,8-triaza-spiro[4.5]decan-4-one provided via the intermediates (rac,trans)-4-phenylamino-1-(2-phenyl-cyclohexyl)-piperidine-4-carbonitrile (MS (ISP): 360.4 MH$^+$), and (rac,trans)-1-phenyl-8-(2-phenyl-cyclohexyl)-1,3,8-triaza-spiro[4.5]dec-2-en-4-one (MS (ISP): 388.4 MH$^+$), (rac,trans)-1-phenyl-8-(2-phenyl-cyclohexyl)-1,3,8-triaza-spiro[4.5]decan-4-one as colorless solid: m.p. 254–256° C., MS (ISP): 390.4 MH$^+$.

Procedure D

Example 69

(rac,cis)-3-Methyl-1-phenyl-8-(2-phenyl-cyclohexyl)-1,3,8-triaza-spiro[4.5]decan-4-one To a solution of 100 mg (0.26 mmol) (rac,cis)-1-phenyl-8-(2-phenyl-cyclohexyl)-1,3,8-triaza-spiro[4.5]decan-4-one (Example 1) in 5 ml DMF were added 10 mg (0.42 mmol) sodium hydride and the mixture stirred under Argon at ambient temperature for 30 minutes. Then 60 mg (0.43 mmol) methyl iodide were added to the yellowish solution and stirred for further 2 h at ambient temperature. The resulting reaction mixture was evaporated, dissolved in water and extracted with AcOEt. The combined organic phases were washed with brine, dried over Na$_2$SO$_4$ and evaporated. The crude product (160 mg yellow oil) was purified by flash-chromatography on silica gel with a gradient of dichloromethane/methanol 95:5 to 90:10 as eluent: 27.1 mg (rac,cis)-3-methyl-1-phenyl-8-(2-phenyl-cyclohexyl)-1,3,8-triaza-spiro[4.5]decan-4-one as colorless crystals: MS (ISP): 404.6 MH$^+$.

In analogy to Example 69 the following spiropiperidines of Example 70–72 were prepared from (rac,cis)-1-phenyl-8-(2-phenyl-cyclohexyl)-1,3,8-triaza-spiro[4.5]decan-4-one (Example 1) and the corresponding alkyl halide.

Example 70

(rac,cis)-3-Ethyl-1-phenyl-8-(2-phenyl-cyclohexyl)-1,3,8-triaza-spiro[4.5]decan-4-one (rac,cis)-3-Ethyl-1-phenyl-8-(2-phenyl-cyclohexyl)-1,3,8-triaza-spiro[4.5]decan-4-one was prepared by alkylation with ethyl iodide: colorless solid: MS (ISP): 418.4 MH$^+$.

Example 71

(rac,cis)-3-Isopropyl-1-phenyl-8-(2-phenyl-cyclohexyl)-1,3,8-triaza-spiro[4.5]decan-4-one (rac,cis)-3-Isopropyl-1-phenyl-8-(2-phenyl-cyclohexyl)-1,3,8-triaza-spiro[4.5]decan-4-one was prepared by alkylation with isopropyl iodide: colorless solid: MS (ISP): 432.6 MH$^+$.

Example 72

(rac,cis)-3-Benzyl-1-phenyl-8-(2-phenyl-cyclohexyl)-1,3,8-triaza-spiro[4.5]decan-4-one (rac,cis)-3-Benzyl-1-phenyl-8-(2-phenyl-cyclohexyl)-1,3,8-triaza-spiro[4.5]decan-4-one was prepared by alkylation with benzyl bromide: off-white solid: MS (ISP): 480.5 MH$^+$.

Procedure E

Example 73

(rac,cis)-8-(2-Hydroxy-2-phenyl-cyclohexyl)-1-(3-methyl-butyl)-1,3,8-triaza-spiro[4.5]decan-4-one a) 8-Benzyl-1-(3-methyl-butyl)-1,3,8-triaza-spiro[4.5]decan-4-one

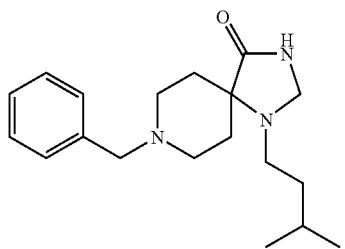

To a solution of 100 mg (0.408 mmol) 8-benzyl-1,3,8-triaza-spiro[4,5]decan-4-one (m.p. 164–166° C.) and 0.062 ml (49.2 mg, 0.571 mmol) isovaleraldehyde in 3 ml 1,2-dichloroethane were added 130 mg (0.611 mmol) sodium triacetoxyborohydride and the mixture stirred at ambient temperature for 16 h. Then the reaction mixture was quenched with 10 ml saturated aqueous NaHCO$_3$-solution and extracted with dichloromethane. The organic extracts were washed with brine, dried over Na$_2$SO$_4$, filtered and evaporated: 128 mg 8-benzyl-1-(3-methyl-butyl)-1,3,8-triaza-spiro[4.5]decan-4-one as colorless crystals: m.p. 139–140° C., MS (ISP): 316.4 MH$^+$.

b) 1-(3-Methyl-butyl)-1.3,8-triaza-spiro[4.5]decan-4-one

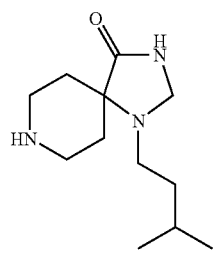

A solution of 130 mg (0.412 mmol) 8-benzyl-1-(3-methyl-butyl)-1,3,8-triaza-spiro[4.5]decan-4-one in 2 ml methanol was debenzylated with hydrogen in presence of 30 mg 10% Pd/C at ambient temperature over night. Then the reaction mixture was filtered through a silica gel pad and the filtrate evaporated: 70 mg 1-(3-methyl-butyl)-1,3,8-triaza-spiro[4.5]decan-4-one as colorless solid: m.p. 103–105° C., MS (ISP): 226.3 MH$^+$.

c) (rac,trans)-8-(2-Hydroxy-cyclohexyl)-1-(3-methyl-butyl)-1,3,8-triaza-spiro[4.5]decan-4-one

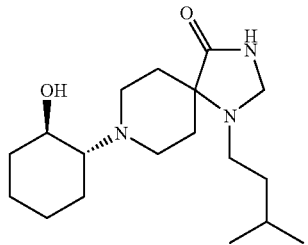

To a solution of 225 mg (1.0 mmol) 1-(3-methyl-butyl)-1,3,8-triaza-spiro[4.5]decan-4-one in 2 ml EtOH were added 0.11 ml (162 mg, 1.65 mmol) cyclohexene oxide and the reaction mixture heated to reflux temperature for 16 h, then further 0.5 ml (0.5 mmol) cyclohexene oxide were added and the mixture refluxed for additional 6 h. Then the reaction mixture was evaporated and the resulting 404 mg colorless oil purified by flash-chromatography on silica gel with AcOEt/MeOH 9:1 as eluent. Triturating the pure fractions in pentane/Et$_2$O 1:1 provided 79 mg (rac,trans)-8-(2-hydroxy-cyclohexyl)-1-(3-methyl-butyl)-1,3,8-triaza-spiro[4.5]decan-4-one as colorless solid: m.p. 140–142° C., MS (ISP): 324.3 MH$^+$.

d) rac-1-(3-Methyl-butyl)-8-(2-oxo-cyclohexyl)-1,3,8-triaza-spiro[4.5]decan-4-one

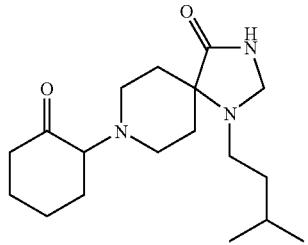

To a cooled solution of 165 mg (0.51 mmol) (rac,trans)-8-(2-hydroxy-cyclohexyl)-1-(3-methyl-butyl)-1,3,8-triaza-spiro[4.5]decan-4-one in 3 ml dichloromethane, 1.7 ml DMSO and 0.355 ml (258 mg, 2.55 mmol) triethylamine was added at 0° C. drop-wise a solution of 250 mg (1.57 mmol) sulfur trioxide-pyridine complex in 1.5 ml DMSO. The mixture was stirred at ambient temperature for 1 h. Then the reaction mixture was poured onto 15 ml water and extracted extensively with dichloromethane. The combined organic extracts were washed with brine, dried over Na$_2$SO$_4$, filtered and evaporated. The resulting 186 mg brown oil were purified by flash-chromatography on silica gel with AcOEt/MeOH 9:1 as eluent: 123 mg rac-1-(3-methyl-butyl)-8-(2-oxo-cyclohexyl)-1,3,8-triaza-spiro[4.5]decan-4-one as yellowish crystals. Re-crystallisation of a sample from Et$_2$O provided a colorless compound: m.p. 144–146° C., MS (ISP): 322.3 MH$^+$.

e) (rac,cis)-8-(2-Hydroxy-2-phenyl-cyclohexyl)-1-(3-methyl-butyl)-1.3,8-triaza-spiro[4.5]decan-4-one To a cooled solution of 108 mg (0.336 mmol) rac-1-(3-methyl-butyl)-8-(2-oxo-cyclohexyl)-1,3,8-triaza-spiro[4.5]decan-4-one in 3 ml abs. THF was added at −70° C. dropwise 0.43 ml of a 1.7 M phenyllithium solution in THF and, after 1 h at −70° C., further 0.2 ml (total of 90 mg, 1.07 mmol) 1.7 M phenyl-lithium solution in THF were added. After 1 h at −70° C. the reaction was quenched by addition of 5 ml 20% aqueous NH₄Cl-solution. The mixture was extracted with dichloromethane, the combined organic extracts washed with brine, dried over Na₂SO₄, filtered and evaporated. The resulting 157 mg brown oil was purified by flash-chromatography on silica gel with AcOEt/MeOH 9:1 as eluent: 60 mg (rac,cis)-8-(2-hydroxy-2-phenyl-cyclohexyl)-1-(3-methyl-butyl)-1,3,8-triaza-spiro[4.5]decan-4-one as amorphous powder which could be crystallised from Et₂O: m.p. 192–194° C., MS (ISP): 400.4 MH⁺.

Example 74

(rac,cis)-8-(2-Hydroxy-2-phenyl-cyclohexyl)-1-phenyl-1,3,8-triaza-spiro[4.5]decan-4-one a) (rac, trans) 8-(2-Hydroxy-cyclohexyl)-1-phenyl-1,3,8-triaza-spiro[4.5]decan-4-one

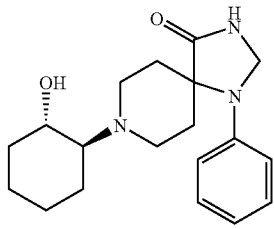

The title compound was prepared from cyclohexene oxide and 1-phenyl-1,3,8-triazaspiro[4,5]decan-4-one in analogy of the procedure described for the synthesis of (rac,trans)-8-(2-hydroxy-cyclohexyl)-1-(3-methyl-butyl)-1,3,8-triaza-spiro[4.5]decan-4-one (Example 73c). (rac,trans) 8-(2-Hydroxy-cyclohexyl)-1-phenyl-1,3,8-triaza-spiro[4.5]decan-4-one was obtained as colorless solid, MS (ISP): 330.3 MH⁺.

b) rac-8-(2-Oxo-cyclohexyl)-1-phenyl-1,3,8-triaza-spiro[4.5]decan-4-one

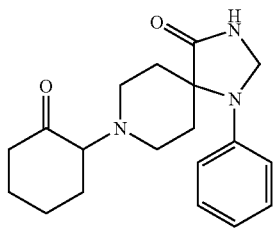

The title compound was prepared from (rac,trans) 8-(2-hydroxy-cyclohexyl)-1-phenyl-1,3,8-triaza-spiro[4.5]decan-4-one in analogy of the procedure described for the synthesis of rac-1-(3-methyl-butyl)-8-(2-oxo-cyclohexyl)-1,3,8-triaza-spiro[4.5]decan-4-one (Example 73d). rac-8-(2-Oxo-cyclohexyl)-1-phenyl-1,3,8-triaza-spiro[4.5]decan-4-one was obtained as yellow solid, MS (ISP): 328.4 MH⁺.

c) (rac,cis)-8-(2-Hydroxy-2-phenyl-cyclohexyl)-1-phenyl-1,3,8-triaza-spiro[4.5]decan-4-one The title compound was prepared from rac-8-(2-oxo-cyclohexyl)-1-phenyl-1,3,8-triaza-spiro[4.5]decan-4-one and phenyllithium in analogy of the procedure described for the synthesis of (rac,cis)-8-(2-hydroxy-2-phenyl-cyclohexyl)-1-(3-methyl-butyl)-1,3,8-triaza-spiro[4.5]decan-4-one (Example 73e). (rac,cis)-8-(2-Hydroxy-2-phenyl-cyclohexyl)-1-phenyl-1,3,8-triaza-spiro[4.5]decan-4-one was obtained as off-white solid, MS (ISP): 406.5 MH⁺.

Example 75

(rac,cis)-8-[2-(4-Fluoro-phenyl)-2-hydroxy-cyclohexyl]-1-phenyl-1,3,8-triaza-spiro[4.5]decan-4-one The title compound was prepared from rac-8-(2-oxo-cyclohexyl)-1-phenyl-1,3,8-triaza-spiro[4.5]decan-4-one and p-fluorophenyl-lithium in analogy of the procedure described for the synthesis of (rac,cis)-8-(2-hydroxy-2-phenyl-cyclohexyl)-1-(3-methyl-butyl)-1,3,8-triaza-spiro[4.5]decan-4-one (Example 73e). (rac,cis)-8-[2-(4-Fluoro-phenyl)-2-hydroxy-cyclohexyl]-1-phenyl-1,3,8-triaza-spiro[4.5]decan-4-one was obtained as colorless solid, MS (ISP): 424.4 MH⁺.

Example 76

(rac,cis)-8-(2-Hydroxy-2-o-tolyl-cyclohexyl)-1-phenyl-1,3,8-triaza-spiro[4.5]decan-4-one The title compound was prepared from rac-8-(2-oxo-cyclohexyl)-1-phenyl-1,3,8-triaza-spiro[4.5]decan-4-one and o-tolyl-lithium in analogy of the procedure described for the synthesis of (rac,cis)-8-(2-hydroxy-2-phenyl-cyclohexyl)-1-(3-methyl-butyl)-1,3,8-triaza-spiro[4.5]decan-4-one (Example 73e). (rac,cis)-8-(2-Hydroxy-2-o-tolyl-cyclohexyl)-1-phenyl-1,3,8-triaza-spiro[4.5]decan-4-one was obtained as colorless solid, MS (ISP): 420.4 MH⁺.

Example 77

(rac,cis) 8-(2-Hydroxy-2-pyridin-4-yl-cyclohexyl)-1-phenyl-1,3,8-triaza-spiro[4.5]decan-4-one The title compound was prepared from rac-8-(2-oxo-cyclohexyl)-1-phenyl-1,3,8-triaza-spiro[4.5]decan-4-one and 4-pyridyl-lithium in analogy of the procedure described for the synthesis of (rac,cis)-8-(2-hydroxy-2-phenyl-cyclohexyl)-1-(3-methyl-butyl)-1,3,8-triaza-spiro[4.5]decan-4-one (Example 73e). (rac,cis) 8-(2-Hydroxy-2-pyridin-4-yl-cyclohexyl)-1-phenyl-1,3,8-triaza-spiro[4.5]decan-4-one was obtained as colorless solid, MS (ISP): 407.4 MH⁺.

Example 78

(rac,cis)-8-[2-(4-Chloro-phenyl)-2-hydroxy-cyclohexyl]-1-phenyl-1,3,8-triaza-spiro[4.5]decan-4-one The title compound was prepared from rac-8-(2-oxo-cyclohexyl)-1-phenyl-1,3,8-triaza-spiro[4.5]decan-4-one and p-chloro-phenyl-lithium in analogy of the procedure described for the synthesis of (rac,cis)-8-(2-hydroxy-2-phenyl-cyclohexyl)-1-(3-methyl-butyl)-1,3,8-triaza-spiro[4.5]decan-4-one (Example 73e). (rac,cis)-8-[2-(4-Chloro-phenyl)-2-hydroxy-cyclohexyl]-1-phenyl-1,3,8-triaza-spiro[4.5]decan-4-one was obtained as colorless solid, MS (ISP): 440.4 MH⁺.

Example 79

(rac,cis)-8-(2-Hydroxy-2-pyridin-3-yl-cyclohexyl)-1-phenyl-1,3,8-triaza-spiro[4.5]decan-4-one The title compound was prepared from rac-8-(2-oxo-cyclohexyl)-1-phenyl-1,3,8-triaza-spiro[4.5]decan-4-one and 3-pyridyl-lithium in analogy of the procedure described for the synthesis of (rac,cis)-8-(2-hydroxy-2-phenyl-cyclohexyl)-1-(3-methyl-butyl)-1,3,8-triaza-spiro[4.5]decan-4-one (Example 73e). (rac,cis)-8-(2-Hydroxy-2-pyridin-3-yl-cyclohexyl)-1-phenyl-1,3,8-triaza-spiro[4.5]decan-4-one was obtained as pale yellow solid, MS (ISP): 407.4 MH$^+$.

Example 80

(rac,cis) 8-(2-Hydroxy-2-pyridin-2-yl-cyclohexyl)-1-phenyl-1,3,8-triaza-spiro[4.5]decan-4-one The title compound was prepared from rac-8-(2-oxo-cyclohexyl)-1-phenyl-1,3,8-triaza-spiro[4.5]decan-4-one and 2-pyridyl-lithium in analogy of the procedure described for the synthesis of (rac,cis)-8-(2-hydroxy-2-phenyl-cyclohexyl)-1-(3-methyl-butyl)-1,3,8-triaza-spiro[4.5]decan-4-one (Example 73e). (rac,cis) 8-(2-Hydroxy-2-pyridin-2-yl-cyclohexyl)-1-phenyl-1,3,8-triaza-spiro[4.5]decan-4-one was obtained as off-white solid, MS (ISP): 407.4 MH$^+$.

Example 81

(rac,cis)-8-[2-(3-Chloro-phenyl)-2-hydroxy-cyclohexyl]-1-phenyl-1,3,8-triaza-spiro[4.5]decan-4-one The title compound was prepared from rac-8-(2-oxo-cyclohexyl)-1-phenyl-1,3,8-triaza-spiro[4.5]decan-4-one and m-chlorophenyl-lithium in analogy of the procedure described for the synthesis of (rac,cis)-8-(2-hydroxy-2-phenyl-cyclohexyl)-1-(3-methyl-butyl)-1,3,8-triaza-spiro[4.5]decan-4-one (Example 73e). (rac,cis)-8-[2-(3-Chloro-phenyl)-2-hydroxy-cyclohexyl]-1-phenyl-1,3,8-triaza-spiro[4.5]decan-4-one was obtained as colorless solid, MS (ISP): 440.4 MH$^+$.

Example 82

(rac,cis)-8-[2-Hydroxy-2-(3-methoxy-phenyl)-cyclohexyl]-1-phenyl-1,3,8-triaza-spiro[4.5]decan-4-one The title compound was prepared from rac-8-(2-oxo-cyclohexyl)-1-phenyl-1,3,8-triaza-spiro[4.5]decan-4-one and m-methoxyphenyl-lithium in analogy of the procedure described for the synthesis of (rac,cis)-8-(2-hydroxy-2-phenyl-cyclohexyl)-1-(3-methyl-butyl)-1,3,8-triaza-spiro[4.5]decan-4-one (Example 73e). (rac,cis)-8-[2-Hydroxy-2-(3-methoxy-phenyl)-cyclohexyl]-1-phenyl-1,3,8-triaza-spiro[4.5]decan-4-one was obtained as off-white solid, MS (ISP): 436.5 MH$^+$.

Example 83

(rac,cis)-8-(2-Hydroxy-2-p-tolyl-cyclohexyl)-1-phenyl-1,3,8-triaza-spiro[4.5]decan-4-one The title compound was prepared from rac-8-(2-oxo-cyclohexyl)-1-phenyl-1,3,8-triaza-spiro[4.5]decan-4-one and p-tolyl-lithium in analogy of the procedure described for the synthesis of (rac,cis)-8-(2-hydroxy-2-phenyl-cyclohexyl)-1-(3-methyl-butyl)-1,3,8-triaza-spiro[4.5]decan-4-one (Example 73e). (rac,cis)-8-(2-Hydroxy-2-p-tolyl-cyclohexyl)-1-phenyl-1,3,8-triaza-spiro[4.5]decan-4-one was obtained as colorless solid, MS (ISP): 420.4 MH$^+$.

Example 84

(rac,cis)-8-[2-(3,4-Dichloro-phenyl)-2-hydroxy-cyclohexyl]-1-phenyl-1,3,8-triaza-spiro[4.5]decan-4-one The title compound was prepared from rac-8-(2-oxo-cyclohexyl)-1-phenyl-1,3,8-triaza-spiro[4.5]decan-4-one and 3,4-dichlorophenyl-lithium in analogy of the procedure described for the synthesis of (rac,cis)-8-(2-hydroxy-2-phenyl-cyclohexyl)-1-(3-methyl-butyl)-1,3,8-triaza-spiro[4.5]decan-4-one (Example 73e). (rac,cis)-8-[2-(3,4-Dichloro-phenyl)-2-hydroxy-cyclohexyl]-1-phenyl-1,3,8-triaza-spiro[4.5]decan-4-one was obtained as colorless solid, MS (ISP): 474.3 M$^+$.

Example 85

(rac,cis)-8-[2-Hydroxy-2-(4-methoxy-phenyl)-cyclohexyl]-1-phenyl-1,3,8-triaza-spiro[4.5]decan-4-one The title compound was prepared from rac-8-(2-oxo-cyclohexyl)-1-phenyl-1,3,8-triaza-spiro[4.5]decan-4-one and p-methoxyphenyl-lithium in analogy of the procedure described for the synthesis of (rac,cis)-8-(2-hydroxy-2-phenyl-cyclohexyl)-1-(3-methyl-butyl)-1,3,8-triaza-spiro[4.5]decan-4-one (Example 73e). (rac,cis)-8-[2-Hydroxy-2-(4-methoxy-phenyl)-cyclohexyl]-1-phenyl-1,3,8-triaza-spiro[4.5]decan-4-one was obtained as colorless solid, MS (ISP): 436.5 MH$^+$.

Example 86

(rac,cis)-8-[2-Hydroxy-2-(4-trifluoromethyl-phenyl)-cyclohexyl]-1-phenyl-1,3,8-triaza-spiro[4.5]decan-4-one The title compound was prepared from rac-8-(2-oxo-cyclohexyl)-1-phenyl-1,3,8-triaza-spiro[4.5]decan-4-one and p-trifluoromethylphenyl-lithium in analogy of the procedure described for the synthesis of (rac,cis)-8-(2-hydroxy-2-phenyl-cyclohexyl)-1-(3-methyl-butyl)-1,3,8-triaza-spiro[4.5]decan-4-one (Example 73e). (rac,cis)-8-[2-Hydroxy-2-(4-trifluoromethyl-phenyl)-cyclohexyl]-1-phenyl-1,3,8-triaza-spiro[4.5]decan-4-one was obtained as colorless solid; MS (ISP): 420.4 MH$^+$.

Example 87

(rac,cis)-1-(4-Fluoro-phenyl)-8-[2-(4-fluoro-phenyl)-2-hydroxy-cyclohexyl]-1,3,8-triaza-spiro[4.5]decan-4-one a) (rac,trans)-1-(4-Fluoro-phenyl)-8-(2-hydroxy-cyclohexyl)-1,3,8-triaza-spiro[4.5]decan-4-one

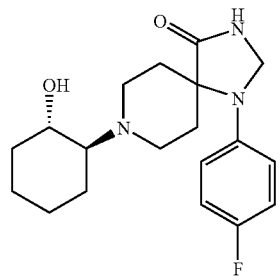

The title compound was prepared from cyclohexene oxide and 1-(4-fluoro-phenyl)-1,3,8-triaza-spiro[4.5]decan-4-one in analogy of the procedure described for the synthesis of (rac,trans)-8-(2-hydroxy-cyclohexyl)-1-(3-methyl-butyl)-1,3,8-triaza-spiro[4.5]decan-4-one (Example 73c). (rac,trans)-1-(4-Fluoro-phenyl)-8-(2-hydroxy-cyclohexyl)-1,3,8-triaza-spiro[4.5]decan-4-one was obtained as off-white solid; MS (ISP): 348.4 MH$^+$.

b) rac-1-(4-Fluoro-phenyl)-8-(2-oxo-cyclohexyl)-1,3,8-triaza-spiro[4.5]decan-4-one

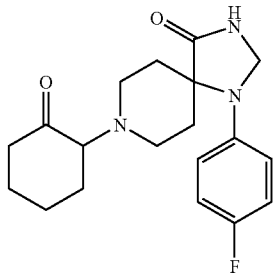

The title compound was prepared from in analogy of the procedure described for the synthesis of rac-1-(3-methyl-butyl)-8-(2-oxo-cyclohexyl)-1,3,8-triaza-spiro[4.5]decan-4-one (Example 73d). rac-1-(4-Fluoro-phenyl)-8-(2-oxo-cyclohexyl)-1,3,8-triaza-spiro[4.5]decan-4-one was obtained as off-white solid; MS (ISP): 346.3 MH$^+$.

c) (rac,cis)-1-(4-Fluoro-phenyl)-8-[2-(4-fluoro-phenyl)-2-hydroxy-cyclohexyl]-1,3,8-triaza-spiro[4.5]decan-4-one The title compound was prepared from rac-1-(4-fluoro-phenyl)-8-(2-oxo-cyclohexyl)-1,3,8-triaza-spiro[4.5]decan-4-one and p-fluoro-phenyl-lithium in analogy of the procedure described for the synthesis of (rac,cis)-8-(2-hydroxy-2-phenyl-cyclohexyl)-1-(3-methyl-butyl)-1,3,8-triaza-spiro[4.5]decan-4-one (Example 73e). (rac,cis)-1-(4-Fluoro-phenyl)-8-[2-(4-fluoro-phenyl)-2-hydroxy-cyclohexyl]-1,3,8-triaza-spiro[4.5]decan-4-one was obtained as light yellow solid, MS (ISP): 442.4 MH$^+$.

Example 88

(rac,cis)-8-[2-(4-Chloro-phenyl)-2-hydroxy-cyclohexyl]-1-(4-fluoro-phenyl)-1,3,8-triaza-spiro[4.5]decan-4-one The title compound was prepared from rac-1-(4-fluoro-phenyl)-8-(2-oxo-cyclohexyl)-1,3,8-triaza-spiro[4.5]decan-4-one and p-chlorophenyl-lithium in analogy of the procedure described for the synthesis of (rac,cis)-8-(2-hydroxy-2-phenyl-cyclohexyl)-1-(3-methyl-butyl)-1,3,8-triaza-spiro[4.5]decan-4-one (Example 73e). (rac,cis)-8-[2-(4-Chloro-phenyl)-2-hydroxy-cyclohexyl]-1-(4-fluoro-phenyl)-1,3,8-triaza-spiro[4.5]decan-4-one was obtained as colorless solid; MS (ISP): 458.5 MH$^+$.

Example 89

(rac,cis)-1-(4-Chloro-phenyl)-8-[2-(4-fluoro-phenyl)-2-hydroxy-cyclohexyl]-1,3,8-triaza-spiro[4.5]decan-4-one a) (rac,trans)-1-(4-Chloro-phenyl)-8-(2-hydroxy-cylohexyl)-1,3,8-triaza-spiro[4.5]decan-4-one

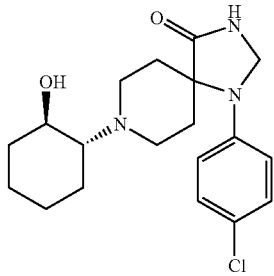

The title compound was prepared from cyclohexene oxide and 1-(4-chloro-phenyl)-1,3,8-triaza-spiro[4.5]decan-4-one in analogy of the procedure described for the synthesis of (rac,trans)-8-(2-hydroxy-cyclohexyl)-1-(3-methyl-butyl)-1,3,8-triaza-spiro[4.5]decan-4-one (Example 73c). (rac,trans)-1-(4-Chloro-phenyl)-8-(2-hydroxy-cyclohexyl)-1,3,8-triaza-spiro[4.5]decan-4-one was obtained as colorless oil; MS (ISP): 364.2 MH$^+$.

b) rac-1-(4-Choro-phenyl)-8-(2-oxo-cyclohexyl)-1,3,8-triaza-spiro[4.5]decan-4-one

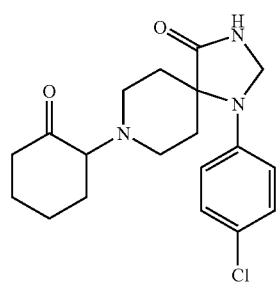

The title compound was prepared from (rac,trans)-1-(4-chloro-phenyl)-8-(2-hydroxy-cyclohexyl)-1,3,8-triaza-spiro[4.5]decan-4-one in analogy of the procedure described for the synthesis of rac-1-(3-methyl-butyl)-8-(2-oxo-cyclohexyl)-1,3,8-triaza-spiro[4.5]decan-4-one (Example 73d). rac-1-(4-Chloro-phenyl)-8-(2-oxo-cyclohexyl)-1,3,8-triaza-spiro[4.5]decan-4-one was obtained as light yellow solid; MS (ISP): 362.2 MH$^+$.

c) (rac,cis)-1-(4-Chloro-phenyl)-8-[2-(4-fluoro-phenyl)-2-hydroxy-cyclohexyl]-1,3,8-triaza-spiro[4.5]decan-4-one The title compound was prepared from rac-1-(4-chloro-phenyl)-8-(2-oxo-cyclohexyl)-1,3,8-triaza-spiro[4.5]decan-4-one and p-fluoro-phenyl-lithium in analogy of the procedure described for the synthesis of (rac,cis)-8-(2-hydroxy-2-phenyl-cyclohexyl)-1-(3-methyl-butyl)-1,3,8-triaza-spiro[4.5]decan-4-one (Example 73e). (rac,cis)-1-(4-Chloro-phenyl)-8-[2-(4-fluoro-phenyl)-2-hydroxy-cyclohexyl]-1,3,8-triaza-spiro[4.5]decan-4-one was obtained as colorless solid; MS (ISP): 458.4 MH$^+$.

Example 90

(rac,cis)-1-(4-Chloro-phenyl)-8-[2-(4-chloro-phenyl)-2-hydroxy-cyclohexyl]-1,3,8-triaza-spiro[4.5]decan-4-one The title compound was prepared from rac-1-(4-chloro-phenyl)-8-(2-oxo-cyclohexyl)-1,3,8-triaza-spiro[4.5]decan-4-one and p-chloro-phenyl-lithium in analogy of the procedure described for the synthesis of (rac,cis)-8-(2-hydroxy-2-phenyl-cyclohexyl)-1-(3-methyl-butyl)-1,3,8-triaza-spiro[4.5]decan-4-one (Example 73e). (rac,cis)-1-(4-Chloro-phenyl)-8-[2-(4-chloro-phenyl)-2-hydroxy-cyclohexyl]-1,3,8-triaza-spiro[4.5]decan-4-one was obtained as colorless solid; MS (ISP): 474.3 M$^+$.

Example 91

(rac,cis)-8-[2-(4-Fluoro-phenyl)-2-hydroxy-cyclohexyl]-1-p-tolyl-1,3,8-triaza-spiro[4.5]decan-4-one a) (rac,trans)-8-(2-Hydroxy-cyclohexyl)-1-p-tolyl-1,3,8-triaza-spiro[4.5]decan-4-one

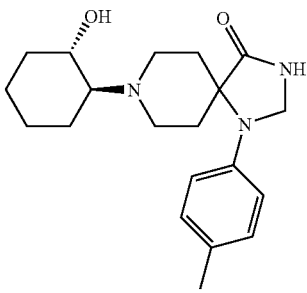

The tide compound was prepared from cyclohexene oxide and 1-p-tolyl-1,3,8-triaza-spiro[4.5]decan-4-one in analogy of the procedure described for the synthesis of (rac,trans)-8-(2-hydroxy-cyclohexyl)-1-(3-methyl-butyl)-1,3,8-triaza-spiro[4.5]decan-4-one (Example 73c). (rac,trans)-8-(2-Hydroxy-cyclohexyl)-1-p-tolyl-1,3,8-triaza-spiro[4.5]decan-4-one was obtained as off-white solid; MS (ISP): 344.4 MH$^+$.

b) rac-8-(2-Oxo-cyclohexyl)-1-p-tolyl-1,3,8-triaza-spiro[4.5]decan-4-one

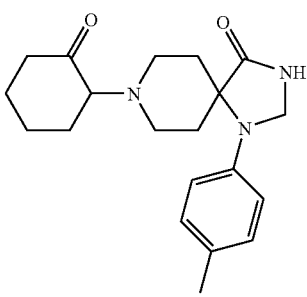

The title compound was prepared from (rac,trans)-8-(2-hydroxy-cyclohexyl)-1-p-tolyl-1,3,8-triaza-spiro[4.5]decan-4-one in analogy of the procedure described for the synthesis of rac-1-(3-methyl-butyl)-8-(2-oxo-cyclohexyl)-1,3,8-triaza-spiro[4.5]decan-4-one (Example 73d). rac-8-(2-oxo-cyclohexyl)-1-p-tolyl-1,3,8-triaza-spiro[4.5]decan-4-one was obtained as light yellow foam; MS (ISP): 342.3 MH$^+$.

c) (rac,cis)-8-[2-(4-Fluoro-phenyl)-2-hydroxy-cyclohexyl]-1-p-tolyl-1,3,8-triaza-spiro[4.5]decan-4-one The title compound was prepared from rac-8-(2-oxo-cyclohexyl)-1-p-tolyl-1,3,8-triaza-spiro[4.5]decan-4-one and p-fluoro-phenyl-lithium in analogy of the procedure described for the synthesis of (rac,cis)-8-(2-hydroxy-2-phenyl-cyclohexyl)-1-(3-methyl-butyl)-1,3,8-triaza-spiro[4.5]decan-4-one (Example 73e). (rac,cis)-8-[2-(4-Fluoro-phenyl)-2-hydroxy-cyclohexyl]-1-p-tolyl-1,3,8-triaza-spiro[4.5]decan-4-one was obtained as off-white solid; MS (ISP): 438.4 MH$^+$.

Example 92

(rac,cis)-8-[2-(4-Chloro-phenyl)-2-hydroxy-cyclohexyl]-1-(4-methoxy-phenyl)-1,3,8-triaza-spiro[4.5]decan-4-one a) (rac,trans)-8-(2-Hydroxy-cyclohexyl)-1-(4-methoxy-phenyl)-1,3,8-triaza-spiro[4.5]decan-4-one

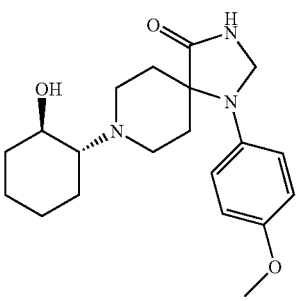

The title compound was prepared from cyclohexene oxide and 1-(4-methoxy-phenyl)-1,3,8-triaza-spiro[4.5]decan-4-one in analogy of the procedure described for the synthesis of (rac,trans)-8-(2-hydroxy-cyclohexyl)-1-(3-methyl-butyl)-1,3,8-triaza-spiro[4.5]decan-4-one (Example 73c). (rac,trans)-8-(2-Hydroxy-cyclohexyl)-1-(4-methoxy-phenyl)-1,3,8-triaza-spiro[4.5]decan-4-one was obtained as colorless solid; MS (ISP): 360.3 MH$^+$.

b) rac-1-(4-Methoxy-phenyl)-8-(2-oxo-cyclohexyl)-1,3,8-triaza-spiro[4.5]decan-4-one

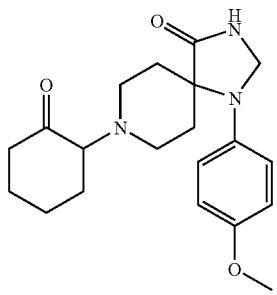

The title compound was prepared from (rac,trans)-8-(2-hydroxy-cyclohexyl)-1-(4-methoxy-phenyl)-1,3,8-triaza-spiro[4.5]decan-4-one in analogy of the procedure described for the synthesis of rac-1-(3-methyl-butyl)-8-(2-oxo-cyclohexyl)-1,3,8-triaza-spiro[4.5]decan-4-one (Example 73d). rac-1-(4-Methoxy-phenyl)-8-(2-oxo-cyclohexyl)-1,3,8-triaza-spiro[4.5]decan-4-one was obtained as yellow oil; MS (ISP): 358.2 MH$^+$.

c) (rac,cis)-8-[2-(4-Chloro-phenyl)-2-hydroxy-cyclohexyl]-1-(4-methoxy-phenyl)-1,3,8-triaza-spiro[4.5]decan-4-one The title compound was prepared from rac-1-(4-methoxy-phenyl)-8-(2-oxo-cyclohexyl)-1,3,8-triaza-spiro[4.5]decan-4-one and p-chloro-phenyl-lithium in analogy of the procedure described for the synthesis of (rac,cis)-8-(2-hydroxy-2-phenyl-cyclohexyl)-1-(3-methyl-butyl)-1,3,8-triaza-spiro[4.5]decan-4-one (Example 73e). (rac,cis)-8-[2-(4-Chloro-phenyl)-2-hydroxy-cyclohexyl]-1-(4-methoxy-phenyl)-1,3,8-triaza-spiro[4.5]decan-4-one was obtained as colorless solid; MS (ISP): 470.3 MH$^+$.

Procedure F

Example 93

(rac,cis)-8-(2-Hydroxy-2-phenyl-cyclohexyl)-1-(3,3,3-trifluoro-propyl)-1,3,8-triaza-spiro[4.5]decan-4-one a) (racstrans)-8-(2-Hydroxy-cyclohexyl)-1,3,8-triaza-spiro[4.5]decan-4-one

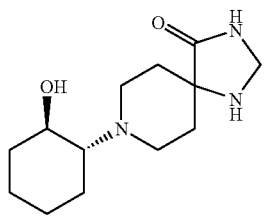

To a solution of 400 mg (2.58 mmol) 1,3,8-triaza-spiro[4.5]decan-4-one in 5 ml EtOH were added 417 mg (4.25 mmol) cyclohexene oxide and the mixture heated to reflux for 16 h. The resulting suspension was evaporated and the residue purified by flash-chromatography on silica gel with methanol as eluent: 547 mg of (rac,trans)-8-(2-hydroxy-cyclohexyl)-1,3,8-triaza-spiro[4.5]decan-4-one as colorless solid. A sample triturated in Et$_2$O showed m.p. 244–245° C. and MS (ISP): 254.4 MH$^+$.

b) (rac,trans)-(E)-8-(2-Hydroxy-cylohexyl)-1-(3,3,3-trifluoro-propenyl)-1,3,8-triaza-spiro[4.5]decan-4-one

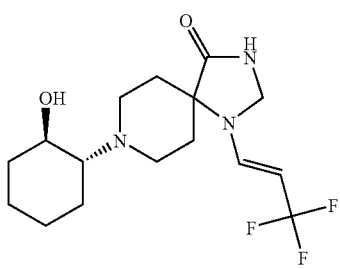

To a solution of 400 mg (1.58 mmol) (rac,trans)-8-(2-hydroxy-cyclohexyl)-1,3,8-triaza-spiro[4.5]decan-4-one and 247 mg (2.20 mmol) 3,3,3-trifluoropropionaldehyde in 60 ml 1,2-dichloroethane were added 500 mg (2.36 mmol) sodium triacetoxyborohydride and the mixture stirred at ambient temperature for 64 h. Then the reaction mixture was quenched with 10 ml saturated aqueous NaHCO$_3$-solution and extracted with dichloromethane. The organic extracts were washed with brine, dried over Na$_2$SO$_4$, filtered and evaporated: 490 mg (rac,trans)-(E)-8-(2-hydroxy-cyclohexyl)-1-(3,3,3-trifluoro-propenyl)-1,3,8-triaza-spiro[4.5]decan-4-one as colorless amorphous solid: MS (ISP): 348.4 MH$^+$.

c) (rac,trans)-8-(2-Hydroxy-cyclohexyl)-1-(3,3,3-trifluoro-propyl)-1,3,8-triaza-spiro[4.5]decan-4-one

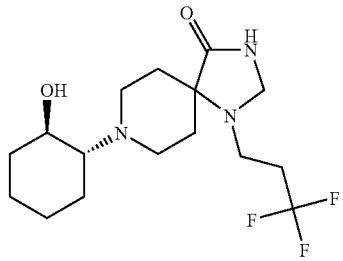

To a solution of 490 mg (1.41 mmol) (rac,trans)-(E)-8-(2-hydroxy-cyclohexyl)-1-(3,3,3-trifluoro-propenyl)-1,3,8-triaza-spiro[4.5]decan-4-one in 40 ml methanol were added 20 mg 10% Pd/C and stirred under a hydrogen atmosphere at ambient temperature for 1 h. Then the reaction mixture was filtered, evaporated and the residue purified by flash-chromatography on silica gel with AcOEt/MeOH 8:2 as eluent: 373 mg (rac,trans)-8-(2-hydroxy-cyclohexyl)-1-(3,3,3-trifluoro-propyl)-1,3,8-triaza-spiro[4.5]decan-4-one as a colorless oil which could be crystallised from Et$_2$O: 304 mg colorless crystals of m.p. 185–187° C., MS (ISP): 350.4 MH$^+$.

d) rac-8-(2-Oxo-cyclohexyl)-1-(3,3,3-trifluoro-propyl)-1,3,8-triaza-spiro[4.5]decan-4-one

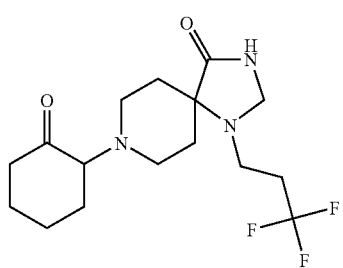

Oxidation of (rac,trans)-8-(2-hydroxy-cyclohexyl)-1-(3,3,3-trifluoro-propyl)-1,3,8-triaza-spiro[4.5]decan-4-one with sulfur trioxide-pyridine complex as described for (rac,trans)-8-(2-hydroxy-cyclohexyl)-1-(3-methyl-butyl)-1,3,8-triaza-spiro[4.5]decan-4-one (Example 73d) provided rac-8-(2-oxo-cyclohexyl)-1-(3,3,3-trifluoro-propyl)-1,3,8-triaza-spiro[4.5]decan-4-one colorless solid: m.p. 196–198° C., MS (ISP): 348.4 MH$^+$.

e) (rac,cis)-8-(2-Hydroxy-2-phenyl-cyclohexyl)-1-(3,3,3-trifluoro-propyl)-1,3,8-triaza-spiro[4.5]decan-4-one Prepared from rac-8-(2-oxo-cyclohexyl)-1-(3,3,3-trifluoro-propyl)-1,3,8-triaza-spiro[4.5]decan-4-one and phenyl-lithium in analogy to (rac,cis)-8-(2-hydroxy-2-phenyl-cyclohexyl)-1-(3-methyl-butyl)-1,3,8-triaza-spiro[4.5]decan-4-one (Example 73e) provided (rac,cis)-8-(2-hydroxy-2-phenyl-cyclohexyl)-1-(3,3,3-trifluoro-propyl)-1,3,8-triaza-spiro[4.5]decan-4-one as colorless solid: m.p. 197–198° C., MS (ISP): 426.2 MH$^+$.

Example 94

(rac,cis)-1-Cyclohexylmethyl-8-(2-hydroxy-2-phenyl-cyclohexyl)-1,3,8-triaza-spiro[4.5]decan-4-one a) (rac,trans)-1-Cyclohexylmethyl-8-(2-hydroxy-cyclohexyl)-1,3,8-triaza-spiro[4.5]decan-4-one

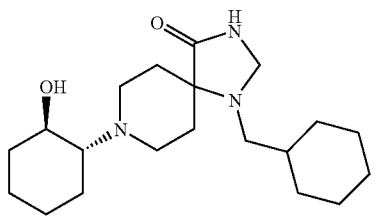

To a solution of 150 mg (0.59 mmol) (rac,trans)-8-(2-hydroxy-cyclohexyl)-1,3,8-triaza-spiro[4.5]decan-4-one (Example 93a) and 98 mg (0.83 mmol) cyclohexanecarboxaldehyde in 3.5 ml 1,2-dichloroethane were added 198 mg (0.889 mmol) sodium triacetoxyborohydride and the mixture stirred at ambient temperature for 2.5 h. Then the reaction mixture was quenched with 10 ml saturated aqueous NaHCO$_3$-solution and extracted with dichloromethane. The organic extracts were washed with brine, dried over Na$_2$SO$_4$, filtered and evaporated: 219 mg (rac,trans)-1-cyclohexylmethyl-8-(2-hydroxy-cyclohexyl)-1,3,8-triaza-spiro[4.5]decan-4-one as colorless solid: MS (ISP): 350.4 MH$^+$.

b) rac-1-Cyclohexylmethyl-8-(2-oxo-cyclohexyl)-1,3,8-triaza-spiro[4.5]decan-4-one

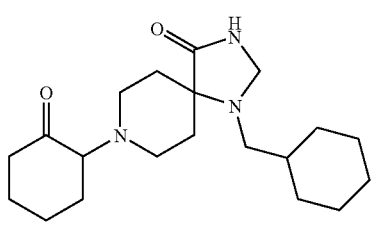

The title compound was prepared from (rac,trans)-1-cyclohexylmethyl-8-(2-hydroxy-cyclohexyl)-1,3,8-triaza-spiro[4.5]decan-4-one in analogy of the procedure described for the synthesis of rac-1-(3-methyl-butyl)-8-(2-oxo-cyclohexyl)-1,3,8-triaza-spiro[4.5]decan-4-one (Example 73d). rac-1-Cyclohexylmethyl-8-(2-oxo-cyclohexyl)-1,3,8-triaza-spiro[4.5]decan-4-one was obtained as light yellow solid; MS (ISP): 348.3 MH$^+$.

c) (rac,cis)-1-Cyclohexylmethyl-8-(2-hydroxy-2-phenyl-cyclohexyl)-1,3,8-triaza-spiro[4.5]decan-4-one The title compound was prepared from rac-1-cyclohexylmethyl-8-(2-oxo-cyclohexyl)-1,3,8-triaza-spiro[4.5]decan-4-one and phenyl-lithium in analogy of the procedure described for the synthesis of (rac,cis)-8-(2-hydroxy-2-phenyl-cyclohexyl)-1-(3-methyl-butyl)-1,3,8-triaza-spiro[4.5]decan-4-one (Example 73e). (rac,cis)-1-Cyclohexylmethyl-8-(2-hydroxy-2-phenyl-cyclohexyl)-1,3,8-triaza-spiro[4.5]decan-4-one was obtained as colorless solid; MS (ISP): 426.3 MH$^+$.

Example 95

(rac,cis)-8-(2-Hydroxy-2-phenyl-cyclohexyl)-1-propyl-1,3,8-triaza-spiro[4.5]decan-4-one a) (rac,trans)-8-(2-hydroxy-cyclohexyl)-1-propyl-1,3,8-triaza-spiro[4.5]decan-4-one

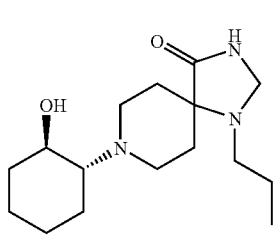

The title compound was prepared from (rac,trans)-8-(2-hydroxy-cyclohexyl)-1,3,8-triaza-spiro[4.5]decan-4-one and propionaldehyde in analogy of the procedure described for the synthesis of (rac,trans)-1-cyclohexylmethyl-8-(2-hydroxy-cyclohexyl)-1,3,8-triaza-spiro[4.5]decan-4-one (Example 94a). (rac,trans)-8-(2-Hydroxy-cyclohexyl)-1-propyl-1,3,8-triaza-spiro[4.5]decan-4-one was obtained as colorless solid; MS (ISP): 296.3 MH$^+$.

b) rac-8-(2-Oxo-cyclohexyl)-1-propyl-1,3,8-triaza-spiro[4.5]decan-4-one

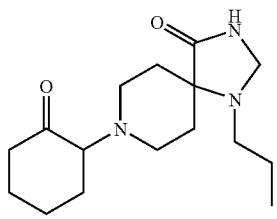

The title compound was prepared from (rac,trans)-8-(2-hydroxy-cyclohexyl)-1-propyl-1,3,8-triaza-spiro[4.5]decan-4-one in analogy of the procedure described for the synthesis of rac-1-(3-methyl-butyl)-8-(2-oxo-cyclohexyl)-1,3,8-triaza-spiro[4.5]decan-4-one (Example 73d). rac-1-Cyclohexylmethyl-8-(2-oxo-cyclohexyl)-1,3,8-triaza-spiro[4.5]decan-4-one was obtained as yellow gum; MS (ISP): 294.3 MH$^+$.

c) (rac,cis)-8-(2-Hydroxy-2-phenyl-cyclohexyl)-1-propyl-1,3,8-triaza-spiro[4.5]decan-4-one The title compound was prepared from rac-8-(2-oxo-cyclohexyl)-1-propyl-1,3,8-triaza-spiro[4.5]decan-4-one and phenyl-lithium in analogy of the procedure described for the synthesis of (rac,cis)-8-(2-hydroxy-2-phenyl-cyclohexyl)-1-(3-methyl-butyl)-1,3,8-triaza-spiro[4.5]decan-4-one (Example 73e). (rac,cis)-8-(2-Hydroxy-2-phenyl-cyclohexyl)-1-propyl-1,3,8-triaza-spiro[4.5]decan-4-one was obtained as light yellow foam; MS (ISP): 372.3 MH$^+$.

Example 96

(rac,cis)-8-(2-Hydroxy-2-phenyl-cyclohexyl)-1-isobutyl-1,3,8-triaza-spiro[4.5]decan-4-one a) (rac,trans)-8-(2-Hydroxy-cyclohexyl)-1-isobutyl-1,3,8-triaza-spiro[4.5]decan-4-one

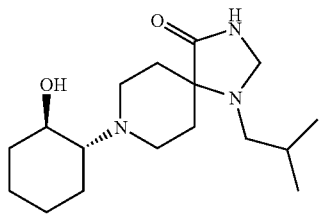

The title compound was prepared from (rac,trans)-8-(2-hydroxy-cyclohexyl)-1,3,8-triaza-spiro[4.5]decan-4-one and isobutyraldehyde in analogy of the procedure described for the synthesis of (rac,trans)-1-cyclohexylmethyl-8-(2-hydroxy-cyclohexyl)-1,3,8-triaza-spiro[4.5]decan-4-one (Example 94a). (rac,trans)-8-(2-hydroxy-cyclohexyl)-1-isobutyl-1,3,8-triaza-spiro[4.5]decan-4-one was obtained as colorless solid; MS (ISP): 310.3 MH$^+$.

b) rac-1-iso-Butyl-8-(2-oxo-cyclohexyl)-1,3,8-triaza-spiro[4.5]decan-4-one

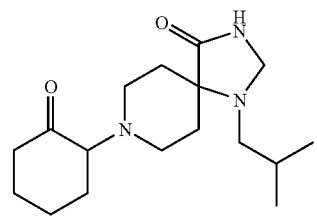

The title compound was prepared from (rac,trans)-8-(2-hydroxy-cyclohexyl)-1-isobutyl-1,3,8-triaza-spiro[4.5]decan-4-one in analogy of the procedure described for the synthesis of rac-1-(3-methyl-butyl)-8-(2-oxo-cyclohexyl)-1,3,8-triaza-spiro[4.5]decan-4-one (Example 73d). rac-1-isobutyl-8-(2-oxo-cyclohexyl)-1,3,8-triaza-spiro[4.5]decan-4-one was obtained as yellow foam; MS (ISP): 308.3 MH$^+$.

c) (rac,cis)-8-(2-Hydroxy-2-phenyl-cyclohexyl)-1-isobutyl-1,3,8-triaza-spiro[4.5]decan-4-one The title compound was prepared from rac-1-isobutyl-8-(2-oxo-cyclohexyl)-1,3,8-triaza-spiro[4.5]decan-4-one and phenyl-lithium in analogy of the procedure described for the synthesis of (rac,cis)-8-(2-hydroxy-2-phenyl-cyclohexyl)-1-(3-methyl-butyl)-1,3,8-triaza-spiro[4.5]decan-4-one (Example 73e). (rac,cis)-8-(2-Hydroxy-2-phenyl-cyclohexyl)-1-isobutyl-1,3,8-triaza-spiro[4.5]decan-4-one was obtained as colorless oil; MS (ISP): 386.4 MH$^+$.

Example 97

(rac,cis)-1-(3,3-Dimethyl-butyl)-8-(2-hydroxy-2-phenyl-cyclohexyl)-1,3,8-triaza-spiro[4.5]decan-4-one a) (rac,trans)-1-(3,3-Dimethyl-butyl)-8-(2-hydroxy-cyclohexyl)-1,3,8-triaza-spiro[4.5]decan-4-one

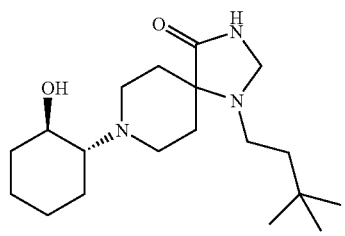

The title compound was prepared from (rac,trans)-8-(2-hydroxy-cyclohexyl)-1,3,8-triaza-spiro[4.5]decan-4-one and 3,3-dimethylbutyraldehyde in analogy of the procedure described for the synthesis of (rac,trans)-1-cyclohexylmethyl-8-(2-hydroxy-cyclohexyl)-1,3,8-triaza-spiro[4.5]decan-4-one (Example 94a). (rac,trans)-1-(3,3-Dimethyl-butyl)-8-(2-hydroxy-cyclohexyl)-1,3,8-triaza-spiro[4.5]decan-4-one was obtained as yellow oil; MS (ISP): 338.3 MH$^+$.

b) rac-1-(3,3-dimethyl-butyl)-8-(2-oxo-cyclohexyl)-1,3,8-triaza-spiro[4.5]decan-4-one

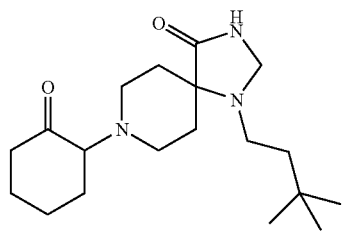

The title compound was prepared from (rac,trans)-1-(3,3-dimethyl-butyl)-8-(2-hydroxy-cyclohexyl)-1,3,8-triaza-spiro[4.5]decan-4-one in analogy of the procedure described for the synthesis of rac-1-(3-methyl-butyl)-8-(2-oxo-cyclohexyl)-1,3,8-triaza-spiro[4.5]decan-4-one (Example 73d). rac-1-(3,3-Dimethyl-butyl)-8-(2-oxo-cyclohexyl)-1,3,8-triaza-spiro[4.5]decan-4-one was obtained as yellow solid; MS (ISP): 336.3 MH$^+$.

c) (rac,cis)-1-(3,3-Dimethyl-butyl)-8-(2-hydroxy-2-phenyl-cyclohexyl)-1,3,8-triaza-spiro[4.5]decan-4-one The title compound was prepared from rac-1-(3,3-dimethyl-butyl)-8-(2-oxo-cyclohexyl)-1,3,8-triaza-spiro[4.5]decan-4-one and phenyl-lithium in analogy of the procedure described for the synthesis of (rac,cis)-8-(2-hydroxy-2-phenyl-cyclohexyl)-1-(3-methyl-butyl)-1,3,8-triaza-spiro[4.5]decan-4-one (Example 73e). (rac,cis)-1-(3,3-Dimethyl-butyl)-8-(2-hydroxy-2-phenyl-cyclohexyl)-1,3,8-triaza-spiro[4.5]decan-4-one was obtained as yellow oil; MS (ISP): 414.3 MH$^+$.

Example 98

(rac,cis)-8-(4-Hydroxy-4-phenyl-tetrahydro-pyran-3-yl)-1-(3,3,3-trifluoro-propyl)-1,3,8-triaza-spiro[4.5]decan-4-one (rac,trans)-8-(4-Hydroxy-tetrahydro-pyran-3-yl)-1,3,8-triaza-spiro[4.5]decan-4-one

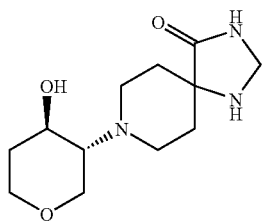

A solution of 550 mg (3.54 mmol) 1,3,8-triaza-spiro[4.5]decan-4-one and 390 mg (3.90 mmol) 3,7-dioxa-bicyclo[4.1.0]heptane in 8 ml EtOH was heated by microwave irradiation to 150° C. for 30 min. Then the reaction mixture was evaporated and the residue purified by prep. HPLC on reverse phase (YMC, ODS-AQ, $C_{18}$) with a gradient of AcOEt/MeOH with 0% to 60% methanol: 180 mg (rac,trans)-8-(4-hydroxy-tetrahydro-pyran-3-yl)-1,3,8-triaza-spiro[4.5]decan-4-one as colorless crystals; MS (ISP): 256.2 MH$^+$.

(rac,cis)-8-(4-Hydroxy-4-phenyl-tetrahydro-pyran-3-yl)-1-(3,3,3-trifluoro-propyl)-1,3,8-triaza-spiro[4.5]decan-4-one The title compound was prepared from (rac,trans)-8-(4-hydroxy-tetrahydro-pyran-3-yl)-1,3,8-triaza-spiro[4.5]decan-4-one in analogy of the sequence described for (rac,cis)-8-(2-hydroxy-2-phenyl-cyclohexyl)-1-(3,3,3-trifluoro-propyl)-1,3,8-triaza-spiro[4.5]decan-4-one (Example 93): (a) Alkylation with 3,3,3-trifluoropropane (Example 93b), b) hydrogenation (Example 93c), c) oxidation (Example 93d), and d) reaction with phenyl-lithium (Example 93e) provided (rac,cis)-8-(4-hydroxy-4-phenyl-tetrahydro-pyran-3-yl)-1-(3,3,3-trifluoro-propyl)-1,3,8-triaza-spiro[4.5]decan-4-one as colorless crystals: MS (ISP): 428.3 MH$^+$.

Example 99

(rac,cis)-8-(4-Hydroxy-4-phenyl-tetrahydro-pyran-3-yl)-1-phenyl-1,3,8-triaza-spiro[4.5]decan-4-one a) (rac,trans)-8-(4-hydroxy-tetrahydro-pyran-3-yl)-1-phenyl-1,3,8-triaza-spiro[4.5]decan-4-one

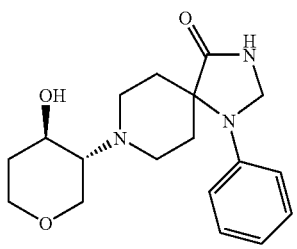

The title compound was prepared from 3,7-dioxa-bicyclo[4.1.0]heptane (Tetrahedron (1974), 30(22), 4013–20) and 1-phenyl-1,3,8-triaza-spiro[4,5]decan-4-one in analogy of the procedure described for the synthesis of (rac,trans)-8-(2-hydroxy-cyclohexyl)-1-(3-methyl-butyl)-1,3,8-triaza-spiro[4.5]decan-4-one (Example 73c). (rac,trans)-8-(4-Hydroxy-tetrahydro-pyran-3-yl)-1-phenyl-1,3,8-triaza-spiro[4.5]decan-4-one was obtained as colorless solid; MS (ISP): 332.3 MH$^+$.

b) rac-8-(4-Oxo-tetrahydro-pyran-3-yl)-1-phenyl-1,3,8-triaza-spiro[4.5]decan-4-one

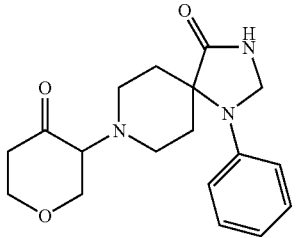

The title compound was prepared from (rac,trans)-8-(4-hydroxy-tetrahydro-pyran-3-yl)-1-phenyl-1,3,8-triaza-spiro[4.5]decan-4-one in analogy of the procedure described for the synthesis of rac-1-(3-methyl-butyl)-8-(2-oxo-cyclohexyl)-1,3,8-triaza-spiro[4.5]decan-4-one (Example 73d). rac-8-(4-Oxo-tetrahydro-pyran-3-yl)-1-phenyl-1,3,8-triaza-spiro[4.5]decan-4-one was obtained as colorless solid; MS (ISP): 330.3 MH$^+$.

c) (rac,cis)-8-(4-Hydroxy-4-phenyl-tetrahydro-pyran-3-yl)-1-phenyl-1,3,8-triaza-spiro[4.5]decan-4-one The tide compound was prepared from rac-8-(4-oxo-tetrahydro-pyran-3-yl)-1-phenyl-1,3,8-triaza-spiro[4.5]decan-4-one and phenyl-lithium in analogy of the procedure described for the synthesis of (rac,cis)-8-(2-hydroxy-2-phenyl-cyclohexyl)-1-(3-methyl-butyl)-1,3,8-triaza-spiro[4.5]decan-4-one (Example 73e). (rac,cis)-8-(4-Hydroxy-4-phenyl-tetrahydro-pyran-3-yl)-1-phenyl-1,3,8-triaza-spiro[4.5]decan-4-one was obtained as colorless solid; MS (ISP): 408.4 MH$^+$.

Example 100

(rac,cis)-8-(3-Hydroxy-3-phenyl-tetrahydro-pyran-4-yl)-1-phenyl-1,3,8-triaza-spiro[4.5]decan-4-one a) (rac,trans)-8-(3-Hydroxy-tetrahydro-pyran-4-yl)-1-phenyl-1,3,8-triaza-spiro[4.5]decan-4-one

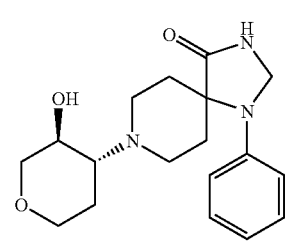

The title compound was prepared from 3,7-dioxa-bicyclo[4.1.0]heptane (Tetrahedron (1974), 30(22), 4013–20) and 1-phenyl-1,3,8-triazaspiro[4.5]decan-4-one in analogy of the procedure described for the synthesis of (rac,trans)-8-(2-hydroxy-cyclohexyl)-1-(3-methyl-butyl)-1,3,8-triaza-spiro[4.5]decan-4-one (Example 73c). (rac,trans)-8-(3-Hydroxy-tetrahydro-pyran-4-yl)-1-phenyl-1,3,8-triaza-spiro[4.5]decan-4-one was obtained as colorless solid; MS (ISP): 332.3 MH+.

b) rac-8-(3-Oxo-tetrahydro-pyran-4-yl)-1-phenyl-1,3,8-triaza-spiro[4.5]decan-4-one

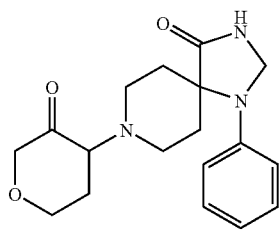

The title compound was prepared from (rac,trans)-8-(3-hydroxy-tetrahydro-pyran-4-yl)-1-phenyl-1,3,8-triaza-spiro[4.5]decan-4-one in analogy of the procedure described for the synthesis of rac-1-(3-methyl-butyl)-8-(2-oxo-cyclohexyl)-1,3,8-triaza-spiro[4.5]decan-4-one (Example 73d). rac-8-(3-Oxo-tetrahydro-pyran-4-yl)-1-phenyl-1,3,8-triaza-spiro[4.5]decan-4-one was obtained as light yellow solid; MS (ISP): 330.3 MH+.

c) (rac,cis)-8-(3-Hydroxy-3-phenyl-tetrahydro-pyran-4-yl)-1-phenyl-1,3,8-triaza-spiro[4.5]decan-4-one The title compound was prepared from rac-8-(3-oxo-tetrahydro-pyran-4-yl)-1-phenyl-1,3,8-triaza-spiro[4.5]decan-4-one and phenyl-lithium in analogy of the procedure described for the synthesis of (rac,cis)-8-(2-hydroxy-2-phenyl-cyclohexyl)-1-(3-methyl-butyl)-1,3,8-triaza-spiro[4.5]decan-4-one (Example 73e). (rac,cis)-8-(3-Hydroxy-3-phenyl-tetrahydro-pyran-4-yl)-1-phenyl-1,3,8-triaza-spiro[4.5]decan-4-one was obtained as colorless solid; MS (ISP): 408.4 MH+.

Procedure G

Example 101

(rac,trans)-8-(2-Hydroxy-2-phenyl-cyclohexyl)-1-phenyl-1,3,8-triaza-spiro[4.5]decan-4-one The title compound was prepared from rac-1-phenyl-7-oxa-bicyclo[4.1.0]heptane (Tetrahedron (1965), 21, 3277–83) and 1-phenyl-1,3,8-triazaspiro[4,5]decan-4-one in analogy of the procedure described for the synthesis of (rac,trans)-8-(2-hydroxy-cyclohexyl)-1-(3-methyl-butyl)-1,3,8-triaza-spiro[4.5]decan-4-one (Example 73c). (rac,trans)-8-(2-Hydroxy-2-phenyl-cyclohexyl)-1-phenyl-1,3,8-triaza-spiro[4.5]decan-4-one was obtained as colorless solid; MS (ISP): 406.5 MH+.

Procedure H

Example 102

(rac,cis)-3-Benzyl-8-(2-hydroxy-2-phenyl-cyclohexyl)-1-phenyl-1,3,8-triaza-spiro[4.5]decan-4-one a) 3-Benzyl-4-oxo-1-phenyl-1,3,8-triaza-spiro[4.5]decane-8-carboxylic acid tert-butyl ester

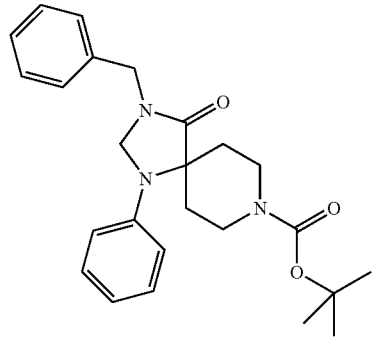

The title compound was prepared from 4-oxo-1-phenyl-1,3,8-triaza-spiro[4.5]decane-8-carboxylic acid tert-butyl ester (J. Med. Chem. (1992), 35, 423–30) and benzylbromide in analogy of the procedure described for the synthesis of (rac,cis)-3-methyl-1-phenyl-8-(2-phenyl-cyclohexyl)-1,3,8-triaza-spiro[4.5]decan-4-one (Example 69) by using potassium bis(trimethylsilyl)amide as base instead of sodium hydride. 3-Benzyl-4-oxo-1-phenyl-1,3,8-triaza-spiro[4.5]decane-8-carboxylic acid tert-butyl ester was obtained as colorless solid; MS (ISP): 322.6 [M-($CO_2$+ isobutylene)]+.

b) 3-Benzyl-1-phenyl-1,3,8-triaza-spiro[4.5]decan-4-one

A solution of 2.16 g (5.12 mmol) 3-benzyl-4-oxo-1-phenyl-1,3,8-triaza-spiro[4.5]decane-8-carboxylic acid tert-butyl ester in 43 ml ethyl acetate and 25 ml of a saturated solution of HCl in ether was stirred at ambient temperature for 90 min. The resulting suspension was filtered, the filtrate was dissolved in water and treated with saturated $NaHCO_3$ and extracted with dichloromethane. The combined organic extracts were washed with brine, dried over $MgSO_4$, filtered and evaporated to provide 3-benzyl-1-phenyl-1,3,8-triaza-spiro[4.5]decan-4-one as a brown solid; MS (ISP): 322.5 MH+.

c) rac-3-Benzyl-8-(2-oxo-cyclohexyl)-1-phenyl-1,3,8-triaza-spiro[4.5]decan-4-one

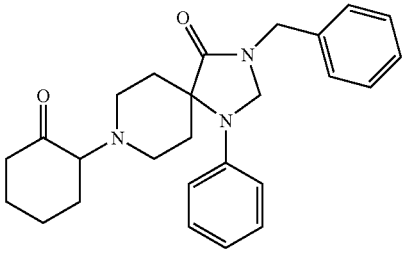

A solution of 0.30 g (0.93 mmol) 3-benzyl-1-phenyl-1,3,8-triaza-spiro[4.5]decan-4-one, 0.14 g (1.0 mmol) 2-chloro-cyclohexane, and 0.2 ml (1.4 mmol) triethylamine in ethanol was refluxed overnight. The reaction mixture was cooled to ambient temperature, concentrated and then quenched with saturated $NaHCO_3$ and extracted with ethyl acetate. The combined organic extracts were washed with brine, dried over $MgSO_4$, filtered and evaporated. Purification of the crude product over a silica gel plug (10:1) with n-heptane/AcOEt as eluent provided 0.14 g rac-3-benzyl-8-(2-oxocyclohexyl)-1-phenyl-1,3,8-triaza-spiro[4.5]decan-4-one as a light yellow oil; MS (ISP): 418.4 MH⁺.

d) (rac,cis)-3-Benzyl-8-(2-hydroxy-2-phenyl-cyclohexyl)-1-phenyl-1,3,8-triaza-spiro[4.5]decan-4-one The title compound was prepared from rac-3-benzyl-8-(2-oxo-cyclohexyl)-1-phenyl-1,3,8-triaza-spiro[4.5]decan-4-one and phenyl-lithium in analogy of the procedure described for the synthesis of (rac,cis)-8-(2-hydroxy-2-phenyl-cyclohexyl)-1-(3-methyl-butyl)-1,3,8-triaza-spiro[4.5]decan-4-one (Example 73e). (rac,cis)-3-benzyl-8-(2-hydroxy-2-phenyl-cyclohexyl)-1-phenyl-1,3,8-triaza-spiro[4.5]decan-4-one was obtained as colorless oil; MS (ISP): 496.3 MH⁺.

Procedure I

Example 103

8-(1-Methyl-2-phenyl-cyclohexyl)-1-phenyl-1,3,8-triaza-spiro[4.5]decan-4-one a) 1-(4-Oxo-1-phenyl-1,3,8-triaza-spiro[4.5]dec-8-yl)-2-phenyl-cyclohexanecarbonitrile

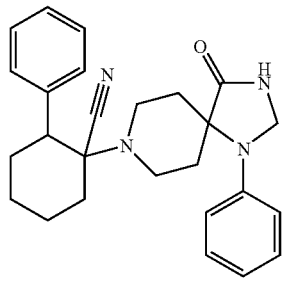

To a mixture of 0.26 g (1.15 mmol) 1-phenyl-1,3,8-triaza-spiro[4.5]decan-4-one in 2 ml AcOH were added 0.2 g (1.15 mmol) rac-2-phenylcyclohexanone followed by the dropwise addition of 0.86 ml (5.75 mmol) trimethylsilyl cyanide. The resulting mixture was heated to 80° C. overnight. The reaction mixture was poured onto 200 ml iced sodium hydroxide (25%,) and the resulting colorless solid filtered off. The solid was dissolved in 50 ml dichloromethane and washed with 40 ml water, dried over Na₂SO₄, filtered and evaporated: 52 mg 1-(4-oxo-1-phenyl-1,3,8-triaza-spiro[4.5]dec-8-yl)-2-phenyl-cyclohexane-carbonitrile as colorless solid; MS (ISP): 415.4 MH⁺.

b) 8-(1-Methyl-2-phenyl-cyclohexyl)-1-phenyl-1,3,8-triaza-spiro[4.5]decan-4-one

To a solution of 20 mg (0.048 mmol) 1-(4-oxo-1-phenyl-1,3,8-triaza-spiro[4.5]dec-8-yl)-2-phenyl-cyclohexane-carbonitrile in 1.5 ml dry THF under argon at 0° C. were added 0.03 ml (0.096 mmol) methyl magnesium bromide (3M solution in THF) and the resulting mixture heated to reflux for 3.5 h. The reaction mixture was cooled to ambient temperature, quenched by the addition of water and the product extracted with ethyl acetate. The combined organic extracts were then washed with brine, dried over Na₂SO₄, filtered and evaporated. The residue was purified by chromatography on silica gel eluting with hexane/ethyl acetate: 10 mg 8-(1-methyl-2-phenyl-cyclohexyl)-1-phenyl-1,3,8-triaza-spiro[4.5]decan-4-one as colorless solid; MS (ISP): 404.6 MH⁺.

| $R^1$ | $R^2$ | $R^3$ | $R^4$ | $R^5$ | $R^6$ | X | A-A | Expl. |
|---|---|---|---|---|---|---|---|---|
| phenyl | phenyl | H | H | H | H | H | CH₂CH₂ | 1 rac/cis |
| phenyl (wedge) | phenyl | H | H | H | H | H | CH₂CH₂ | 2 1S, 2S) |
| phenyl (dashed) | phenyl | H | H | H | H | H | CH₂CH₂ | 3 1R, 2R) |

-continued

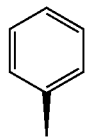

| R¹ | R² | R³ | R⁴ | R⁵ | R⁶ | X | A-A | Expl. |
|---|---|---|---|---|---|---|---|---|
| phenyl | 4-methylphenyl | H | H | H | H | H | (CH₂)₃ | 4 rac/cis |
| phenyl | 4-methylphenyl | H | i-propyl | H | H | H | CH₂CH₂ | 5 rac/cis |
| phenyl | 4-methylphenyl | H | benzyl | H | H | H | CH₂CH₂ | 6 rac/cis |
| phenyl | 4-methylphenyl | H | phenyl | H | H | H | CH₂CH₂ | 7 rac/cis |
| 4-methylphenyl | 4-methylphenyl | H | H | H | H | H | CH₂CH₂ | 8 rac/cis |
| 4-methoxyphenyl | 4-methylphenyl | H | H | H | H | H | CH₂CH₂ | 9 rac/cis |
| 4-fluorophenyl | 4-methylphenyl | H | H | H | H | H | CH₂CH₂ | 10 rac/cis |
| 4-chlorophenyl | 4-methylphenyl | H | H | H | H | H | CH₂CH₂ | 11 rac/cis |

-continued
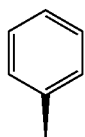
| R¹ | R² | R³ | R⁴ | R⁵ | R⁶ | X | A-A | Expl. |
|---|---|---|---|---|---|---|---|---|
| 3-Cl-C₆H₄ | C₆H₅ | H | H | H | H | H | CH₂CH₂ | 12 rac/cis |
| 3,4-diCl-C₆H₃ | C₆H₅ | H | H | H | H | H | CH₂CH₂ | 13 rac/cis |
| 4-Cl-3-CF₃-C₆H₃ | C₆H₅ | H | H | H | H | H | CH₂CH₂ | 14 rac/cis |
| 3-CH₃-C₆H₄ | C₆H₅ | H | H | H | H | H | CH₂CH₂ | 15 rac/cis |
| 2-pyridyl | C₆H₅ | H | H | H | H | H | CH₂CH₂ | 16 rac/cis |
| 4-Cl-C₆H₄ | 4-F-C₆H₄ | H | H | H | H | H | CH₂CH₂ | 17 rac/cis |
| C₆H₅ | 4-F-C₆H₄ | H | H | H | H | H | CH₂CH₂ | 18 rac/cis |

-continued
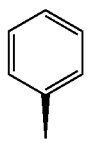
| R¹ | R² | R³ | R⁴ | R⁵ | R⁶ | X | A-A | Expl. |
|---|---|---|---|---|---|---|---|---|
| phenyl | 4-Cl-phenyl | H | H | H | H | H | CH₂CH₂ | 19 rac/cis |
| phenyl | 4-CH₃-phenyl | H | H | H | H | H | CH₂CH₂ | 20 rac/cis |
| phenyl | 4-OCH₃-phenyl | H | H | H | H | H | CH₂CH₂ | 21 rac/cis |
| 4-CH₃-phenyl | 4-F-phenyl | H | H | H | H | H | CH₂CH₂ | 22 rac/cis |
| 4-OCH₃-phenyl | 4-F-phenyl | H | H | H | H | H | CH₂CH₂ | 23 rac/cis |
| 4-F-phenyl | 4-F-phenyl | H | H | H | H | H | CH₂CH₂ | 24 rac/cis |

-continued

| R¹ | R² | R³ | R⁴ | R⁵ | R⁶ | X | A-A | Expl. |
|---|---|---|---|---|---|---|---|---|
| 3,5-dimethylphenyl | 4-fluorophenyl | H | H | H | H | H | CH₂CH₂ | 25 rac/cis |
| 3,5-difluorophenyl | 4-fluorophenyl | H | H | H | H | H | CH₂CH₂ | 26 rac/cis |
| 3,4-dichlorophenyl | 4-fluorophenyl | H | H | H | H | H | CH₂CH₂ | 27 rac/cis |
| 3,4-dichlorophenyl | 4-fluorophenyl | H | H | H | H | H | CH₂CH₂ | 28 rac/cis |
| 3,5-dichlorophenyl | 4-fluorophenyl | H | H | H | H | H | CH₂CH₂ | 29 rac/cis |
| 3-fluoro-5-trifluoromethylphenyl | 4-fluorophenyl | H | H | H | H | H | CH₂CH₂ | 30 rac/cis |
| 4-chlorophenyl | n-propyl | H | H | H | H | H | CH₂CH₂ | 31 rac/cis |

-continued
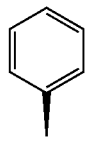
| R¹ | R² | R³ | R⁴ | R⁵ | R⁶ | X | A-A | Expl. |
|---|---|---|---|---|---|---|---|---|
| 3-Cl-C₆H₄ | 4-Cl-C₆H₄ | H | H | H | H | H | CH₂CH₂ | 32 rac/cis |
| 4-Cl-C₆H₄ | n-Pr | H | H | H | H | H | CH₂CH₂ | 33 rac/cis |
| 4-F-C₆H₄ | n-Pr | H | H | H | H | H | CH₂CH₂ | 34 rac/cis |
| 3,5-(CH₃)₂-C₆H₃ | n-Pr | H | H | H | H | H | CH₂CH₂ | 35 rac/cis |
| 3,5-F₂-C₆H₃ | n-Pr | H | H | H | H | H | CH₂CH₂ | 36 rac/cis |
| 3,4-Cl₂-C₆H₃ | n-Pr | H | H | H | H | H | CH₂CH₂ | 37 rac/cis |
| 3,5-Cl₂-C₆H₃ | n-Pr | H | H | H | H | H | CH₂CH₂ | 38 rac/cis |
| 3-CF₃-5-Cl-C₆H₃ | n-Pr | H | H | H | H | H | CH₂CH₂ | 39 rac/cis |

-continued
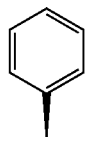
| R¹ | R² | R³ | R⁴ | R⁵ | R⁶ | X | A-A | Expl. |
|---|---|---|---|---|---|---|---|---|
| Ph | n-Pr | H | H | H | H | H | CH₂CH₂ | 40 rac/cis |
| Ph | i-Bu | H | H | H | H | H | CH₂CH₂ | 41 rac/cis |
| Ph | cyclohexylmethyl | H | H | H | H | H | CH₂CH₂ | 42 rac/cis |
| Ph | CH₂CH₂CH₂CF₃ | H | H | H | H | H | CH₂CH₂ | 43 rac/cis |
| Ph | CH₂CH₂OCH₃ | H | H | H | H | H | CH₂CH₂ | 44 rac/cis |
| Ph | CH₂CH₂-piperidinyl | H | H | H | H | H | CH₂CH₂ | 45 rac/cis |
| Ph | CH₂CH₂-morpholinyl | H | H | H | H | H | CH₂CH₂ | 46 rac/cis |
| Ph | CH₂CH₂Ph | H | H | H | H | H | CH₂CH₂ | 47 rac/cis |

-continued
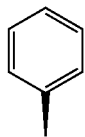
| R¹ | R² | R³ | R⁴ | R⁵ | R⁶ | X | A-A | Expl. |
|---|---|---|---|---|---|---|---|---|
| Ph | n-Pr | H | H | H | H | H | CH₂CH₂ | 48 rac/cis |
| Ph | cyclopropyl | H | H | H | H | H | CH₂CH₂ | 49 rac/cis |
| Ph | n-Bu | H | H | H | H | H | CH₂CH₂ | 50 rac/cis |
| Ph | iso-Bu | H | H | H | H | H | CH₂CH₂ | 51 rac/cis |
| Ph | cyclobutyl | H | H | H | H | H | CH₂CH₂ | 52 rac/cis |
| Ph | n-pentyl | H | H | H | H | H | CH₂CH₂ | 53 rac/cis |
| Ph | iso-pentyl | H | H | H | H | H | CH₂CH₂ | 54 rac/cis |
| Ph | cyclopentyl | H | H | H | H | H | CH₂CH₂ | 55 rac/cis |
| Ph | cyclohexylmethyl | H | H | H | H | H | CH₂CH₂ | 56 rac/cis |

-continued
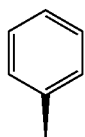
| R¹ | R² | R³ | R⁴ | R⁵ | R⁶ | X | A-A | Expl. |
|---|---|---|---|---|---|---|---|---|
| phenyl | phenethyl | H | H | H | H | H | CH₂CH₂ | 57 rac/cis |
| phenyl | cyclohexylpropyl | H | H | H | H | H | CH₂CH₂ | 58 rac/cis |
| phenyl | 3,4-dichlorophenylpropyl | H | H | H | H | H | CH₂CH₂ | 59 rac/cis |
| phenyl | n-octyl | H | H | H | H | H | CH₂CH₂ | 60 rac/cis |
| phenyl | 4-(CF₃)phenyl | H | H | H | H | H | CH₂CH₂ | 61 rac/cis |
| phenyl | CH₂CH₂CF₃ | H | H | H | H | H | CH₂CH₂ | 62 rac/cis |

-continued

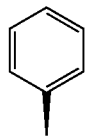

| R¹ | R² | R³ | R⁴ | R⁵ | R⁶ | X | A-A | Expl. |
|---|---|---|---|---|---|---|---|---|
| phenyl | N-propyl-thiomorpholine | H | H | H | H | H | CH₂CH₂ | 63 rac/cis |
| phenyl | 4-methylphenyl | H | CH₃ | H | H | H | CH₂CH₂ | 64 rac/cis |
| phenyl | 4-methylphenyl | H | CH₂CH₃ | H | H | H | CH₂CH₂ | 65 rac/cis |
| phenyl | 4-methylphenyl | CH₃ | CH₃ | H | H | H | CH₂CH₂ | 66 rac/cis |
| phenyl | cyclopropylmethyl | H | H | H | H | H | CH₂CH₂ | 67 rac/cis |
| phenyl | phenyl | H | H | H | H | H | CH₂CH₂ | 68 rac/cis |
| phenyl | phenyl | H | H | CH₃ | H | H | CH₂CH₂ | 69 rac/cis |
| phenyl | phenyl | H | H | CH₂CH₃ | H | H | CH₂CH₂ | 70 rac/cis |

-continued

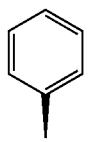

| R¹ | R² | R³ | R⁴ | R⁵ | R⁶ | X | A-A | Expl. |
|---|---|---|---|---|---|---|---|---|
| phenyl | phenyl | H | H | isopropyl | H | H | CH₂CH₂ | 71 rac/cis |
| phenyl | phenyl | H | H | benzyl (CH₂-phenyl) | H | H | CH₂CH₂ | 72 rac/cis |
| phenyl | isobutyl | H | H | H | H | OH | CH₂CH₂ | 73 rac/cis |
| phenyl | phenyl | H | H | H | H | OH | CH₂CH₂ | 74 rac/cis |
| 4-F-phenyl | phenyl | H | H | H | H | OH | CH₂CH₂ | 75 rac/cis |
| 2-CH₃-phenyl | phenyl | H | H | H | H | OH | CH₂CH₂ | 76 rac/cis |
| 4-pyridyl | phenyl | H | H | H | H | OH | CH₂CH₂ | 77 rac/cis |
| 4-Cl-phenyl | phenyl | H | H | H | H | OH | CH₂CH₂ | 78 rac/cis |

-continued
| R¹ | R² | R³ | R⁴ | R⁵ | R⁶ | X | A-A | Expl. |
|---|---|---|---|---|---|---|---|---|
| 3-pyridyl | phenyl | H | H | H | H | OH | CH₂CH₂ | 79 rac/cis |
| 2-pyridyl | phenyl | H | H | H | H | OH | CH₂CH₂ | 80 rac/cis |
| 3-Cl-phenyl | phenyl | H | H | H | H | OH | CH₂CH₂ | 81 rac/cis |
| 3-MeO-phenyl | phenyl | H | H | H | H | OH | CH₂CH₂ | 82 rac/cis |
| 4-Me-phenyl | phenyl | H | H | H | H | OH | CH₂CH₂ | 83 rac/cis |
| 3,4-diCl-phenyl | phenyl | H | H | H | H | OH | CH₂CH₂ | 84 rac/cis |
| 4-MeO-phenyl | phenyl | H | H | H | H | OH | CH₂CH₂ | 85 rac/cis |

-continued
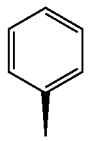
| R¹ | R² | R³ | R⁴ | R⁵ | R⁶ | X | A-A | Expl. |
|---|---|---|---|---|---|---|---|---|
| 4-CF₃-C₆H₄- | C₆H₅- | H | H | H | H | OH | CH₂CH₂ | 86 rac/cis |
| 4-F-C₆H₄- | C₆H₅- | H | H | H | H | OH | CH₂CH₂ | 87 rac/cis |
| 4-Cl-C₆H₄- | 4-F-C₆H₄- | H | H | H | H | OH | CH₂CH₂ | 88 rac/cis |
| 4-F-C₆H₄- | 4-F-C₆H₄- | H | H | H | H | OH | CH₂CH₂ | 89 rac/cis |
| 4-Cl-C₆H₄- | 4-Cl-C₆H₄- | H | H | H | H | OH | CH₂CH₂ | 90 rac/cis |
| 4-F-C₆H₄- | 4-CH₃-C₆H₄- | H | H | H | H | OH | CH₂CH₂ | 91 rac/cis |
| 4-Cl-C₆H₄- | 4-OCH₃-C₆H₄- | H | H | H | H | OH | CH₂CH₂ | 92 rac/cis |

-continued
| R¹ | R² | R³ | R⁴ | R⁵ | R⁶ | X | A-A | Expl. |
|---|---|---|---|---|---|---|---|---|
| Ph | CH₂CH₂CH₂CF₃ | H | H | H | H | OH | CH₂CH₂ | 93 rac/cis |
| Ph | CH₂-cyclohexyl | H | H | H | H | OH | CH₂CH₂ | 94 rac/cis |
| Ph | n-propyl | H | H | H | H | OH | CH₂CH₂ | 95 rac/cis |
| Ph | isobutyl | H | H | H | H | OH | CH₂CH₂ | 96 rac/cis |
| Ph | neopentyl | H | H | H | H | OH | CH₂CH₂ | 97 rac/cis |
| Ph | CH₂CH₂CH₂CF₃ | H | H | H | H | OH | CH₂O | 98 rac/cis |
| Ph | Ph | H | H | H | H | OH | CH₂O | 99 rac/cis |
| Ph | Ph | H | H | H | H | OH | OCH₂ | 100 rac/cis |
| Ph | Ph | H | H | H | H | OH | CH₂CH₂ | 101 rac/trans |

-continued

| R¹ | R² | R³ | R⁴ | R⁵ | R⁶ | X | A-A | Expl. |
|---|---|---|---|---|---|---|---|---|
| (phenyl) | (tolyl) | H | H | (benzyl, with phenyl above as R⁵ ref) | H | OH | CH₂CH₂ | 102 rac/cis |
| (phenyl) | (tolyl) | H | H | H | CH₃ | H | CH₂CH₂ | 103 |

Tablet Formulation (Wet Granulation)

| | | mg/tablet | | | |
|---|---|---|---|---|---|
| Item | Ingredients | 5 mg | 25 mg | 100 mg | 500 mg |
| 1. | Compound of formula I | 5 | 25 | 100 | 500 |
| 2. | Lactose Anhydrous DTG | 125 | 105 | 30 | 150 |
| 3. | Sta-Rx 1500 | 6 | 6 | 6 | 30 |
| 4. | Microcrystalline Cellulose | 30 | 30 | 30 | 150 |
| 5. | Magnesium Stearate | 1 | 1 | 1 | 1 |
| | Total | 167 | 167 | 167 | 831 |

Manufacturing Procedure
1. Mix items 1, 2, 3 and 4 and granulate with purified water.
2. Dry the granules at 50° C.
3. Pass the granules through suitable milling equipment.
4. Add item 5 and mix for three minutes; compress on a suitable press.

Capsule Formulation

| | | mg/capsule | | | |
|---|---|---|---|---|---|
| Item | Ingredients | 5 mg | 25 mg | 100 mg | 500 mg |
| 1. | Compound of formula I | 5 | 25 | 100 | 500 |
| 2. | Hydrous Lactose | 159 | 123 | 148 | — |
| 3. | Corn Starch | 25 | 35 | 40 | 70 |
| 4. | Talc | 10 | 15 | 10 | 25 |
| 5. | Magnesium Stearate | 1 | 2 | 2 | 5 |
| | Total | 200 | 200 | 300 | 600 |

Manufacturing Procedure
1. Mix items 1, 2 and 3 in a suitable mixer for 30 minutes.
2. Add items 4 and 5 and mix for 3 minutes.
3. Fill into a suitable capsule.

The invention claimed is:

1. A compound of formula

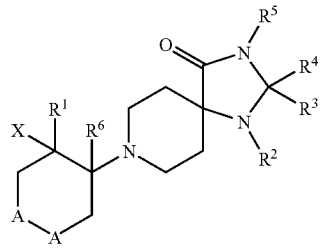

I wherein
A-A is —CH₂—CH₂—, —CH₂—CH₂—CH₂—, —CH₂—O— or —O—CH₂—;
X is hydrogen or hydroxy;
$R^1$ is aryl or heteroaryl, each of which is unsubstituted or substituted by one or more substituents selected from the group consisting of lower alkyl, lower alkoxy, halogen and trifluoromethyl;
$R^2$ is aryl or heteroaryl, each of which is unsubstituted or substituted by one or more substituents selected from the group consisting of lower alkyl, lower alkoxy, halogen and trifluoromethyl,
or is lower alkyl, —(CH₂)$_n$-cycloalkyl, —(CH₂)$_n$—CF₃,
—(CH₂)$_p$—O-lower alkyl, —(CH₂)$_y$-phenyl, optionally substituted by halogen, lower alkyl, lower alkoxy or trifluoromethyl,
or is —(CH₂)$_p$—NR'R", wherein R' and R" form together with the N-atom to which they are attached a heterocyclic ring, selected from the group consisting of piperidine, morpholine, thiomorpholine and 1,1-dioxo-thiomorpholine;
$R^3$, $R^4$ are each independently hydrogen, lower alkyl, phenyl or benzyl;
$R^5$ is hydrogen, lower alkyl or benzyl;
$R^6$ is hydrogen or lower alkyl;

n is 0, 1 or 2;
p is 2 or 3; and
y is 1 or 2;
or a pharmaceutically acceptable acid addition salt thereof.

2. A compound of formula I in accordance with claim 1, wherein A-A is —CH$_2$—CH$_2$—.

3. A compound of formula I' in accordance with claim 2,

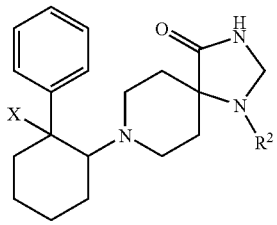

I' wherein
X is hydrogen or hydroxy;
R$^2$ is —(CH$_2$)$_n$-phenyl, which is unsubstituted or substituted by one or more substituents selected from the group consisting of lower alkyl, lower alkoxy, halogen and trifluoromethyl
or a pharmaceutically acceptable acid addition salt thereof.

4. A compound of formula I' in accordance with claim 3, selected from
(rac,cis)-1-phenyl-8-(2-phenyl-cyclohexyl)-1,3,8-triaza-spiro[4.5]decan-4-one,
(1R,2R)-1-phenyl-8-(2-phenyl-cyclohexyl)-1,3,8-triaza-spiro[4.5]decan-4-one,
(rac,cis)-1-(4-chloro-phenyl)-8-(2-phenyl-cyclohexyl)-1,3,8-triaza-spiro[4.5]decan-4-one,
(rac,cis)-1-phenethyl-8-(2-phenyl-cyclohexyl)-1,3,8-triaza-spiro[4.5]decan-4-one,
(rac,cis)-1-(3,4-dichloro-phenyl)-8-(2-phenyl-cyclohexyl)-1,3,8-triaza-spiro[4.5]decan-4-one,
(rac,cis)-8-(2-phenyl-cyclohexyl)-1-(4-trifluoromethyl-phenyl)-1,3,8-triaza-spiro[4.5]decan-4-one,
(rac,trans)-1-phenyl-8-(2-phenyl-cyclohexyl)-1,3,8-triaza-spiro[4.5]decan-4-one,
(rac,trans)-8-(2-hydroxy-2-phenyl-cyclohexyl)-1-phenyl-1,3,8-triaza-spiro[4.5]decan-4-one,
(rac,cis)-1-(4-methoxy-phenyl)-8-(2-phenyl-cyclohexyl)-1,3,8-triaza-spiro[4.5]decan-4-one and
(rac,cis)-8-(2-hydroxy-2-phenyl-cyclohexyl)-1-phenyl-1,3,8-triaza-spiro[4.5]decan-4-one.

5. A compound of formula I' as described in claim 2, wherein X is hydrogen or hydroxy and R$^2$ is lower alkyl or —(CH$_2$)$_n$-cycloalkyl.

6. A compound of formula I' in accordance with claim 5, selected from
(rac,cis)-1-isobutyl-8-(2-phenyl-cyclohexyl)-1,3,8-triaza-spiro[4.5]decan-4-one,
(rac,cis)-1-pentyl-8-(2-phenyl-cyclohexyl)-1,3,8-triaza-spiro[4.5]decan-4-one,
(rac,cis)-1-(3-methyl-butyl)-8-(2-phenyl-cyclohexyl)-1,3,8-triaza-spiro[4.5]decan-4-one,
(rac,cis)-1-cyclohexylmethyl-8-(2-phenyl-cyclohexyl)-1,3,8-triaza-spiro[4.5]decan-4-one,
(rac,cis)-1-(2-cyclohexyl-ethyl)-8-(2-phenyl-cyclohexyl)-1,3,8-triaza-spiro[4.5]decan-4-one,
(rac,cis)-1-hexyl-8-(2-phenyl-cyclohexyl)-1,3,8-triaza-spiro[4.5]decan-4-one and
(rac,cis)-1-cyclohexylmethyl-8-(2-hydroxy-2-phenyl-cyclohexyl)-1,3,8-triaza-spiro[4.5]decan-4-one.

7. A compound of formula I″ in accordance with claim 1

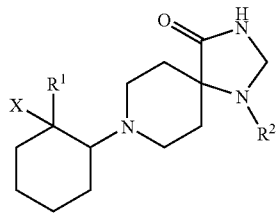

I″ wherein
X is hydrogen or hydroxy;
R$^1$ is phenyl substituted by one or more substituents selected from the group consisting of lower alkyl, lower alkoxy, halogen and trifluoromethyl;
R$^2$ is phenyl, which is unsubstituted or substituted by one or more substituents, selected from the group consisting of lower alkyl, lower alkoxy, halogen and trifluoromethyl.

8. A compound of formula I″ in accordance with claim 7, selected from
(rac,cis)-1-phenyl-8-(2-p-tolyl-cyclohexyl)-1,3,8-triaza-spiro[4.5]decan-4-one,
(rac,cis)-8-[2-(4-fluoro-phenyl)-cyclohexyl]-1-phenyl-1,3,8-triaza-spiro[4.5]decan-4-one,
(rac,cis)-8-[2-(4-chloro-phenyl)-cyclohexyl]-1-phenyl-1,3,8-triaza-spiro[4.5]decan-4-one,
(rac,cis)-8-[2-(3,4-dichloro-phenyl)-cyclohexyl]-1-phenyl-1,3,8-triaza-spiro[4.5]decan-4-one,
(rac,cis)-8-[2-(4-chloro-phenyl)-cyclohexyl]-1-(4-fluoro-phenyl)-1,3,8-triaza-spiro[4.5]decan-4-one,
(rac,cis)-1-(4-fluoro-phenyl)-8-(2-p-tolyl-cyclohexyl)-1,3,8-triaza-spiro[4.5]decan-4-one,
(rac,cis)-1-(4-fluoro-phenyl)-8-[2-(4-fluoro-phenyl)-cyclohexyl]-1,3,8-triaza-spiro[4.5]decan-4-one, and
(rac,cis)-8-[2-(4-fluoro-phenyl)-2-hydroxy-cyclohexyl]-1-phenyl-1,3,8-triaza-spiro[4.5]decan-4-one.

9. A compound of formula I″ in accordance with claim 7, selected from
(rac,cis)-8-(2-hydroxy-2-o-tolyl-cyclohexyl)-1-phenyl-1,3,8-triaza-spiro[4.5]decan-4-one,
(rac,cis)-8-[2-(4-chloro-phenyl)-2-hydroxy-cyclohexyl]-1-phenyl-1,3,8-triaza-spiro[4.5]decan-4-one,
(rac,cis)-1-(4-fluoro-phenyl)-8-[2-(4-fluoro-phenyl)-2-hydroxy-cyclohexyl]-1,3,8-triaza-spiro[4.5]decan-4-one,
(rac,cis)-8-[2-(4-chloro-phenyl)-2-hydroxy-cyclohexyl]-1-(4-fluoro-phenyl)-1,3,8-triaza-spiro[4.5]decan-4-one,
(rac,cis)-1-(4-chloro-phenyl)-8-[2-(4-fluoro-phenyl)-2-hydroxy-cyclohexyl]-1,3,8-triaza-spiro[4.5]decan-4-one,
(rac,cis)-1-(4-chloro-phenyl)-8-[2-(4-chloro-phenyl)-2-hydroxy-cyclohexyl]-1,3,8-triaza-spiro[4.5]decan-4-one,
(rac,cis)-8-[2-(4-fluoro-phenyl)-2-hydroxy-cyclohexyl]-1-p-tolyl-1,3,8-triaza-spiro[4.5]decan-4-one and
(rac,cis)-8-[2-(4-chloro-phenyl)-2-hydroxy-cyclohexyl]-1-(4-methoxy-phenyl)-1,3,8-triaza-spiro[4.5]decan-4-one.

10. A compound of formula I in accordance with claim 1, wherein X is hydrogen or hydroxy, and $R^1$ is pyridin-4-yl.

11. A compound of formula I in accordance with claim 10, wherein the compound is
(rac,cis) 8-(2-hydroxy-2-pyridin-4-yl-cyclohexyl)-1-phenyl-1,3,8-triaza-spiro[4.5]decan-4-one.

12. A compound of formula I in accordance with claim 1, wherein A-A is —O—CH$_2$—.

13. A compound of formula I in accordance with claim 12, wherein the compound is
(rac,cis)-8-(3-hydroxy-3-phenyl-tetrahydro-pyran-4-yl)-1-phenyl-1,3,8-triaza-spiro[4.5]decan-4-one.

14. A compound of formula I in accordance with claim 1, wherein A-A is —CH$_2$—O—.

15. A compound of formula I in accordance with claim 14, selected from
(rac,cis)-8-(4-hydroxy-4-phenyl-tetrahydro-pyran-3-yl)-1-(3,3,3-trifluoro-propyl)-1,3,8-triaza-spiro[4.5]decan-4-one and
(rac,cis)-8-(4-hydroxy-4-phenyl-tetrahydro-pyran-3-yl)-1-phenyl-1,3,8-triaza-spiro[4.5]decan-4-one.

16. A compound of formula I in accordance with claim 1, wherein A-A is —(CH$_2$)$_3$—.

17. A process for preparation of a compound of formula I

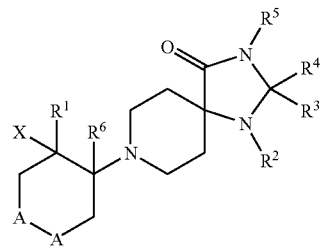

wherein
A-A is —CH$_2$—CH$_2$—, —CH$_2$—CH$_2$—CH$_2$—, —CH$_2$—O— or —O—CH$_2$—;
X is hydrogen or hydroxy;
$R^1$ is aryl or heteroaryl, each of which is unsubstituted or substituted by one or more substituents selected from the group consisting of lower alkly, lower alkoxy, halogen and trifluoromethyl;
$R^2$ is aryl or heteroaryl, each of which is unsubstituted or substituted by one or more substituents selected from the group consisting of lower alkyl, lower alkoxy, halogen and trifluoromethyl,
or is lower alkyl, —(CH$_2$)$_n$-cycloalkyl, —(CH$_2$)$_n$—CF$_3$,
—(CH$_2$)$_p$—O-lower alkyl, —(CH$_2$)$_y$-phenyl, optionally substituted by halogen, lower alkyl, lower alkoxy or trifluoromethyl,
or is —(CH$_2$)$_p$—NR'R", wherein R' and R" form together with the N-atom to which they are attached a heterocyclic ring, selected from the group consisting of piperidine, morpholine, thiomorpholine and 1,1-dioxo-thiomorpholine;
$R^3$, $R^4$ are each independently hydrogen, lower alkly, phenyl or benzyl;
$R^5$ is hydrogen, lower alkyl or benzyl;
$R^6$ is hydrogen or lower alkyl;
n is 0, 1 or 2;
p is 2 or 3; and
y is 1 or 2;

or a pharmaceutically acceptable acid addition salt thereof which comprises
reacting a compound of formula

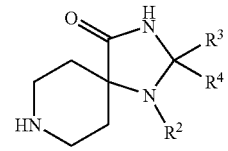

with a compound of formula

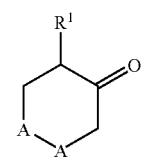

to produce a compound of formula Ia

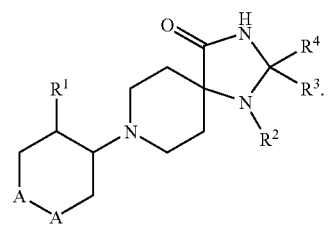

18. A process for preparation of a compound of formula I

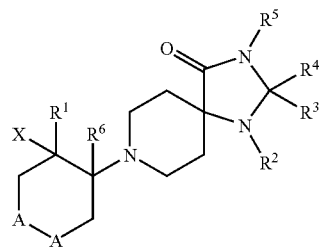

wherein
A-A is —CH$_2$—CH$_2$—, —CH$_2$—CH$_2$—CH$_2$—, —CH$_2$—O— or —O—CH$_2$—;
X is hydrogen or hydroxy;
$R^1$ is aryl or heteroaryl, each of which is unsubstituted or substituted by one or more substituents selected from the group consisting of lower alkyl, lower alkoxy, halogen and trifluoromethyl;
$R^2$ is aryl or heteroaryl, each of which is unsubstituted or substituted by one or more substituents selected from the group consisting of lower alkyl, lower alkoxy, halogen and trifluoromethyl,
or is lower alkyl, —(CH$_2$)$_n$-cycloalkyl, —(CH$_2$)$_n$—CF$_3$,
—(CH$_2$)$_p$—O-lower alkyl, —(CH$_2$)$_y$-phenyl, optionally substituted by halogen, lower alkyl, lower alkoxy or trifluoromethyl,
or is —(CH$_2$)$_p$—NR'R", wherein R' and R" form together with the N-atom to which they are attached a heterocyclic ring, selected from the group consisting of piperidine, morpholine, thiomorpholine and 1,1-dioxo-thiomorpholine;
$R^3$, $R^4$ are each independently hydrogen, lower alkly, phenyl or benzyl;

R⁵ is hydrogen, lower alkyl or benzyl;
R⁶ is hydrogen or lower alkyl;
n is 0, or 2;
p is 2 or 3; and
y is 1 or 2;
or a pharmaceutically acceptable acid addition salt thereof which comprises
reacting a compound of formula

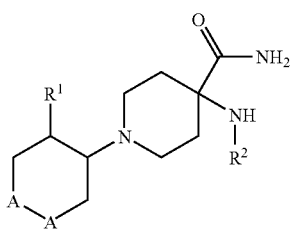

with corresponding acetals or ketals
to produce a compound of formula

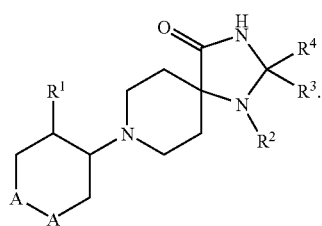

19. A process for preparation of a compound of formula I

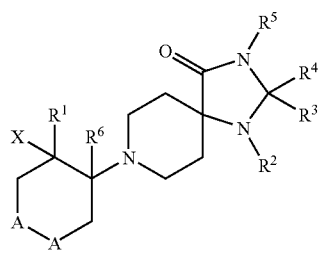

wherein
A-A is —CH₂—CH₂—, —CH₂—CH₂—CH₂—, —CH₂—O— or —O—CH₂—;
X is hydrogen or hydroxy;
R¹ is aryl or heteroaryl, each of which is unsubstituted or substituted by one or more substituents selected from the group consisting of lower alkyl, lower alkoxy, halogen and trifluoromethyl;
R² is aryl or heteroaryl, each of which is unsubstituted or substituted by one or more substituents selected from the group consisting of lower alkyl, lower alkoxy, halogen and trifluoromethyl,
or is lower alkyl, —(CH₂)ₙ-cycloalkyl, —(CH₂)ₙ—CF₃,
—(CH₂)ₚ—O-lower alkyl, —(CH₂)ᵧ-phenyl, optionally substituted by halogen, lower alkyl, lower alkoxy or trifluoromethyl,
or is —(CH₂)ₚ—NR'R", wherein R' and R" form together with the N-atom to which they are attached a heterocyclic ring, selected from the group consisting of piperidine, morpholine, thiomorpholine and 1,1-dioxo-thiomorpholine;
R³, R⁴ are each independently hydrogen, lower alkyl, phenyl or benzyl;
R⁵ is hydrogen, lower alkyl or benzyl;
R⁶ is hydrogen or lower alkyl;
n is 0, 1 or 2;
p is 2 or 3; and
y is 1 or 2;
or a pharmaceutically acceptable acid addition salt thereof which comprises
reacting a compound of formula

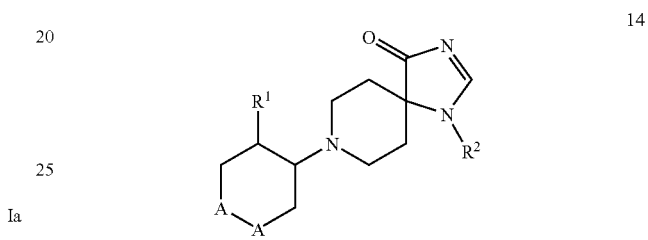

with a Grignard reagent R³MgX to produce a compound of formula

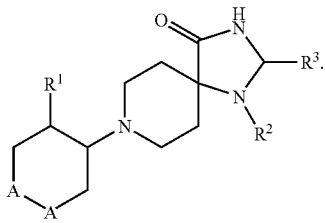

20. A process for preparation of a compound of formula I

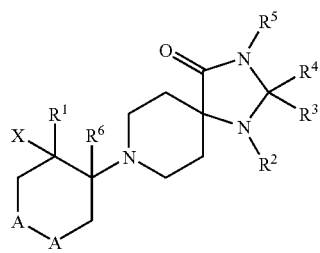

wherein
A-A is —CH₂—CH₂—, —CH₂—CH₂—CH₂—, —CH₂—O— or —O—CH₂—;
X is hydrogen or hydroxy;
R¹ is aryl or heteroaryl, each of which is unsubstituted or substituted by one or more substituents selected from the group consisting of lower alkyl, lower alkoxy, halogen and trifluoromethyl;
R² is aryl or heteroaryl, each of which is unsubstituted or substituted by one or more substituents selected from the group consisting of lower alkyl, lower alkoxy, halogen and trifluoromethyl,
or is lower alkyl, —(CH₂)ₙ-cycloalkyl, —(CH₂)ₙ—CF₃, —(CH$_2$)$_p$—O-lower alkyl, —(CH$_2$)$_y$-phenyl, optionally substituted by halogen, lower alkly, lower alkoxy or trifluoromethyl, or is —(CH$_2$)$_p$—NR'R", wherein R' and R" form together with the N-atom to which they are attached a heterocyclic ring, selected from the group consisting of piperidine, morpholine, thiomorpholine and 1,1-dioxo-thiomorpholine;

R$^3$, R$^4$ are each independently hydrogen, lower alkyl, phenyl or benzyl;

R$^5$ is hydrogen, lower alkyl or benzyl;

R$^6$ is hydrogen or lower alkyl;

n is 0, 1 or 2;

p is 2 or 3; and y is 1 or 2;

or a pharmaceutically acceptable acid addition salt thereof which comprises reacting a compound of formula

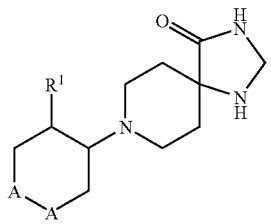

Id with a compound of formula R$^{2'}$CHO
to produce a compound of formula

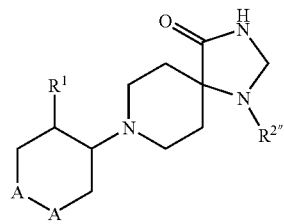

Ib' wherein

R$^{2'}$ is lower alkyl, —(CH$_2$)$_x$-cycloalkyl, —(CH$_2$)$_x$—CF$_3$, —(CH$_2$)$_y$—O-lower alkyl, —(CH$_2$)$_x$-phenyl, optionally substituted by halogen, lower alkyl, lower alkoxy or trifluoromethyl, or is —(CH$_2$)$_y$—NR'R", wherein R' and R" form together with the N-atom to which they are attached a heterocyclic ring selected from the group consisting of piperidine, morpholine, thiomorpholine and 1,1-dioxo-thiomorpholine and R$^{2''}$ is lower alkyl, —(CH$_2$)$_y$-cycloalkyl, —(CH$_2$)$_y$—CF$_3$, —(CH$_2$)$_p$—O-lower alkyl, —(CH$_2$)$_y$-phenyl, optionally substituted by halogen, lower alkyl, lower alkoxy or trifluoromethyl, or is —(CH$_2$)$_p$—NR'R", wherein R' and R" form together with the N-atom to which they are attached a heterocyclic ring, selected from the group consisting of piperidine, morpholine, thiomorpholine and 1,1-dioxo-thiomorpholine;

x is 0 or 1;

y is 1 or 2; and p is 2 or 3.

21. A process for the preparation of a compound of formula I

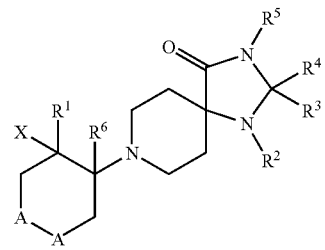

I wherein

A-A is —CH$_2$—CH$_2$—, —CH$_2$—CH$_2$—CH$_2$—, —CH$_2$—O— or —O—CH$_2$—;

X is hydrogen or hydroxy;

R$^1$ is aryl or heteroaryl, each of which is unsubstituted or substituted by one or more substituents selected from the group consisting of lower alkyl, lower alkoxy, halogen and trifluoromethyl;

R$^2$ is aryl or heteroaryl, each of which is unsubstituted or substituted by one or more substituents selected from the group consisting of lower alkyl, lower alkoxy, halogen and trifluoromethyl, or is lower alkyl, —(CH$_2$)$_n$-cycloalkyl, —(CH$_2$)$_n$—CF$_3$, —(CH$_2$)$_p$—O-lower alkyl, —(CH$_2$)$_y$-phenyl, optionally substituted by halogen, lower alkyl, lower alkoxy or trifluoromethyl, or is —(CH$_2$)$_p$—NR'R", wherein R' and R" form together with the N-atom to which they are attached a heterocyclic ring, selected from the group consisting of piperidine, morpholine, thiomorpholine and 1,1-dioxo-thiomorpholine;

R$^3$, R$^4$ are each independently hydrogen, lower alkyl, phenyl or benzyl;

R$^5$ is hydrogen, lower alkyl or benzyl;

R$^6$ is hydrogen or lower alkyl;

n is 0, 1 or 2;

p is 2 or 3; and y is 1 or 2;

or a pharmaceutically acceptable acid addition salt thereof which comprises reducing a compound of formula

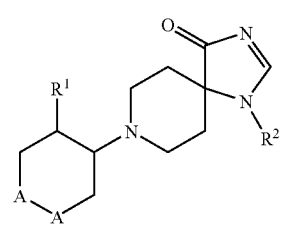

14 to produce a compound of formula

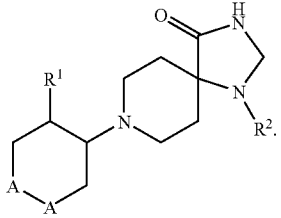

Ib

22. A process for the preparation of a compound of formula I

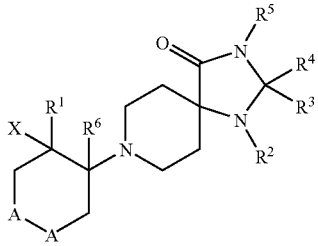

I wherein
A-A is —CH₂—CH₂—, —CH₂—CH₂—CH₂—, —CH₂—O— or —O—CH₂—;
X is hydrogen or hydroxy;
R¹ is aryl or heteroaryl, each of which is unsubstituted or substituted by one or more substituents selected from the group consisting of lower alkyl, lower alkoxy, halogen and trifluoromethyl;
R² is aryl or heteroaryl, each of which is unsubstituted or substituted by one or more substituents selected from the group consisting of lower alkyl, lower alkoxy, halogen and trifluoromethyl,
or is lower alkyl, —(CH₂)ₙ-cycloalkyl, —(CH₂)ₙ—CF₃,
—(CH₂)ₚ—O-lower alkyl, —(CH₂)ᵧ-phenyl, optionally substituted by halogen, lower alkyl, lower alkoxy or trifluoromethyl,
or is —(CH₂)ₚ—NR'R", wherein R' and R" form together with the N-atom to which they are attached a heterocyclic ring, selected from the group consisting of piperidine, morpholine, thiomorpholine and 1,1-dioxo-thiomorpholine;
R³, R⁴ are each independently hydrogen, lower alkyl, phenyl or benzyl;
R⁵ is hydrogen, lower alkyl or benzyl;
R⁶ is hydrogen or lower alkyl;
n is 0, 1 or 2;
p is 2 or 3; and
y is 1 or 2;
or a pharmaceutically acceptable acid addition salt thereof which comprises reacting a compound of formula

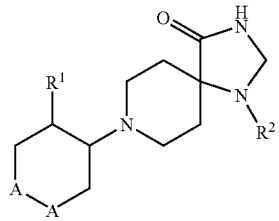

Ib with a compound of formula R⁵X
to produce a compound of formula

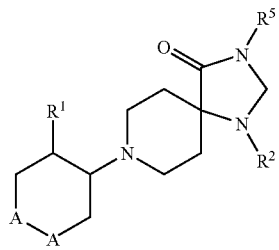

Ie wherein X is halogen.

23. A process for the preparation of a compound of formula I

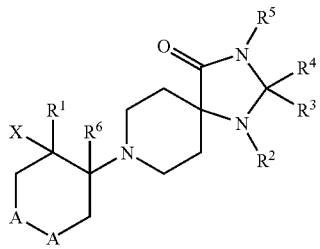

I wherein
A-A is —CH₂—CH₂—, —CH₂—CH₂—CH₂—, —CH₂—O— or —O—CH₂—;
X is hydrogen or hydroxy;
R¹ is aryl or heteroaryl, each of which is unsubstituted or substituted by one or more substituents selected from the group consisting of lower alkyl, lower alkoxy, halogen and trifluoromethyl;
R² is aryl or heteroaryl, each of which is unsubstituted or substituted by one or more substituents selected from the group consisting of lower alkyl, lower alkoxy, halogen and trifluoromethyl,
or is lower alkyl, —(CH₂)ₙ-cycloalkyl, —(CH₂)ₙ—CF₃,
—(CH₂)ₚ—O-lower alkyl, —(CH₂)ᵧ-phenyl, optionally substituted by halogen, lower alkyl, lower alkoxy or trifluoromethyl,
or is —(CH₂)ₚ—NR'R", wherein R' and R" form together with the N-atom to which they are attached a heterocyclic ring, selected from the group consisting of piperidine, morpholine, thiomorpholine and 1,1-dioxo-thiomorpholine;
R³, R⁴ are each independently hydrogen, lower alkly, phenyl or benzyl;
R⁵ is hydrogen, lower alkyl or benzyl;
R⁶ is hydrogen or lower alkyl;
n is 0, 1 or 2;
p is 2 or 3; and
y is 1 or 2;

or a pharmaceutically acceptable acid addition salt thereof which comprises
reacting a compound of formula

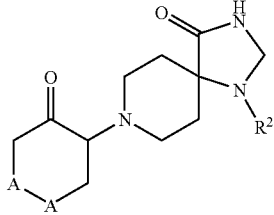
21 with a compound of formula LiR¹
to produce a compound of formula

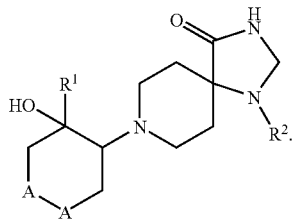
1f

24. A process for the preparation of a compound of formula I

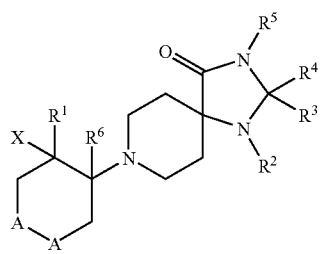
I wherein
A-A is —CH₂—CH₂—, —CH₂—CH₂—CH₂—, —CH₂—O— or —O—CH₂—;
X is hydrogen or hydroxy,
R is aryl or heteroaryl, each of which is unsubstituted or substituted by one or more substituents selected from the group consisting of lower alkyl, lower alkoxy, halogen and trifluoromethyl;
R² is aryl or heteroaryl, each of which is unsubstituted or substituted by one or more substituents selected from the group consisting of lower alkyl, lower alkoxy, halogen and trifluoromethyl,
or is lower alkyl, —(CH₂)$_p$-cycloalkyl, —(CH₂)$_n$—CF₃,
—(CH₂)$_p$—O-lower alkyl, —(CH₂)$_y$-phenyl, optionally substituted by halogen, lower alkyl, lower alkoxy or trifluoromethyl,
or is —(CH₂)$_p$—NR'R", wherein R' and R" form together with the N-atom to which they are attached a heterocyclic ring, selected from the group consisting of piperidine, morpholine, thiomorpholine and 1,1-dioxo-thiomorpholine;
R³, R⁴ are each independently hydrogen, lower alkyl, phenyl or benzyl;
R⁵ is hydrogen, lower alkyl or benzyl;
R⁶ is hydrogen or lower alkyl;
n is 0, 1 or 2;
p is 2 or 3; and
y is 1 or 2;

or a pharmaceutically acceptable acid addition salt thereof which comprises
reacting a compound of formula

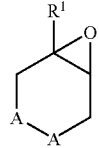
23 with a compound of formula

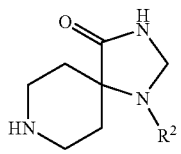
10 to produce a compound of formula

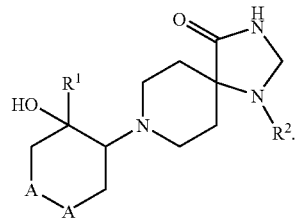
1f

25. A process for the preparation of a compound of formula I

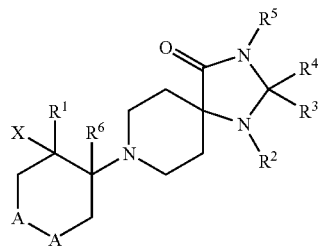
I wherein
A-A is —CH₂—CH₂—, —CH₂—CH₂—CH₂—, —CH₂—O— or —O—CH₂—;
X is hydrogen or hydroxy;
R¹ is aryl or heteroaryl, each of which is unsubstituted or substituted by one or more substituents selected from the group consisting of lower alkyl, lower alkoxy, halogen and trifluoromethyl;
R² is aryl or heteroaryl, each of which is unsubstituted or substituted by one or more substituents selected from the group consisting of lower alkyl, lower alkoxy, halogen and trifluoromethyl,
or is lower alkyl, —(CH₂)$_n$-cycloalkyl, —(CH₂)$_n$—CF₃,
—(CH₂)$_p$—O-lower alkyl, —(CH₂)$_y$-phenyl, optionally substituted by halogen, lower alkyl, lower alkoxy or trifluoromethyl,
or is —(CH₂)$_p$—NR'R", wherein R' and R" form together with the N-atom to which they are attached a heterocyclic ring, selected from the group consisting of piperidine, morpholine, thiomorpholine and 1,1-dioxo-thiomorpholine;
R³, R⁴ are each independently hydrogen, lower alkyl, phenyl or benzyl;
R⁵ is hydrogen, lower alkyl or benzyl;

$R^6$ is hydrogen or lower alkyl;
n is 0, 1 or 2;
p is 2 or 3; and
y is 1 or 2;
or a pharmaceutically acceptable acid addition salt thereof which comprises
reacting a compound of formula
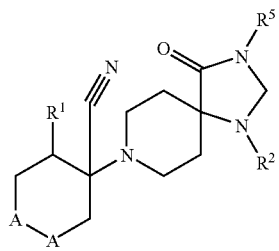
with $R^6MgX$
to produce a compound of formula
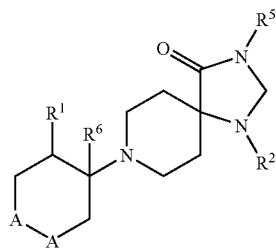
Ih
wherein X is halogen and $R^6$ is lower alkyl.
* * * * *